United States Patent [19]
Kamano et al.

[11] Patent Number: 5,981,439
[45] Date of Patent: *Nov. 9, 1999

[54] CYCLOHEXANEDIONE DERIVATIVES AND HERBICIDES CONTAINING THEM

[75] Inventors: Hideki Kamano, Sodegaura; Ichiro Nasuno, Ichihara; Hiroshi Yamamoto, Sodegaura; Kazuyoshi Koike, Ichihara, all of Japan

[73] Assignee: Idemitsu Kosan Co., Ltd., Tokyo, Japan

[*] Notice: This patent is subject to a terminal disclaimer.

[21] Appl. No.: 09/020,829

[22] Filed: Feb. 9, 1998

Related U.S. Application Data

[63] Continuation-in-part of application No. 08/876,980, Jun. 16, 1997, Pat. No. 5,801,121.

[30] Foreign Application Priority Data

Dec. 27, 1996 [JP] Japan .................................. 8-349866

[51] Int. Cl.$^6$ ........................... A01N 43/18; C07D 335/04
[52] U.S. Cl. ............................................. 504/288; 549/23
[58] Field of Search ..................... 549/23, 28; 504/288

[56] References Cited

U.S. PATENT DOCUMENTS

| | | |
|---|---|---|
| 5,468,878 | 11/1995 | Nasuno et al. . |
| 5,480,858 | 1/1996 | Sakamoto et al. . |
| 5,563,115 | 10/1996 | Barton et al. . |
| 5,767,289 | 6/1998 | Nakamura et al. ................... 549/23 |
| 5,801,121 | 9/1998 | Kamano et al. ..................... 504/288 |

FOREIGN PATENT DOCUMENTS

| | | |
|---|---|---|
| 0 283 261 A2 | 9/1988 | European Pat. Off. . |
| 61-155347 | 7/1986 | Japan . |
| 7-309869 | 11/1995 | Japan . |
| 8-41055 | 2/1996 | Japan . |
| 8-245618 | 9/1996 | Japan . |
| 9-25279 | 1/1997 | Japan . |
| 93/18031 | 9/1993 | WIPO . |
| 94/04524 | 3/1994 | WIPO . |
| 94/08988 | 4/1994 | WIPO . |
| 95/04054 | 2/1995 | WIPO . |
| 97/01550 | 1/1997 | WIPO . |
| 97/19087 | 5/1997 | WIPO . |

*Primary Examiner*—Deborah C. Lambkin
*Attorney, Agent, or Firm*—Frishauf, Holtz, Goodman, Langer & Chick, P.C.

[57] ABSTRACT

The present invention relates to cyclohexanedione derivatives or salts thereof and herbicides containing the cyclohexanedione derivatives and/or salts thereof as active ingredients, the cyclohexanedione derivatives having the general formula (I).

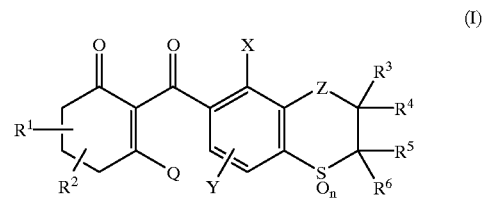

(I)

The cyclohexanedione derivatives or the salts thereof can selectively control a broad range of upland soil weeds at a low dosage without causing phytotoxicity on crops cultivated in upland fields such as corn, in both upland pre-emergence and post-emergence treatments.

42 Claims, No Drawings

CYCLOHEXANEDIONE DERIVATIVES AND HERBICIDES CONTAINING THEM

This application is a continuation-in-part application of application Ser. No. 08/876,980, filed Jun. 16, 1997, now U.S. Pat. No. 5,801,121.

TECHNICAL FIELD

The present invention relates to cyclohexanedione derivatives and herbicides containing them, more specifically, to cyclohexanedione derivatives which can control a broad range of upland weeds at a low dosage without causing phytotoxicity on crops such as corn, and herbicides containing them.

BACKGROUND ART

Herbicides are very important chemicals for labor-saving of weed control working and production improvement in horticultural crops. Herbicides have been therefore aggressively studied and developed for a long time, and a variety of chemicals are now practically used. However, it is still desired to develop novel herbicides having further superior herbicidal properties, particularly herbicides which can selectively control object weeds alone at a low dosage without causing phytotoxicity on cultivated crops.

During the planting time of corn, triazine-containing herbicides such as atrazine and acid anilide-containing herbicides such as alachlor and metolachlor have been conventionally used. However, atrazine shows low efficacy to grass weeds, and on the other hand, alachlor and metolachlor show low efficacy to broad-leaved weeds. It is therefore difficult at present to control grass weeds and broad-leaved weeds together simultaneously with a single herbicide. Further, these herbicides are undesirable in view of an environmental problem due to their high dosage requirement.

In view of the above circumstances, the present inventors have developed novel cyclohexanedione derivatives having a thiochroman ring and have filed patent applications therefor (WO94/04524 and WO94/08988). Typical examples of these compounds are as follows.

Compounds described in WO94/04524

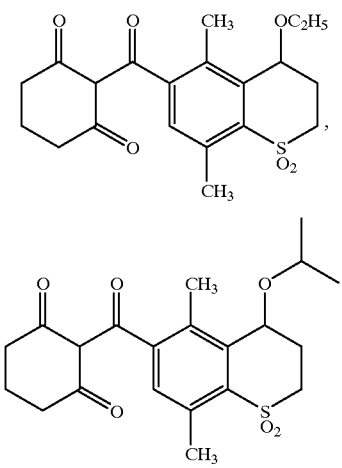

Compounds described in WO94/08988

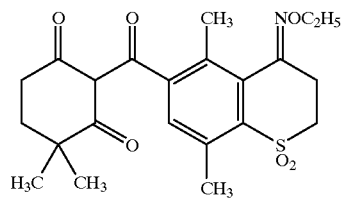

As a cyclohexanedione derivative having bicyclic properties, the following compounds have been disclosed (European Patent 94/283261).

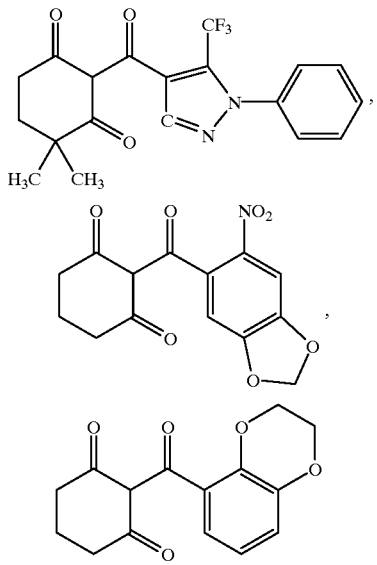

Since, however, the above compounds show phytotoxicity on sorgo and beet, it cannot be said that they have sufficient activity both in post-emergence treatment and pre-emergence treatment.

DISCLOSURE OF THE INVENTION

It is therefore an object of the present invention to provide a novel cyclohexanedione derivative which can control a broad range of upland weeds at a low dosage without causing phytotoxicity on crops such as corn, and a herbicide containing the same.

The present inventors have made diligent studies to overcome the above problems and have found that a cyclohexanedione derivative having a specific structure can control a broad range of upland weeds at a low dosage without causing phytotoxicity on crops such as corn, and the present invention has been completed on the basis of the above finding.

According to the present invention, the first object of the present invention is achieved by; (1) cyclohexanedion derivatives of the general formula (I) or salts thereof,

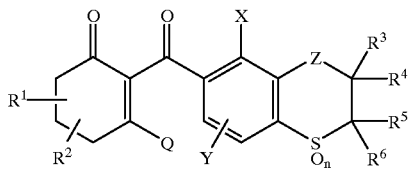

(I)

wherein each of $R^1$ and $R^2$ is independently a hydrogen atom or a $C_1$~$C_6$ alkyl group, each of $R^3$ to $R^6$ is independently a hydrogen atom, a $C_1$~$C_6$ alkyl group, a $C_1$~$C_5$ haloalkyl group or a halogen atom, n is 0, 1 or 2, X is a $C_1$~$C_6$ alkyl group, a $C_1$~$C_6$ haloalkyl group, a halogen atom, a $C_1$~$C_6$ alkoxy group, a $C_1$~$C_6$ haloalkoxy group, a $C_2$~$C_6$ alkoxyalkyl group, a $C_1$~$C_6$ alkylthio group, a $C_1$~$C_6$ haloalkylthio group, a $C_1$~$C_6$ alkylsulfinyl group or a $C_1$~$C_6$ alkylsulfonyl group, Y is a hydrogen atom, a $C_1$~$C_6$ alkyl group, $C_1$~$C_6$ haloalkyl group, a halogen atom, a $C_1$~$C_6$ alkoxy group, a $C_1$~$C_6$ haloalkoxy group or a $C_1$~$C_6$ alkoxyalkyl group, Z is a group of

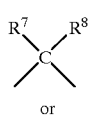

(a)

or

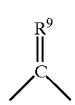

(b)

in which each of $R^7$ and $R^8$ is independently a hydrogen atom, a halogen atom, a $C_1$~$C_6$ alkyl group, a $C_1$~$C_6$ alkoxy group, a $C_1$~$C_6$ alkylthio group or a group of -$NR^{10}R^{11}$, provided that when $R^7$, $R^8$ or both is/are $C_1$~$C_6$ alkyl, $C_1$~$C_6$ alkoxy or $C_1$~$C_6$ alkylthio group(s), hydrogen atoms thereof may be replaced with 1 to 13 halogen atoms or $C_1$~$C_6$ alkoxy groups, provided that when the number of carbon atoms thereof is $C_2$~$C_6$, the group(s) may contain an unsaturated bond, further provided that when the number of carbon atoms thereof is $C_3$~$C_6$, the group(s) may have a cyclic structure, each of $R^{10}$ and $R^{11}$ is a hydrogen atom, a $C_1$~$C_6$ alkyl group or a $C_1$~$C_6$ alkylcarbonyl group, further provided that when both $R^7$ and $R^8$ are $C_1$~$C_6$ alkyl groups, $C_1$~$C_6$ alkoxy groups or $C_1$~$C_6$ alkylthio groups, carbon atoms of $R^7$ and $R^8$ may bond to each other to form a 3–7-membered ring, provided that when both $R^7$ and $R^8$ are alkyl groups, compounds of the general formula (I) in which X is a $C_1$~$C_6$ alkyl group, a halogen atom or a haloalkyl group and all of $R^3$, $R^4$, $R^5$ and $R^6$ are hydrogen atoms are excluded, provided that when one of $R^7$ and $R^8$ is an alkoxy group and when the other is a hydrogen atom, compounds of the general formula (I) in which X is a $C_1$~$C_6$ alkyl group and all of $R^3$, $R^4$, $R^5$ and $R^6$ are hydrogen atoms are excluded when no hydrogen atom of the alkoxy group is replaced with halogen or an alkoxy group or when the alkoxy group does not contain an unsaturated bond or an alkoxy group, and $R^9$ is an oxygen atom, a sulfur atom or a $C_1$~$C_6$ alkoxyimino group, provided that when $R^9$ is a $C_1$~$C_6$ alkoxyimino group, hydrogen atoms thereof may be replaced with 1 to 13 halogen atoms, provided that when the number of carbon atoms thereof is $C_2$~$C_6$, the $C_2$~$C_6$ alkoxyimino group may contain an unsaturated bond, and provided that when $R^9$ is an alkoxyimino group and when no hydrogen atom thereof is replaced with a halogen or when the alkoxyimino group does not contain an unsaturated bond, compounds of the general formula (I) in which X is a $C_1$~$C_6$ alkyl group and all of $R^3$, $R^4$, $R^5$ and $R^6$ are hydrogen atoms are excluded, and Q is a hydroxyl group or a group of

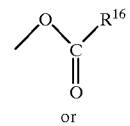

(c)

or

(d)

in which each of $R^{16}$ and $R^{17}$ is a $C_1$~$C_6$ alkyl group, a $C_1$~$C_6$ haloalkyl group or a phenyl group on which a $C_1$~$C_6$ alkyl group, a $C_1$~$C_6$ haloalkyl group, a halogen atom, a cyano group or a nitro group may be substituted, and m is 0, 1 or 2, (2) cyclohexanedione derivatives of the general formula (I-a1), or salts thereof,

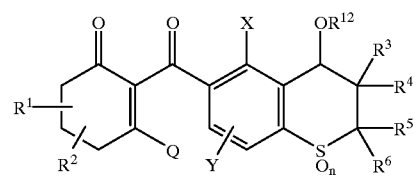

(I-a1)

wherein $R^1$ to $R^6$, n, X, Y and Q are as defined above, and $R^{12}$ is a $C_1$~$C_6$ alkyl group or a $C_1$~$C_6$ haloalkyl group, provided that $R^{12}$ may be substituted with a $C_1$~$C_6$ alkoxy group, provided that when the number of carbon atoms of $R^{12}$ is $C_2$~$C_6$, $R^{12}$ may contain an unsaturated bond, provided that when the number of carbon atoms of $R^{12}$ is $C_3$~$C_6$, $R^{12}$ may have a cyclic structure, further provided that when $R^{12}$ is a $C_1$~$C_6$ alkyl, compounds of the general formula (I-a1) in which X is a $C_1$~$C_6$ alkyl and all of $R^3$, $R^4$, $R^5$ and $R^6$ are hydrogen atoms are excluded, (3) cyclohexanedione derivatives of the general formula (I-a2), or salts thereof,

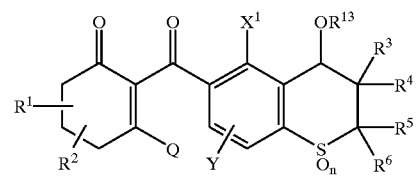

(I-a2)

wherein $R^1$ to $R^6$, n, Y and Q are as defined above, $R^{13}$ is a $C_1$~$C_6$ alkyl group, and $X^1$ is a $C_1$~$C_6$ haloalkyl group, a halogen atom, a $C_1$~$C_6$ alkoxy group, a $C_1$~$C_6$ haloalkoxy group, a $C_2$~$C_6$ alkoxyalkyl group, a $C_1$~$C_6$ alkylthio group, a $C_1$~$C_6$ haloalkylthio group, a $C_1$~$C_6$ alkylsulfinyl group or a $C_1$~$C_6$ alkylsulfonyl group, (4) cyclohexanedione derivatives of the general formula (I-a3), or salts thereof,

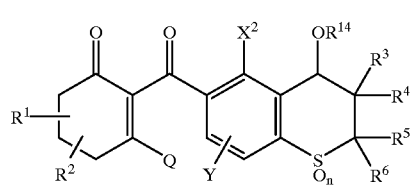
(I-a3)

wherein $R^1$ to $R^6$, n, Y and Q are as defined above, $R^{14}$ is a $C_1$~$C_6$ haloalkyl group, an alkoxyalkyl group, an alkenyl group, a haloalkenylalkyl group or an alkynylalkyl group, and $X^2$ is a $C_1$~$C_6$ alkyl group, a $C_1$~$C_6$ haloalkyl group, a halogen atom, a $C_1$~$C_6$ alkoxy group, a $C_1$~$C_6$ haloalkoxy group, a $C_2$~$C_6$ alkoxyalkyl group, a $C_1$~$C_6$ alkylthio group, a $C_1$~$C_6$ haloalkylthio group, a $C_1$~$C_6$ alkylsulfinyl group or a $C_1$~$C_6$ alkylsulfonyl group, (5) cyclohexanedione derivatives of the general formula (I-b1),

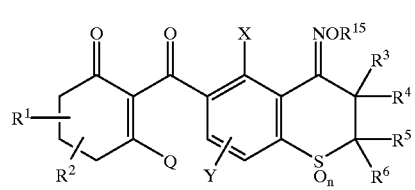
(I-b1)

wherein $R^1$ to $R^6$, n, X, Y and Q are as defined above, $R^{15}$ is a $C_1$~$C_6$ alkyl group or a $C_2$~$C_6$ alkenyl group, provided that when $R^{15}$ is a $C_1$~$C_6$ alkyl group, compounds of the general formula (I-b1) in which X is a $C_1$~$C_6$ alkyl group and all of $R^3$, $R^4$, $R^5$ and $R^6$ are hydrogen atoms are excluded, (6) cyclohexanedione derivatives of the general formula (I-b2), or salts thereof,

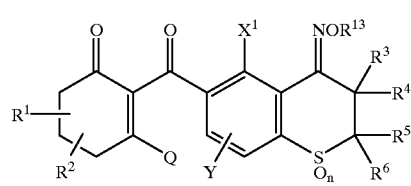
(I-b2)

wherein $R^1$ to $R^6$, $R^{13}$, n, $X^1$, Y and Q are as defined above, or (7) cyclohexanedione derivatives of the general formula (I-c), or salts thereof,

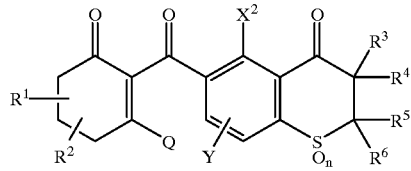
(I-c)

wherein $R^1$ to $R^6$, n, $X^2$, Y and Q are as defined above.

Further, the second object of the present invention is achieved by a herbicide (to be sometimes referred to as "herbicide of the present invention" hereinafter) containing, as active ingredient, at least one selected from the cyclohexanedione derivatives of the above general formulae (I), (I-a1), (I-a2), (I-a3), (I-b1), (I-b2) or (I-c) or salts thereof.

BEST MODE FOR PRACTICING THE INVENTION

The cyclohexanedione derivative of the present invention will be explained first.

The cyclohexanedione derivative of the present invention has the general formula (I).

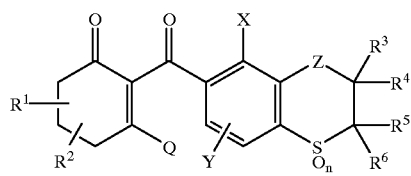
(I)

In the general formula (I), X is a $C_1$~$C_6$ alkyl group, a $C_1$~$C_6$ haloalkyl group, a halogen atom, a $C_1$~$C_6$ alkoxy group, a $C_1$~$C_6$ haloalkoxy group, a $C_2$~$C_6$ alkoxyalkyl group, a $C_1$~$C_6$ alkylthio group, a $C_1$~$C_6$ haloalkylthio group, a $C_1$~$C_6$ alkylsulfinyl group or a $C_1$~$C_6$ alkylsulfonyl group.

Examples of the above $C_1$~$C_6$ alkyl group include methyl, ethyl, propyl, butyl, pentyl and hexyl, and the propyl, butyl, pentyl and hexyl may be linear, cyclic or branched. The $C_1$~$C_6$ haloalkyl group is a group formed by replacing 1 to 13 hydrogen atoms of the above $C_1$~$C_6$ alkyl group with 1 to 13 halogen atoms (e.g., chlorine, flourine, bromine and iodine). Specific examples thereof include -$CF_3$, -$C_2F_5$, -$C_2H_4F$, -$CH_2Cl$, -$CHF_2$, -$CCl_3$, -$C_2H_3Cl_2$, -$C_2H_3F_2$, -$C_2H_2F_3$, -$C_2H_2Cl_3$, -$C_3H_6F$, -$C_4H_8F$, -$CH_2Br$, -$CH_2I$, -$C_3H_4F_3$ and -$C_4H_6F_3$. The halogen atom includes chlorine, fluorine, bromine and iodine.

Specific examples of the $C_1$~$C_6$ alkoxy group include methoxy, ethoxy, propoxy, butoxy, pentoxy and hexoxy, and the propoxy, butoxy, pentoxy and hexoxy may be linear, cyclic or branched. The $C_1$~$C_6$ haloalkoxy group is a group formed by replacing 1 to 13 hydrogen atoms of the above $C_1$~$C_6$ alkoxy group with 1 to 13 halogen atoms (e.g., chlorine, fluorine, bromine and iodine). Examples thereof include -$OCF_3$, -$OC_2F_5$, -$OC_2H_4F$, -$OC_2H_4Cl$, -$OCHF_2$, -$OCH_2F$, -$OCCl_3$, -$OC_2H_3Cl_2$, -$OC_2H_3F_2$, -$OCH_2Br$ and -$OCH_2I$.

The $C_2$~$C_6$ alkoxyalkyl group is a group formed by replacing one hydrogen atom of the above alkyl group with a $C_1$~$C_6$ alkoxy group (methoxy, ethoxy, n-propoxy, i-propoxy, n-butoxy, i-butoxy, s-butoxy, t-butoxy, n-hexoxy, i-hexoxy, s-hexoxy or t-hexoxy). Specific examples thereof include -$CH_2OCH_3$, -$CH_2OC_2H_5$, -$CH_2OC_3H_7$, -$C(CH_3)_2$ $OCH_3$, -$C(CH_2)_2OC_2H_5$, -$CH_2CH_2OCH_3$, -$CH_2CH_2OC_2H_5$, -$CH_2(CH_2)_2OCH_3$, -$CH_2C(CH_3)_2OCH_3$, -$CH_2CH_2CH_2OCH_3$ and -$CH(CH_3)CH_2OCH_3$.

Specific examples of the $C_1$~$C_6$ alkylthio group include methylthio, ethylthio, propylthio, butylthio, pentylthio and hexylthio, and the propylthio, butylthio, pentylthio and hexylthio may be linear, cyclic or branched. The $C_1$~$C_6$ haloalkylthio group is a group formed by replacing 1 to 13 hydrogen atoms of the above $C_1$~$C_4$ alkylthio group with 1 to 13 halogen atoms (e.g., chlorine, fluorine, bromine and iodine). Examples thereof include -$SCF_3$, -$SC_2F_5$, -$SC_2H_4F$, -$SC_2H_4Cl$, -$SCHF_2$, -$SCH_2F$, -$SCCl_3$, -$SC_2H_3Cl_2$, -$SC_2H_3F_2$, -$SCH_2Br$ and -$SCH_2I$.

Specific examples of the $C_1$~$C_6$ alkylsulfinyl group include methylsulfinyl, ethylsulfinyl, propylsulfinyl, butylsulfinyl, pentylsulfinyl and hexylsulfinyl, and the propylsulfinyl, butylsulfinyl, pentylsulfinyl and hexylsulfinyl may be linear, cyclic or branched. Examples of the $C_1$~$C_6$ alkylsulfonyl group include methylsulfonyl, ethylsulfonyl, propylsulfonyl, butylsulfonyl, pentylsulfonyl and hexylsulfonyl, and the propylsulfonyl, butylsulfonyl, pentylsulfonyl and hexylsulfonyl may be linear, cyclic or branched.

X is preferably a $C_1$~$C_6$ alkyl group, a $C_1$~$C_6$ haloalkyl group or a halogen atom, more preferably methyl, chlorine or -$CF_3$.

Y is a hydrogen atom, a $C_1$~$C_6$ alkyl group, a $C_1$~$C_6$ haloalkyl group, a halogen atom, a $C_1$~$C_6$ alkoxy group, a $C_1$~$C_6$ haloalkoxy group or a $C_2$~$C_6$ alkoxyalkyl group.

The above $C_1$~$C_6$ alkyl group, $C_1$~$C_6$ haloalkyl group, halogen atom, $C_1$~$C_6$ alkoxy group, $C_1$~$C_6$ haloalkoxy group or $C_2$~$C_6$ alkoxyalkyl group includes those specified with regard to the above X. The position of the substituent Y is the 7- or 8-position of the thiochroman ring, particularly preferably the 8-position. Y is preferably a hydrogen atom, a $C_1$~$C_6$ alkyl group or a halogen atom, particularly preferably hydrogen, methyl or chlorine.

Each of $R^1$ and $R^2$ is independently a hydrogen atom or a $C_1$~$C_6$ alkyl group, and each of $R^3$, $R^4$, $R^5$ and $R^6$ is independently a hydrogen atom, a $C_1$~$C_6$ alkyl group, a $C_1$~$C_6$ haloalkyl group or a halogen atom. Specific examples of the above $C_1$~$C_6$ alkyl groups, $C_1$~$C_6$ haloalkyl group and halogen atom are those specified with regard to X.

Each of $R^3$, $R^4$, $R^5$ and $R^6$ is independently preferably a hydrogen atom or a $C_1$~$C_6$ alkyl group such as methyl, particularly preferably a hydrogen atom or methyl.

n refers to the number of oxygen atom(s) bonding to the sulfur atom of the thiochroman ring, and it is 0 (sulfide), 1 (sulfoxide) or 2 (sulfone), preferably 0 (sulfide) or 2 (sulfone).

Z is a group of

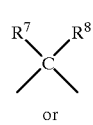

(a)

or

(b)

In the group (a) in the definition of Z, each of $R^7$ and $R^8$ is independently a hydrogen atom, a halogen atom, a $C_1$~$C_6$ alkyl group, a $C_1$~$C_6$ alkoxy group, a $C_1$~$C_6$ alkylthio group or a group of -$NR^{10}R^{11}$. When $R^7$ and/or $R^8$ are/is $C_1$~$C_6$ alkyl, $C_1$~$C_6$ alkoxy or $C_1$~$C_6$ alkylthio group(s), 1 to 13 hydrogen atoms of the group(s) may be replaced with 1 to 13 halogen atoms or $C_1$~$C_6$ alkoxy groups, and when the group(s) has/have 2 to 6 carbon atoms, the group(s) may contain an unsaturated bond. When the group(s) has/have 3 to 6 carbon atoms, the group(s) may contain a cyclic structure. Each of $R^{10}$ and $R^{11}$ is a hydrogen atom, a $C_1$~$C_6$ alkyl group or a $C_1$~$C_6$ alkylcarbonyl group. Further, when both $R^7$ and $R^8$ are $C_1$~$C_6$ alkyl groups, $C_1$~$C_6$ alkoxy groups or $C_1$~$C_6$ alkylthio groups, carbon atoms of $R^7$ and $R^8$ may form a 3- to 7-membered ring by bonding to each other.

However, when $R^7$ and $R^8$ are both alkyl groups, there is excluded a case where X is a $C_1$~$C_6$ alkyl group, a halogen atom or a haloalkyl group and all of $R^3$, $R^4$, $R^5$ and $R^6$ are hydrogen atoms.

Further, when one of $R^7$ and $R^8$ is an alkoxy group and when the other is a hydrogen atom, there is excluded a case where X is a $C_1$~$C_6$ alkyl group and all of $R^3$, $R^4$, $R^5$ and $R^6$ are hydrogen atoms when no hydrogen atom is replaced with halogen or alkoxy group or when the alkoxy group does not contain an unsaturated bond or a cyclic structure.

Specific examples of the halogen atom, $C_1$~$C_6$ alkyl group, $C_1$~$C_6$ alkoxy group and $C_1$~$C_6$ alkylthio group in the above $R^7$, $R^8$, $R^{10}$ and $R^{11}$ are those specified with regard to X. Examples of $C_1$~$C_6$ alkylcarbonyl group in the definition of $R^{10}$ and $R^{11}$ include acetyl, propionyl, butylyl and valeryl, and the butylyl and valeryl may be linear, cyclic or branched.

In the group (b) in the definition of Z, $R^9$ is an oxygen atom, a sulfur atom or a $C_1$~$C_6$ alkoxyimino group. When $R^9$ is a $C_1$~$C_6$ alkoxyimino group, 1 to 13 hydrogen atoms of the group may be replaced with 1 to 13 halogen atoms, and when the group has 2 to 4 carbon atoms, the group may contain an unsaturated bond. However, when $R^9$ is a $C_1$~$C_6$ alkoxyimino group, and when no hydrogen atom thereof is replaced with halogen or when the group contains no unsaturated bond, there is excluded a case where X is a $C_1$~$C_6$ alkyl group and all of $R^3$, $R^4$, $R^5$ and $R^6$ are hydrogen atoms. The alkoxyimino group is preferably methoxyimino or ethoxyimino.

Q is a hydroxyl group or a group of

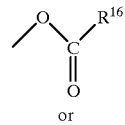

(c)

or

-continued (d)

In the groups (c) and (d) in the definition of Q, each of $R^{16}$ and $R^{17}$ is a $C_1$~$C_6$ alkyl group, a $C_1$~$C_6$ haloalkyl group or a phenyl group on which a $C_1$~$C_6$ alkyl group, a $C_1$~$C_6$ haloalkyl group, a halogen atom, a cyano group or a nitro group is substituted. Specific examples of the $C_1$~$C_6$ alkyl group and the $C_1$~$C_6$ haloalkyl group include those specified with regard to the above X. Further, on the phenyl group, 0 to 5 $C_1$~$C_6$ alkyl groups, $C_1$~$C_6$ haloalkyl groups, halogen atoms, cyano groups or nitro groups may be introduced, and the positions of these substituents may be 2-position to 6-positions. m is 0, 1 or 2, and m represents 0 (sulfide), 1 (sulfoxide) or 2 (sulfone).

Of the cyclohexanedione derivatives of the general formula (I), preferred are cyclohexanedione derivatives of the general formula (I-a1),

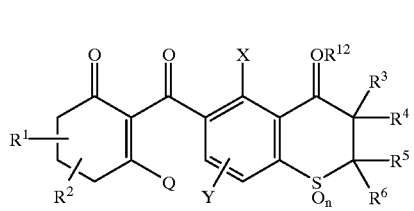

wherein $R^1$ to $R^6$, n, X, Y and Q are as defined above, and $R^{12}$ is a $C_1$~$C_6$ alkyl group or a $C_1$~$C_6$ haloalkyl group, $R^{12}$ may be substituted with $C_1$~$C_6$ alkoxy group(s), and when $R^{12}$ has 3 to 6 carbon atoms, it may contain a cyclic structure, provided that compounds of the general formula (I-a1) in which X is a $C_1$~$C_6$ alkyl group and all of $R^3$, $R^4$, $R^5$ and $R^6$ are hydrogen atoms when $R^{12}$ is a $C_1$~$C_6$ alkyl group are excluded.

Of the above cyclohexanedione derivatives, particularly preferred are cyclohexanedione derivatives of the general formula (I-a2),

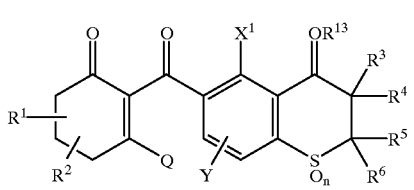

wherein $R^1$ to $R^6$, n, Y and Q are as defined above, $R^{13}$ is a $C_1$~$C_6$ alkyl group, and $X^1$ is a $C_1$~$C_6$ haloalkyl group, a halogen atom, a $C_1$~$C_6$ alkoxy group, a $C_1$~$C_6$ haloalkoxy group, a $C_2$~$C_6$ alkoxyalkyl group, a $C_1$~$C_6$ alkylthio group, a $C_1$~$C_6$ haloalkylthio group, a $C_1$~$C_6$ alkylsulfinyl group or a $C_1$~$C_6$ alkylsulfonyl group, and cyclohexanedione derivatives of the general formula (I-a3),

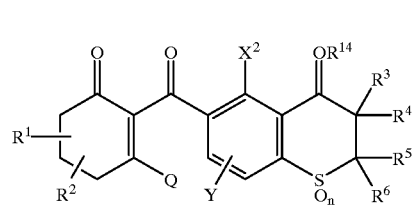

wherein $R^1$ to $R^6$, n, Y and Q are as defined above, $R^{14}$ is a $C_1$~$C_6$ haloalkyl group, an alkoxy alkyl group, an alkenyl group, a haloalkenylalkyl or an alkynylalkyl group, and $X^2$ is a $C_1$~$C_6$ alkyl group, a $C_1$~$C_6$ haloalkyl group, a halogen atom, a $C_1$~$C_6$ alkoxy group, a $C_1$~$C_6$ haloalkoxy group, a $C_2$~$C_6$ alkoxyalkyl group, a $C_1$~$C_6$ alkylthio group, a $C_1$~$C_6$ haloalkylthio group, a $C_1$~$C_6$ alkylsulfinyl group or a $C_1$~$C_6$ alkylsulfonyl group.

Further, preferred are cyclohexanedione derivatives of the general formula (I-b1),

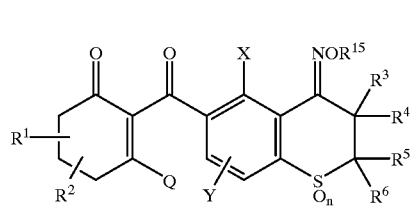

wherein $R^1$ to $R^6$, n, X, Y and Q are as defined above, $R^{15}$ is a $C_1$~$C_6$ alkyl group or a $C_2$~$C_6$ alkenyl group, provided that when $R^{15}$ is a $C_1$~$C_6$ alkyl group, there is excluded a case where X is a $C_1$~$C_6$ alkyl group and all of $R^3$, $R^4$, $R^5$ and $R^6$ are hydrogen atoms.

Of the above cyclohexanedione derivatives, particularly preferred are cyclohexanedione derivatives of the general formula (I-b2),

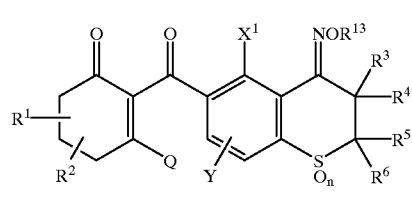

wherein $R^1$ to $R^6$, $R^{13}$, n, $X^1$, Y and Q are as defined above.

Further, preferred are also cyclohexanedione derivatives of the general formula (I-c),

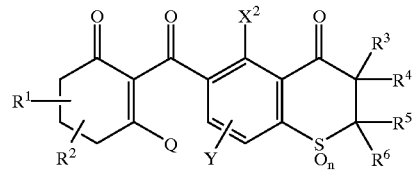

wherein $R^1$ to $R^6$, n, $X^2$, Y and Q are as defined above.

The cyclohexanedione derivatives of the general formula (I) can have the following structures of tautomerism when Q is a hydroxy group, and the cyclohexanedione derivative of the present invention includes all the compounds having these structures and mixtures of these.

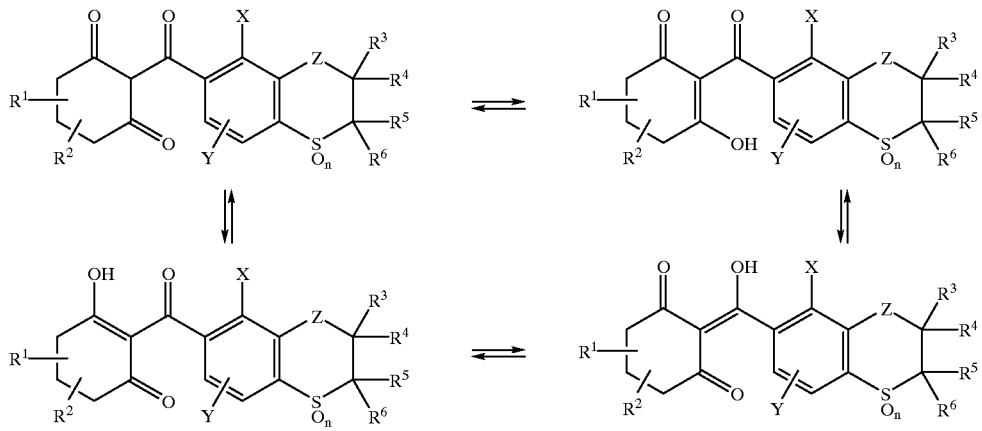

wherein X, Y, Z, $R^1$, $R^2$, $R^3$, $R^4$, $R^5$, $R^6$ and n are as defined above.

Further, the cyclohexanedione derivatives of the general formula (I) are acidic materials, and can be easily converted to salts by treating them with a base. The cyclohexanedione derivative of the present invention includes these salts.

The above base can be selected from known bases without any limitation, and examples of the base include organic bases such as amines and anilines and inorganic bases such as sodium compounds and potassium compounds. Examples of the amines include alkylamines such as monoalkylamine, dialkylamine and trialkylamine. Alkyl groups of the alkylamines are generally $C_1$~$C_4$ alkyl groups. Examples of the anilines include aniline and alkylanilines such as monoalkylaniline and dialkylaniline. Alkyl groups of the alkylanilines are generally $C_1$~$C_4$ alkyl groups. Examples of the sodium compounds include sodium hydroxide and sodium carbonate. Examples of the potassium compounds include potassium hydroxide and potassium carbonate.

The cyclohexanedione derivatives of the general formula (I) can be produced, for example, by the following method when Q is -OH [general formula (I-OH)].

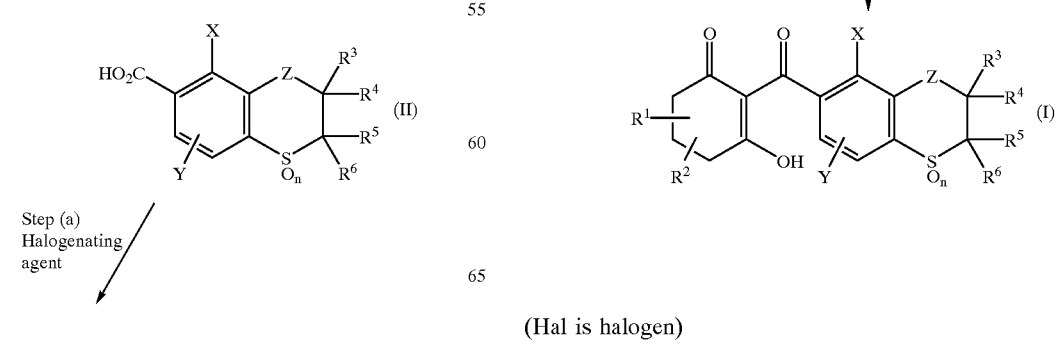

(Hal is halogen)

wherein X, Y, Z, $R^1$, $R^2$, $R^3$, $R^4$, $R^5$, $R^6$ and n are as defined above.

That is, Compound of the general formula (II) is reacted with a halogenating agent to obtain Compound of the general formula (III), and then the Compound of the general formula (III) is reacted with Compound of the general formula (IV) to obtain Compound of the general formula (V). Then, the Compound of the general formula (V) is subjected to a rearrangement reaction to obtain Cyclohexanedione derivative of the general formula (I-OH).

Further, Compound of the general formula (V) can be obtained by reacting Compound of the general formula (II) with Compound of the general formula (IV) in the presence of a dehydrating agent such as dicyclohexylcarbodiimide (to be referred to as "DCC" hereinafter).

Each step will be explained hereinafter.

Step (a)

In step (a), Compound of the general formula (II) is reacted with a halogenating agent (thionyl chloride or phosphorus oxychloride) to obtain Compound of the general formula (III). In step (a), preferably, a halogenating agent is used in an amount of 1 mol or more per mole of Compound of the general formula (II). The reaction may be carried out in a diluted state in an inert solvent (methylene chloride or chloroform) or without any solvent. Further, an excess of thionyl chloride as a halogenating agent may be used to work it as a solvent. Although not specially limited, the reaction temperature is preferably 0° C. to the boiling point of the solvent, particularly preferably a temperature of 60° C. or around it.

Step (b)

In step (b), Compound of the general formula (III) obtained in step (a) is reacted with Compound of the general formula (IV) to obtain Compound of the general formula (V). In step (b), preferably, the molar ratio of Compound of the general formula (III)/Compound of the general formula (IV) is preferably approximately 1/1 to 1/3, and the reaction is carried out in an inert solvent such as dioxane, acetonitrile, benzene, toluene, chloroform, methylene chloride or 1,2-dichloroethane. Further, the reaction may be carried out in a solvent of two-phase system such as water-benzene, water-toluene or water-chloroform. When a base such as sodium hydroxide, potassium hydroxide, sodium carbonate, potassium carbonate, triethylamine or pyridine is present in an equimolar amount or more, the reaction proceeds smoothly. The reaction temperature is preferably 0° C. to 60° C., particularly preferably in the range of from 0° C. to room temperature.

Step (c)

In step (c), Compound of the general formula (V) obtained in step (b) is subjected to a rearrangement reaction to obtain Cyclohexanedione derivative of the general formula (I-OH). In step (c), preferably, the reaction is carried out in an inert solvent such as methylene chloride, 1,2-dichloroethane, toluene, acetonitrile, N,N-dimethylformamide or ethyl acetate. Acetonitrile is particularly preferred. In step (c), a proper base (sodium carbonate, potassium carbonate, triethylamine or pyridine) is used in an amount of, generally, 1 to 4 equivalent weights, preferably 1 to 2 equivalent weight, per equivalent weight of Compound of the general formula (V). In this case, the reaction smoothly proceeds in the catalytic presence of hydrogen cyanide or a compound which can generate cyanide anion in the reaction system, a so-called "cyanide source". The cyanide source is selected, for example, from metal cyanides such as sodium cyanide and potassium cyanide and cyanhydrin compounds of lower alkyl ($C_3 \sim C_6$) ketones such as acetonecyanhyrdin and methylisopropylketonecyanhydrin. When the metal cyanide is used, the reaction can be smoothly proceeded with by adding a phase transfer catalyst such as a crown ether during the reaction. The amount of the cyanide source per mole of Compound of the general formula (V) is generally 0.01 to 0.5 mol, preferably 0.05 to 0.2 mol. The reaction temperature is preferably 0 to 80° C., particularly preferably 20 to 40° C.

Step (d)

Step (d) shows a method for obtaining Compound of the general formula (V), which method is different from the above method. That is, in step (d), Compound (V) is obtained from Compound (II) and Compound (IV) by condensation in the presence of a dehydrating agent such as DCC. Although not specially limited, the reaction solvent used for the above condensation is preferably selected from acetonitrile, a tertiary amine or an alcohol. The reaction temperature is not specially limited so long as it is in the range of from 0° C. to the boiling point of the solvent, while the reaction temperature is preferably room temperature. The dehydrating agent can be selected from the above DCC or other agent such as 1,1-carbonyldiimidazole (CDI) or 1-(3-dimethylaminopropyl)-3-ethylcarbodiimide (EDC). The amount of the dehydrating agent based on Compound is generally 1.0 to 3.0 molar equivalent, preferably 1.0 to 1.5 molar equivalent. The molar ratio of Compound (II)/Compound (IV) is generally 1/1 to 1/3, preferably 1/1 to 1/1.5. It is sufficient to carry out the condensation of Compound (II) and Compound (IV) for 1 to 48 hours, and the condensation is generally completed for about 8 hours.

Tables 1 to 19 show preferred embodiments of the cyclohexanedione derivatives of the general formula (I-OH) of the present invention, obtained as described above.

TABLE 1

[In the general formula (I), Q = OH, $R^1 = R^2 = R^5 = R^6$ = H and n = 2]

| Comp'd No. | $R^3$ | $R^4$ | X | Y | Z |
|---|---|---|---|---|---|
| 1 | H | H | Cl | 8-F | NOCH$_3$ group |
| 2 | H | H | Cl | 8-F | OCH$_2$CH$_2$F group |
| 3 | H | H | Cl | 8-CH$_3$ | OCH$_3$ group |

TABLE 1-continued

[In the general formula (I),
Q = OH, $R^1 = R^2 = R^5 = R^6 = H$ and n = 2]

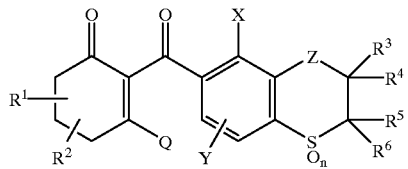

| Comp'd No. | $R^3$ | $R^4$ | X | Y | Z |
|---|---|---|---|---|---|
| 4 | $CH_3$ | $CH_3$ | $CF_3$ | 8-$CH_3$ | ![acetone] |
| 5 | $CH_3$ | $CH_3$ | $CH_3$ | 8-$CH_3$ | ![acetone] |

TABLE 2

[In the general formula (I-a2),
Q = OH, $R_1 = R^2 = R^3 = R^4 = R^5 = R^6 = H$
and n = 2]

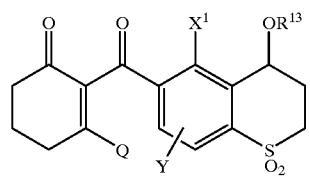

| Comp'd No. | $X^1$ | Y | $R^{13}$ |
|---|---|---|---|
| 6 | Cl | H | —$CH_3$ |
| 7 | Cl | H | —$C_2H_5$ |
| 8 | Cl | H | -n-$C_3H_7$ |
| 9 | Cl | H | -i-$C_3H_7$ |
| 10 | Cl | H | -s-$C_4H_9$ |
| 11 | Cl | H | -i-$C_4H_9$ |
| 12 | Cl | H | -t-$C_4H_9$ |
| 13 | Cl | 8-$CH_3$ | —$C_2H_5$ |
| 14 | Cl | 8-$CH_3$ | -n-$C_3H_7$ |
| 15 | Cl | 8-$CH_3$ | -i-$C_3H_7$ |
| 16 | Cl | 8-$CH_3$ | -s-$C_4H_9$ |
| 17 | Cl | 8-$CH_3$ | -i-$C_4H_9$ |
| 18 | Cl | 8-$CH_3$ | -t-$C_4H_9$ |

TABLE 3

[In the general formula (I-a2),
Q = OH, $R^1 = R^2 = R^3 = R^4 = R^5 = R^6 = H$
and n = 2]

| Comp'd No. | $X^1$ | Y | $R^{13}$ |
|---|---|---|---|
| 19 | Cl | 8-F | —$CH_3$ |
| 20 | Cl | 8-F | —$C_2H_5$ |
| 21 | Cl | 8-F | -n-$C_3H_7$ |
| 22 | Cl | 8-F | -i-$C_3H_7$ |
| 23 | Cl | 8-F | -s-$C_4H_9$ |
| 24 | Cl | 8-F | -i-$C_4H_9$ |
| 25 | Cl | 8-F | -t-$C_4H_9$ |
| 26 | Cl | 8-Cl | —$CH_3$ |
| 27 | Cl | 8-Cl | —$C_2H_5$ |
| 28 | Cl | 8-Cl | -n-$C_3H_7$ |
| 29 | Cl | 8-Cl | -i-$C_3H_7$ |
| 30 | Cl | 8-Cl | -s-$C_4H_9$ |
| 31 | Cl | 8-Cl | -i-$C_4H_9$ |
| 32 | Cl | 8-Cl | -t-$C_4H_9$ |

TABLE 4

[In the general formula (I-a2),
Q = OH, each of $R^1$ and $R^2$ is
methyl and bonds to
the 4-position of cyclohexanedione ring,
$R^3 = R^4 = R^5 = R^6 = H$, and n = 2.]

| Comp'd No. | $X^1$ | Y | $R^{13}$ |
|---|---|---|---|
| 33 | Cl | H | —$CH_3$ |
| 34 | Cl | H | —$C_2H_5$ |
| 35 | Cl | H | -n-$C_3H_7$ |
| 36 | Cl | H | -i-$C_3H_7$ |
| 37 | Cl | H | -s-$C_4H_9$ |
| 38 | Cl | H | -i-$C_4H_9$ |
| 39 | Cl | H | -t-$C_4H_9$ |
| 40 | Cl | 8-$CH_3$ | —$CH_3$ |
| 41 | Cl | 8-$CH_3$ | —$C_2H_5$ |
| 42 | Cl | 8-$CH_3$ | -n-$C_3H_7$ |
| 43 | Cl | 8-$CH_3$ | -i-$C_3H_7$ |
| 44 | Cl | 8-$CH_3$ | -s-$C_4H_9$ |
| 45 | Cl | 8-$CH_3$ | -i-$C_4H_9$ |
| 46 | Cl | 8-$CH_3$ | -t-$C_4H_9$ |

TABLE 5

[In the general formula (I-a2),
Q = OH, each of $R^1$ and $R^2$ is
methyl and bonds to
the 4-position of cyclohexanedione ring,
$R^3 = R^4 = R^5 = R^6 = H$, and n = 2.]

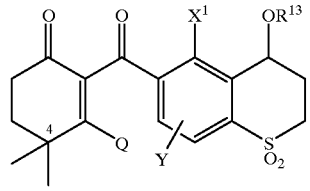

| Comp'd No. | $X^1$ | Y | $R^{13}$ |
|---|---|---|---|
| 47 | Cl | 8-F | —CH₃ |
| 48 | Cl | 8-F | —C₂H₅ |
| 49 | Cl | 8-F | -n-C₃H₇ |
| 50 | Cl | 8-F | -i-C₃H₇ |
| 51 | Cl | 8-F | -s-C₄H₉ |
| 52 | Cl | 8-F | -i-C₄H₉ |
| 53 | Cl | 8-F | -t-C₄H₉ |
| 54 | Cl | 8-Cl | —CH₃ |
| 55 | Cl | 8-Cl | —C₂H₅ |
| 56 | Cl | 8-Cl | -n-C₃H₇ |
| 57 | Cl | 8-Cl | -i-C₃H₇ |
| 58 | Cl | 8-Cl | -s-C₄H₉ |
| 59 | Cl | 8-Cl | -i-C₄H₉ |
| 60 | Cl | 8-Cl | -t-C₄H₉ |

TABLE 6

[In the general formula (I-a2),
Q = OH, each of $R^1$ and $R^2$ is
methyl and bonds to the 5-position of
cyclohexanedione ring,
$R^3 = R^4 = R^5 = R^6 = H$, and n = 2.]

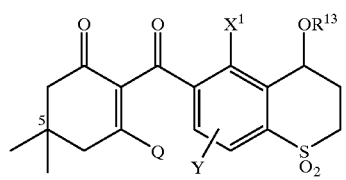

| Comp'd No. | $X^1$ | Y | $R^{13}$ |
|---|---|---|---|
| 61 | Cl | H | —CH₃ |
| 62 | Cl | H | —C₂H₅ |
| 63 | Cl | H | -n-C₃H₇ |
| 64 | Cl | H | -i-C₃H₇ |
| 65 | Cl | H | -s-C₄H₉ |
| 66 | Cl | H | -i-C₄H₉ |
| 67 | Cl | H | -t-C₄H₉ |
| 68 | Cl | 8-CH₃ | —CH₃ |
| 69 | Cl | 8-CH₃ | —C₂H₅ |
| 70 | Cl | 8-CH₃ | -n-C₃H₇ |
| 71 | Cl | 8-CH₃ | -i-C₃H₇ |
| 72 | Cl | 8-CH₃ | -s-C₄H₉ |
| 73 | Cl | 8-CH₃ | -i-C₄H₉ |
| 74 | Cl | 8-CH₃ | -t-C₄H₉ |

TABLE 7

[In the general formula (I-a2),
Q = OH, each of $R^1$ and $R^2$ is
methyl and bonds to the 5-position of
cyclohexanedione ring,
$R^3 = R^4 = R^5 = R^6 = H$, and n = 2.]

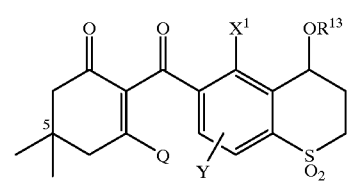

| Comp'd No. | $X^1$ | Y | $R^{13}$ |
|---|---|---|---|
| 75 | Cl | 8-F | —CH₃ |
| 76 | Cl | 8-F | —C₂H₅ |
| 77 | Cl | 8-F | -n-C₃H₇ |
| 78 | Cl | 8-F | -i-C₃H₇ |
| 79 | Cl | 8-F | -s-C₄H₉ |
| 80 | Cl | 8-F | -i-C₄H₉ |
| 81 | Cl | 8-F | -t-C₄H₉ |
| 82 | Cl | 8-Cl | —CH₃ |
| 83 | Cl | 8-Cl | —C₂H₅ |
| 84 | Cl | 8-Cl | -n-C₃H₇ |
| 85 | Cl | 8-Cl | -i-C₃H₇ |
| 86 | Cl | 8-Cl | -s-C₄H₉ |
| 87 | Cl | 8-Cl | -i-C₄H₉ |
| 88 | Cl | 8-Cl | -t-C₄H₉ |

TABLE 8

[In the general formula (I-a3),
Q = OH, $R^1 = R^2 = R^3 = R^4 = R^5 = R^6 = H$,
and n = 2.]

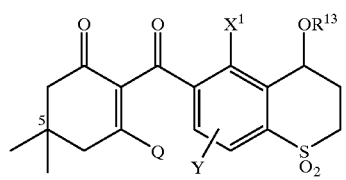

| Comp'd No. | $X^2$ | Y | $R^{14}$ |
|---|---|---|---|
| 89 | CH₃ | H | —CH₂CH₂F |
| 90 | CH₃ | H | —CH₂CHF₂ |
| 91 | CH₃ | H | —CH₂CF₃ |
| 92 | CH₃ | H | —CH₂CH₂CH₂F |
| 93 | CH₃ | H | —CH₂CH₂Cl |
| 94 | CH₃ | 8-CH₃ | —CH₂CH₂F |
| 95 | CH₃ | 8-CH₃ | —CH₂CHF₂ |
| 96 | CH₃ | 8-CH₃ | —CH₂CF₃ |
| 97 | CH₃ | 8-CH₃ | —CH₂CH₂CH₂F |
| 98 | CH₃ | 8-CH₃ | —CH₂CH₂Cl |
| 99 | Cl | H | —CH₂CH₂F |
| 100 | Cl | H | —CH₂CHF₂ |
| 101 | Cl | H | —CH₂CF₃ |
| 102 | Cl | H | —CH₂CH₂CH₂F |
| 103 | Cl | H | —CH₂CH₂Cl |

TABLE 9

[In the general formula (I-a3),
Q = OH, $R^1 = R^2 = R^3 = R^4 = R^5 = R^6 = H$,
and n = 2.]

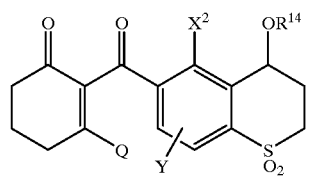

| Comp'd No. | $X^2$ | Y | $R^{14}$ |
|---|---|---|---|
| 104 | Cl | 8-$CH_3$ | —$CH_2CH_2F$ |
| 105 | Cl | 8-$CH_3$ | —$CH_2CHF_2$ |
| 106 | Cl | 8-$CH_3$ | —$CH_2CF_3$ |
| 107 | Cl | 8-$CH_3$ | —$CH_2CH_2CH_2F$ |
| 108 | Cl | 8-$CH_3$ | —$CH_2CH_2Cl$ |
| 109 | Cl | 8-Cl | —$CH_2CH_2F$ |
| 110 | Cl | 8-Cl | —$CH_2CHF_2$ |
| 111 | Cl | 8-Cl | —$CH_2CF_3$ |
| 112 | Cl | 8-Cl | —$CH_2CH_2CH_2F$ |
| 113 | Cl | 8-Cl | —$CH_2CH_2Cl$ |

TABLE 10

[In the general formula (I-a3),
Q = OH, each of $R^1$ and $R^2$ is
methyl and bonds to the 4-position of
cyclohexanedione ring,
$R^3 = R^4 = R^5 = R^6 = H$ and n = 2.]

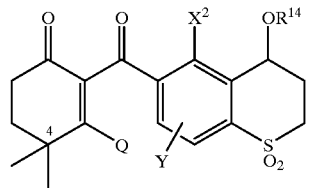

| Comp'd No. | $X^2$ | Y | $R^{14}$ |
|---|---|---|---|
| 114 | $CH_3$ | H | —$CH_2CH_2F$ |
| 115 | $CH_3$ | H | —$CH_2CHF_2$ |
| 116 | $CH_3$ | H | —$CH_2CF_3$ |
| 117 | $CH_3$ | H | —$CH_2CH_2CH_2F$ |
| 118 | $CH_3$ | H | —$CH_2CH_2Cl$ |
| 119 | $CH_3$ | 8-$CH_3$ | —$CH_2CH_2F$ |
| 120 | $CH_3$ | 8-$CH_3$ | —$CH_2CHF_2$ |
| 121 | $CH_3$ | 8-$CH_3$ | —$CH_2CF_3$ |
| 122 | $CH_3$ | 8-$CH_3$ | —$CH_2CH_2CH_2F$ |
| 123 | $CH_3$ | 8-$CH_3$ | —$CH_2CH_2Cl$ |
| 124 | Cl | H | —$CH_2CH_2F$ |
| 125 | Cl | H | —$CH_2CHF_2$ |
| 126 | Cl | H | —$CH_2CF_3$ |
| 127 | Cl | H | —$CH_2CH_2CH_2F$ |
| 128 | Cl | H | —$CH_2CH_2Cl$ |

TABLE 11

[In the general formula (I-a3),
Q = OH, each of $R^1$ and $R^2$ is
methyl and bonds to the 4-position of
cyclohexanedione ring,
$R^3 = R^4 = R^5 = R^6 = H$ and n = 2.]

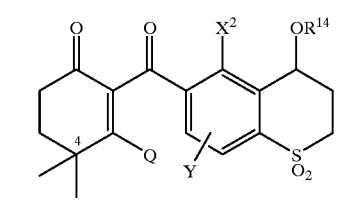

| Comp'd No. | $X^2$ | Y | $R^{14}$ |
|---|---|---|---|
| 129 | Cl | 8-$CH_3$ | —$CH_2CH_2F$ |
| 130 | Cl | 8-$CH_3$ | —$CH_2CHF_2$ |
| 131 | Cl | 8-$CH_3$ | —$CH_2CF_3$ |
| 132 | Cl | 8-$CH_3$ | —$CH_2CH_2CH_2F$ |
| 133 | Cl | 8-$CH_3$ | —$CH_2CH_2Cl$ |
| 134 | Cl | 8-Cl | —$CH_2CH_2F$ |
| 135 | Cl | 8-Cl | —$CH_2CHF_2$ |
| 136 | Cl | 8-Cl | —$CH_2CF_3$ |
| 137 | Cl | 8-Cl | —$CH_2CH_2CH_2F$ |
| 138 | Cl | 8-Cl | —$CH_2CH_2Cl$ |

TABLE 12

[In the general formula (I-a3),
Q = OH, each of $R^1$ and $R^2$ is
methyl and bonds to the 5-position of
cyclohexanedione ring,
$R^3 = R^4 = R^5 = R^6 = H$ and n = 2.]

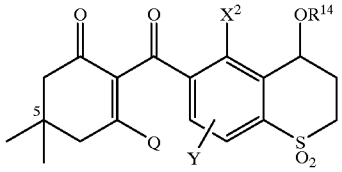

| Comp'd No. | $X^2$ | Y | $R^{14}$ |
|---|---|---|---|
| 139 | $CH_3$ | H | —$CH_2CH_2F$ |
| 140 | $CH_3$ | H | —$CH_2CHF_2$ |
| 141 | $CH_3$ | H | —$CH_2CF_3$ |
| 142 | $CH_3$ | H | —$CH_2CH_2CH_2F$ |
| 143 | $CH_3$ | H | —$CH_2CH_2Cl$ |
| 145 | $CH_3$ | 8-$CH_3$ | —$CH_2CH_2F$ |
| 146 | $CH_3$ | 8-$CH_3$ | —$CH_2CHF_2$ |
| 147 | $CH_3$ | 8-$CH_3$ | —$CH_2CF_3$ |
| 148 | $CH_3$ | 8-$CH_3$ | —$CH_2CH_2CH_2F$ |
| 149 | $CH_3$ | 8-$CH_3$ | —$CH_2CH_2Cl$ |
| 150 | Cl | H | —$CH_2CH_2F$ |
| 151 | Cl | H | —$CH_2CHF_2$ |
| 152 | Cl | H | —$CH_2CF_3$ |
| 153 | Cl | H | —$CH_2CH_2CH_2F$ |
| 154 | Cl | H | —$CH_2CH_2Cl$ |

TABLE 13

[In the general formula (I-a3),
Q = OH, each of $R^1$ and $R^2$ is
methyl and bonds to the 5-position of
cyclohexanedione ring,
$R^3 = R^4 = R^5 = R^6$ = H and n = 2.]

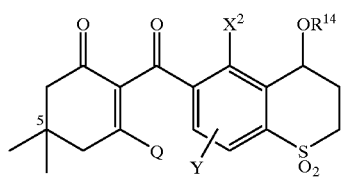

| Comp'd No. | $X^2$ | Y | $R^{14}$ |
|---|---|---|---|
| 155 | Cl | 8-$CH_3$ | —$CH_2CH_2F$ |
| 156 | Cl | 8-$CH_3$ | —$CH_2CHF_2$ |
| 157 | Cl | 8-$CH_3$ | —$CH_2CF_3$ |
| 158 | Cl | 8-$CH_3$ | —$CH_2CH_2CH_2F$ |
| 159 | Cl | 8-$CH_3$ | —$CH_2CH_2Cl$ |
| 160 | Cl | 8-Cl | —$CH_2CH_2F$ |
| 161 | Cl | 8-Cl | —$CH_2CHF_2$ |
| 162 | Cl | 8-Cl | —$CH_2CF_3$ |
| 163 | Cl | 8-Cl | —$CH_2CH_2CH_2F$ |
| 164 | Cl | 8-Cl | —$CH_2CH_2Cl$ |

TABLE 14

[In the general formula (I-b2),
Q = OH, $R^1 = R^2 = R^3 = R^4 = R^5 = R^6$ = H
and n = 2.]

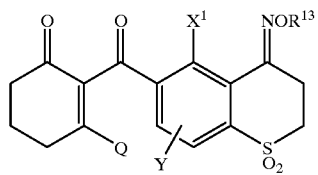

| Comp'd No. | $X^1$ | Y | $R^{13}$ |
|---|---|---|---|
| 165 | Cl | H | —$CH_3$ |
| 166 | Cl | H | —$C_2H_5$ |
| 167 | Cl | H | -i-$C_3H_7$ |
| 168 | Cl | 8-$CH_3$ | —$CH_3$ |
| 169 | Cl | 8-$CH_3$ | —$C_2H_5$ |
| 170 | Cl | 8-$CH_3$ | -i-$C_3H_7$ |
| 171 | Cl | 8-F | —$C_2H_5$ |
| 172 | Cl | 8-F | -i-$C_3H_7$ |
| 173 | Cl | 8-Cl | —$CH_3$ |
| 174 | Cl | 8-Cl | —$C_2H_5$ |
| 175 | Cl | 8-Cl | -i-$C_3H_7$ |

TABLE 15

[In the general formula (I-b2),
Q = OH, each of $R^1$ and $R^2$ is
methyl and bonds to the 4-position of
cyclohexanedione ring,
$R^3 = R^4 = R^5 = R^6$ = H and n = 2.]

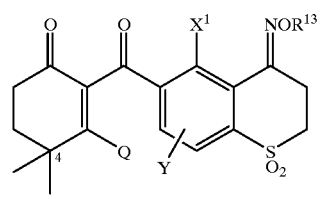

| Comp'd No. | $X^1$ | Y | $R^{13}$ |
|---|---|---|---|
| 176 | Cl | H | —$CH_3$ |
| 177 | Cl | H | —$C_2H_5$ |
| 178 | Cl | H | -i-$C_3H_7$ |
| 179 | Cl | 8-$CH_3$ | —$CH_3$ |
| 180 | Cl | 8-$CH_3$ | —$C_2H_5$ |
| 181 | Cl | 8-$CH_3$ | -i-$C_3H_7$ |
| 182 | Cl | 8-F | —$CH_3$ |
| 183 | Cl | 8-F | —$C_2H_5$ |
| 184 | Cl | 8-F | -i-$C_3H_7$ |
| 185 | Cl | 8-Cl | —$CH_3$ |
| 186 | Cl | 8-Cl | —$C_2H_5$ |
| 189 | Cl | 8-Cl | -i-$C_3H_7$ |

TABLE 16

[In the general formula (I-b2),
Q = OH, each of $R^1$ and $R^2$ is
methyl and bonds to the 5-position of
cyclohexanedione ring,
$R^3 = R^4 = R^5 = R^6$ = H and n = 2.]

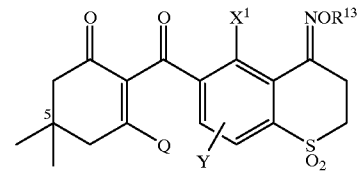

| Comp'd No. | $X^1$ | Y | $R^{13}$ |
|---|---|---|---|
| 190 | Cl | H | —$CH_3$ |
| 191 | Cl | H | —$C_2H_5$ |
| 192 | Cl | H | -i-$C_3H_7$ |
| 193 | Cl | 8-$CH_3$ | —$CH_3$ |
| 194 | Cl | 8-$CH_3$ | —$C_2H_5$ |
| 195 | Cl | 8-$CH_3$ | -i-$C_3H_7$ |
| 196 | Cl | 8-F | —$CH_3$ |
| 197 | Cl | 8-F | —$C_2H_5$ |
| 198 | Cl | 8-F | -i-$C_3H_7$ |
| 199 | Cl | 8-Cl | —$CH_3$ |
| 200 | Cl | 8-Cl | —$C_2H_5$ |
| 201 | Cl | 8-Cl | -i-$C_3H_7$ |

TABLE 17

[In the general formula (I-c),
Q = OH, $R^3 = R^4 = CH_3$,
$R^1 = R^2 = R^5 = R^6$ = H, and n = 2.]

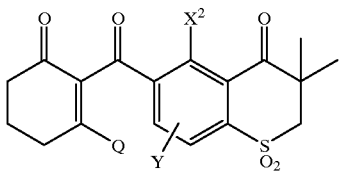

| Comp'd No. | $X^2$ | Y |
| --- | --- | --- |
| 202 | $CH_3$ | H |
| 203 | Cl | H |
| 204 | Cl | 8-$CH_3$ |
| 205 | Cl | 8-Cl |

TABLE 18

[In the general formula (I-c),
Q = OH, each of $R^1$ and $R^2$ is
methyl and bonds to the 4-position of
cyclohexanedione ring,
$R^3 = R^4 = CH_3$, $R^5 = R^6$ = H and n = 2.]

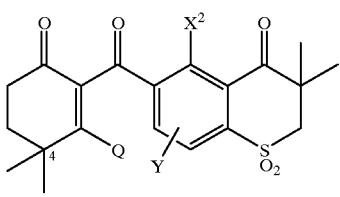

| Comp'd No. | $X^2$ | Y |
| --- | --- | --- |
| 206 | $CH_3$ | H |
| 207 | $CH_3$ | 8-$CH_3$ |
| 208 | Cl | H |
| 209 | Cl | 8-$CH_3$ |
| 210 | Cl | 8-Cl |

TABLE 19

[In the general formula (I-c),
Q = OH, each of $R^1$ and $R^2$ is
methyl and bonds to the 5-position of
cyclohexanedione ring,
$R^3 = R^4 = CH_3$, $R^5 = R^6$ = H and n = 2.]

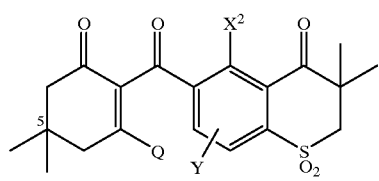

| Comp'd No. | $X^2$ | Y |
| --- | --- | --- |
| 211 | $CH_3$ | H |
| 212 | $CH_3$ | 8-$CH_3$ |
| 213 | Cl | H |

TABLE 19-continued

[In the general formula (I-c),
Q = OH, each of $R^1$ and $R^2$ is
methyl and bonds to the 5-position of
cyclohexanedione ring,
$R^3 = R^4 = CH_3$, $R^5 = R^6$ = H and n = 2.]

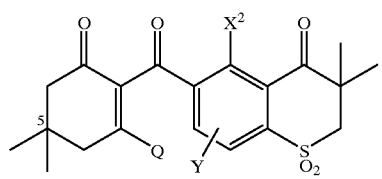

| Comp'd No. | $X^2$ | Y |
| --- | --- | --- |
| 214 | Cl | 8-$CH_3$ |
| 215 | Cl | 8-Cl |

TABLE 20

In the general formula (I),
Q = OH, $R_1 = R_2 = R_3 = R_4 = R_5 = R_6$ = H,
and n = 2

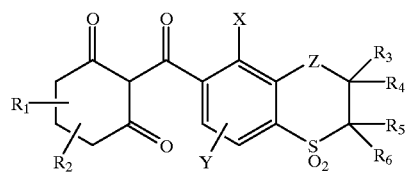

| Comp'd No. | X | Y | Z |
| --- | --- | --- | --- |
| 216 | —$CH_3$ | 8-$CH_3$ | 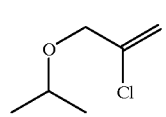 |
| 217 | —$CH_3$ | 8-$CH_3$ | |
| 218 | —$CH_3$ | 8-$CH_3$ | |
| 219 | —$CH_3$ | 8-$CH_3$ | 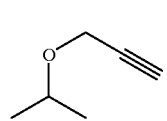 |

TABLE 20-continued
In the general formula (I),
$Q = OH$, $R_1 = R_2 = R_3 = R_4 = R_5 = R_6 = H$,
and $n = 2$
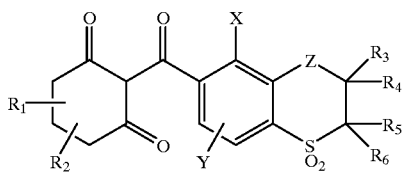
| Comp'd No. | X | Y | Z |
|---|---|---|---|
| 220 | —CH$_3$ | 8-CH$_3$ | |
| 221 | —CH$_3$ | 8-CH$_3$ | |
| 222 | —CH$_3$ | 8-CH$_3$ | |
| 223 | —CH$_3$ | 8-CH$_3$ | |
| 224 | —CH$_3$ | 8-CH$_3$ | |
TABLE 21
In the general formula (I),
$Q = OH$, $R_1 = R_2 = R_3 = R_4 = R_5 = R_6 = H$,
and $n = 2$
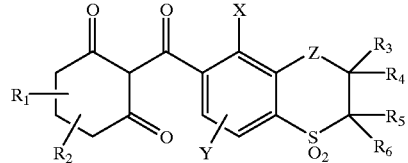
| Comp'd No. | X | Y | Z |
|---|---|---|---|
| 225 | —CH$_3$ | 8-CH$_3$ | |
| 226 | —CH$_3$ | 8-CH$_3$ | |
| 227 | —CH$_3$ | H | |
| 228 | —CH$_3$ | H | |
| 229 | —CH$_3$ | H | |
| 230 | —CH$_3$ | H | |
| 231 | —CH$_3$ | H | |

TABLE 21-continued

In the general formula (I),
Q = OH, R$_1$ = R$_2$ = R$_3$ = R$_4$ = R$_5$ = R$_6$ = H,
and n = 2

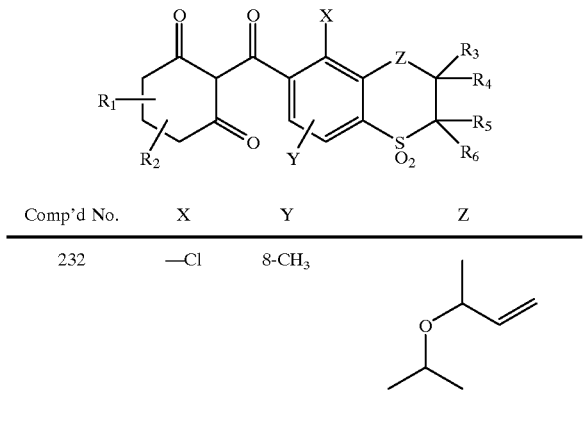

| Comp'd No. | X | Y | Z |
|---|---|---|---|
| 232 | —Cl | 8-CH$_3$ | (1-isopropoxyethyl-vinyl) |

TABLE 22

In the general formula (I),
Q = OH, R$_1$ = R$_2$ = R$_3$ = R$_4$ = R$_5$ = R$_6$ = H,
and n = 2

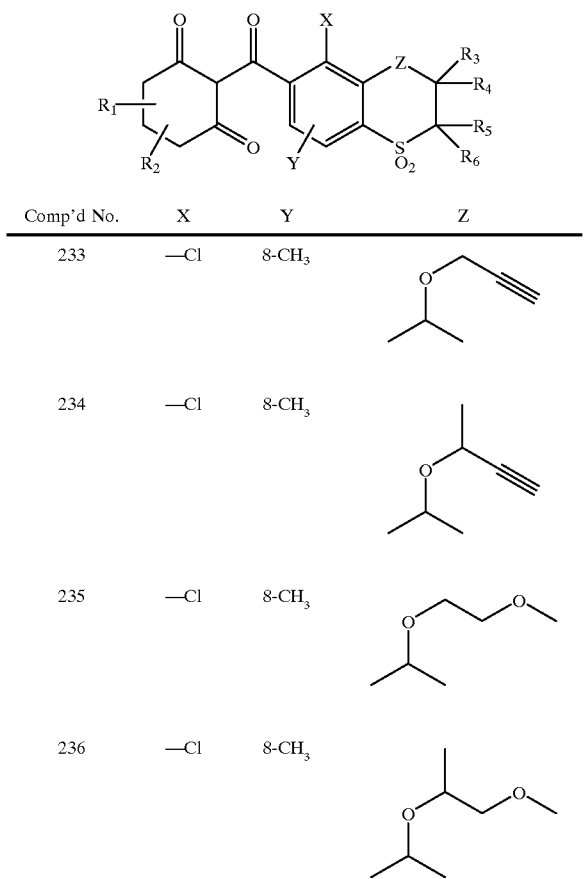

| Comp'd No. | X | Y | Z |
|---|---|---|---|
| 233 | —Cl | 8-CH$_3$ | (isopropoxymethyl-propargyl) |
| 234 | —Cl | 8-CH$_3$ | (1-isopropoxyethyl-propargyl) |
| 235 | —Cl | 8-CH$_3$ | (isopropoxyethyl methyl ether) |
| 236 | —Cl | 8-CH$_3$ | (1-isopropoxy-3-methoxy-propan-2-yl) |

TABLE 22-continued

In the general formula (I),
Q = OH, R$_1$ = R$_2$ = R$_3$ = R$_4$ = R$_5$ = R$_6$ = H,
and n = 2

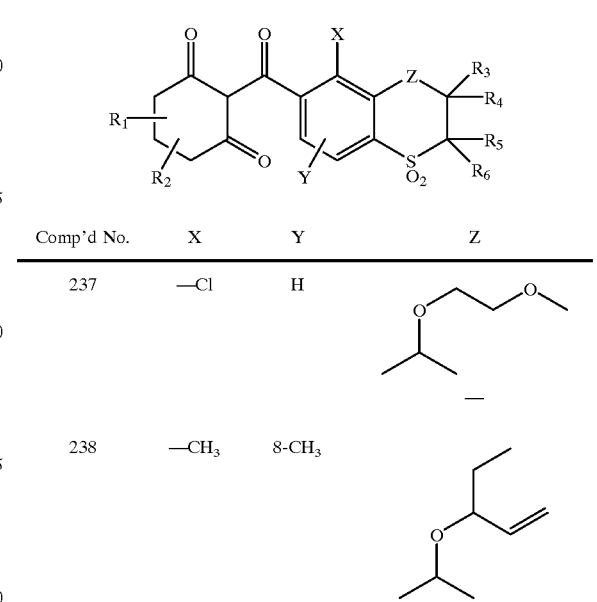

| Comp'd No. | X | Y | Z |
|---|---|---|---|
| 237 | —Cl | H | (isopropoxyethyl methyl ether) |
| 238 | —CH$_3$ | 8-CH$_3$ | (1-isopropoxy-pent-1-en-3-yl) |
| 239 | —CH$_3$ | 8-CH$_3$ | (isopropoxymethyl-tetrahydrofuran) |
| 240 | —CH$_3$ | 8-CH$_3$ | (isopropoxymethyl-cyclopropyl) |

TABLE 23

[In the general formula (I),
Q = OH, R$_1$ = R$_2$ = R$_3$ = R$_4$ = R$_5$ = R$_6$ = H,
and n = 2.]

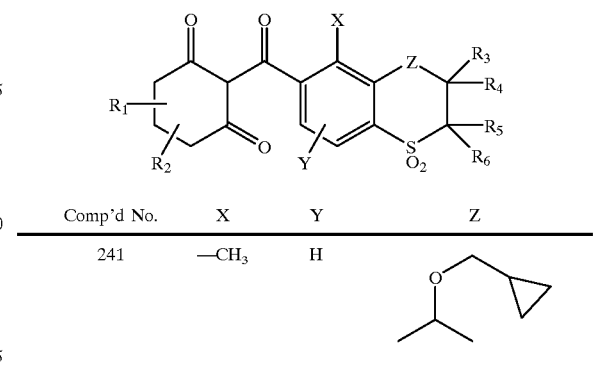

| Comp'd No. | X | Y | Z |
|---|---|---|---|
| 241 | —CH$_3$ | H | (isopropoxymethyl-oxirane) |

TABLE 23-continued

[In the general formula (I),
Q = OH, $R_1 = R_2 = R_3 = R_4 = R_5 = R_6$ = H,
and n = 2.]

| Comp'd No. | X | Y | Z |
|---|---|---|---|
| 242 | —Cl | 8-CH$_3$ | (isopropoxy-cyclopropylmethyl ether group) |
| 243 | —Cl | 8-CH$_3$ | (isopropoxy-isobutyl group) |
| 244 | —Cl | 8-CH$_3$ | (isopropoxy-neopentyl group) |
| 245 | —Cl | H | (isopropoxy-neopentyl group) |
| 246 | —Cl | 8-Cl | (isopropoxy-1,3-difluoroisopropyl group) |

The cyclohexanedione derivatives of the general formula (I) in which Q is other than -OH [general formula (I-Q)], provided by the present invention, are produced, e.g., by the following method.

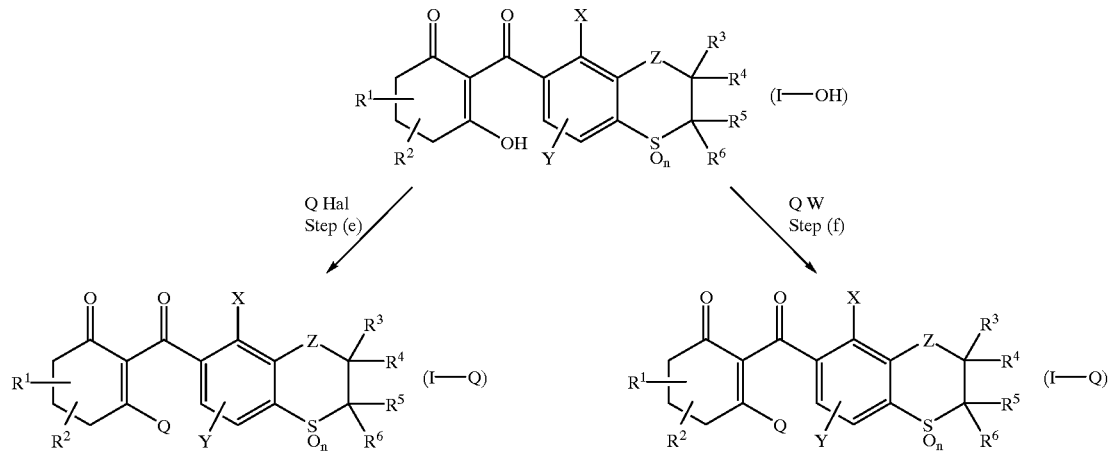

(Hal is halogen)

(W is halogen, hydroxyl group or hydrogen atom)

wherein X, Y, Z, $R^1$, $R^2$, $R^3$, $R^4$, $R^5$, $R^6$ and n are as defined above.

Compound of the general formula (I-OH) is reacted with a compound represented by QHal to give Compound of the general formula (I-Q).

A derivative of salt is obtained by a reaction with a base Q.

Each step will be explained below.

Step (e)

In step (e), Compound of the general formula (I-OH) is reacted with a compound represented by QHal to obtain Compound of the general formula (I-Q). In the step (e), preferably, the compound represented by QHal is used in an equimolar amount or more based on the amount of Compound of the general formula (I-OH), and the reaction is carried out in the presence of an organic base or an inorganic base. The above reaction is preferably carried out in a solvent inert to the reaction, such as dioxane, benzene, toluene, chloroform, methylene chloride, 1,2-dichloroethane or tetrahydrofuran. Further, the reaction may be carried out in a two-phase system such as water-benzene or water-chloroform. In the co-presence of an equimolar amount or more of a base such as sodium hydroxide, potassium hydroxide, sodium carbonate, potassium carbonate, triethylamine or pyridine, the reaction smoothly proceeds. The reaction temperature is preferably in the range of 0 to 60° C., particularly preferably in the range of from 0° C. to room temperature.

Step (f)

In step (f), Compound of the general formula (I-OH) is reacted with a compound represented by QW, to obtain Compound (I-Q). In the step (f), desirably, the compound represented by QX is used in an equimolar amount based on Compound of (I-OH). The above reaction is carried out desirably in a solvent such as dioxane, benzene, toluene, chloroform, methylene chloride, 1,2-dichloroethane or tetrahydrofuran. The reaction proceeds smoothly. The reaction temperature is preferably in the range of 0 to 60° C., particularly preferably in the range of from 0° C. to room temperature.

Table 24 shows preferred embodiments of the cyclohexanedione derivatives of the general formula (I-Q) obtained as described above.

TABLE 24

In the general formula (I),
$R_1 = R_2 = R_3 = R_4 = R_5 = R_6 = H$, and $n = 2$.

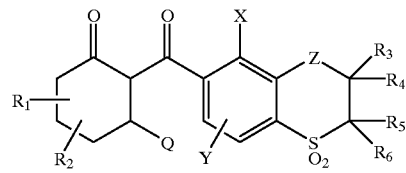

| Comp'd No. | X | Y | Z | Q |
|---|---|---|---|---|
| 250 | —Cl | 8-$CH_3$ | (isopropoxy group) | (acetyl group) |
| 251 | —Cl | 8-$CH_3$ | (isopropoxy group) | $Et_3NH^+$ |

In the column of Y in each of Tables 1 to 24, for example, 8-F means that a fluorine atom is substituted on the 8-position of thiochroman ring.

The herbicide of the present invention contains, as an essential component, an cyclohexanedione derivative of the general formula (I) provided by the present invention. The cyclohexanedione derivative of the present invention is mixed with a liquid carrier such as a solvent or a solid carrier such as a mineral fine powder, and the mixture can be prepared into the form of a wettable powder, an emulsifiable concentrate, a dust, granules, or the like. For imparting the preparation with emulsifiability, dispersibility and spreadability, a surfactant can be added.

When the herbicide of the present invention is used in the form of a wettable powder, generally, a composition is prepared by mixing 10 to 55% by weight of the cyclohexanedione derivative of the present invention, 40 to 88% by weight of a solid carrier and 2 to 5% by weight of a surfactant, and the composition can be used. Further, when it is used in the form of an emulsifiable concentrate, generally, it can be prepared by mixing 20 to 50% by weight of the cyclohexanedione derivative of the present invention, 35 to 75% by weight of a solvent and 5 to 15% by weight of a surfactant.

On the other hand, when the herbicide of the present invention is used in the form of a dust, generally, it can be prepared by mixing 1 to 15% by weight of the cyclohexanedione derivative of the present invention, 80 to 97% by weight of a solid carrier and 2 to 5% by weight of a surfactant. Further, when it is used in the form of granules, it can be prepared by mixing 1 to 15% by weight of the cyclohexanedione derivative of the present invention, 80 to 97% by weight of a solid carrier and 2 to 5% by weight of a surfactant. The above solid carrier can be selected from mineral fine powders, and the mineral fine powders include oxides such as diatomaceous earth and slaked lime, phosphates such as apatite, sulfates such as gypsum, and silicates such as talc, pyroferrite, clay, kaolin, bentonite, acid clay, white carbon, powdered quartz and powdered silica.

The solvent is selected from organic solvents. Specific examples of the solvent include aromatic hydrocarbons such as benzene, toluene and xylene, chlorinated hydrocarbons such as o-chlorotoluene, trichloroethane and trichloroethylene, alcohols such as cyclohexanol, amyl alcohol and ethylene glycol, ketones such as isophorone, cyclohexanone and cyclohexenyl-cyclohexanone, ethers such as butyl cellosolve, diethyl ether and methyl ethyl ether, esters such as isopropyl acetate, benzyl acetate and methyl phthalate, amides such as dimethylformamide, and mixtures of these.

Further, the surfactant can be selected from anionic, nonionic, cationic and amphoteric ones (amino acid and betaine).

The herbicide of the present invention may contain, as an active ingredient, other herbicidally active component in combination with the cyclohexanedione derivative of the general formula (I) as required. The "other" herbicidally active component includes known herbicides such as phenoxy-, diphenyl ether-, triazine-, urea-, carbamate-, thiocarbamate-, acid anilide-, pyrazole-, phosphoric acid-, sulfonylurea- and oxadiazone-based herbicides, and it can be properly selected from these herbicides as required.

Further, the herbicide of the present invention may be used as a mixture with any one of insecticides, bactericides, plant growth regulators and fertilizers.

The herbicide of the present invention can be used as a herbicide for upland soil by any method of pre-emergence treatment, treatment by mixing it with soil, and post-emergence treatment. The cropland weeds to which the compound of the present invention is applied include broad-leaved weeds such as solanaceous weeds typified by black nightshade (*Solanum nigrum*) and Jimsonweed (*Datura stramonium*); malvaceous weeds typified by velvetleaf (*Abutilon theophrasti*) and pricky sida (*Sida spinosa*); convolvulaceous weeds typified by morning-glories (Impmoea spps.) such as tall morning-glory (*Ipomoea purpurea*) and hedge bindweeds (Calystegia spps.); amaranthaceous weeds typified by livid amaranth (*Amaranthus lividus*); composite weeds typified by cocklebur (*Xanthium strumarium*), common ragweed (*Ambrosia artemisiaefolia*), sunflower (*Helianthus annus*), hairy galinsoga (*Galinsoga ciliata*), Canada thistle (*Cirsium arvense*), groundsel (*Senecio vulgaris*) and annual fleabane (*Erigeron annus*); brassicaceous weeds typified by yellow cress (*Rorippa indica*), wild mustard (*Sinapis arvensis*) and shepherdspurse (*Capsella bursa-pastris*); polygonaceous weeds typified by wild buckwheat (*Polygonum convolvulus*) and wild buckwheat (*Polygonum convolvulus*); portulacaceous weeds typified by common purslane (*Portulaca oleracea*); chenopodiaceous weeds typified by common lambsquaters (*Chenopodium album*), fig-leaved goosefoot (*Chenopodium ficifolium*) and kochia (*Kochia scoparia*); caryophyllaceous weeds typified by common chickweed (*Stellaria media*); scrophularaceous weeds typified by persian speedwell (*Veronica persica*); commelinaceous weeds typified by Asiatic dayfower (*Commelina communis*); labiatae weeds typified by henbit (*Laminum amplexicaule*) and purple deadnettle (*Lamium purpureum*); euphorbiaceous weeds typified by milk purslane (*Euphorbia supina*) and spotted spurge (*Euphorbia maculata*); rubiaceous weeds typified by bedstraw (*Galium spurium*), cleavers (*Galium aparine*) and madder (*Rubia akane*); violaceous weeds typified by violet (*Viola arvensis*); and leguminous weeds typified by hemp sesbania (*Sesbania exaltata*) and sicklepod (*Cassia obtusifolia*); graminaceous weeds typified by sorghum (*Sorghum bicolor*), fall panicum (*Panicum dichotomiflorum*), Johnsongrass (*Sorghum halepense*), barnyardgrass (*Ehinocholoa crus-galli*), henry crabgrass (*Digitaria adscendens*), wildoat (*Avena fatua*), goosegrass (*Eleusine indica*), green foxtail (*Setaria viidis*) and water foxtail (*Alopecurus aequalis*); and cyperaceous weeds typified by purple nutsedge (*Cyperus rotundus, Cyperus esculentus*).

Further, the herbicide of the present invention can be also used for any one of pre-emergence treatment and post-emergence treatment under submergence as a herbicide for paddy land. Examples of paddy weeds include alismataceous weeds typified by oriental waterplantain (*Alisma canaliculatum*), arrowhead (*Sagittaria trifolia*) and Sagittaria pygmaea, cyperaceous weeds typified by umbrella plant (*Cyperus difformis*), *Cyperus serotinus*, bulrush (*Scirpus juncoides*) and water chestnut (*Eleochadaris kuroguwai*); scrothulariaceous weeds typified by common falsepimpernel (*Lindernia pyxidaria*); potenderiaceous weeds typified by monochoria (*Monochoria Vaginalis*); potamogetonaceous weeds typified by largeleaf pondweed (*Potamogeton distinctus*); lythraceous weeds typified by toothcup (*Rotala indica*); and graminaceous weeds typified by barnyardgrass (*Echinochloa crus-galli*).

The present invention will be explained more in detail with reference to Preparation Examples and Herbicide Examples hereinafter, while the present invention shall not be limited by these Examples.

PREPARATION EXAMPLE 1

5-Chloro-8-fluoro-6-(1',3'-dioxocyclohexan-2-yl-carbonyl)-4-methoxyiminothiochroman-1,1-dioxide (Compound No. 1)

1-1) Synthesis of 5-chloro-8-fluoro-6-carboxyl-4-methoxyiminothiochroman-1,1-dioxide 5-Chloro-8-fluoro-6-carboxyl-4-methoxyiminothiochroman-1,1-dioxide was synthesized according to the method described in WO96/30368.

$^1$H-NMR (CDCl$_3$): δ 3.35–3.45 (m,2H), 3.63–3.69 (m,2H), 4.08 (s,3H), 7.69 (d,1H)

1-2) Synthesis of 5-chloro-8-fluoro-6-(3'-oxocyclohexenyl)oxycarbonyl-4-methoxyiminothiochroman-1,1-dioxide 0.50 Gram (1.6 mmol) of 5-chloro-8-fluoro-6-carboxyl-4-methoxyiminothiochroman-1,1-dioxide was dissolved in 3 ml of dichloroethane, 0.34 ml (3.0 eq., 4.7 mmol) of thionyl chloride was added, and the mixture was refluxed under heat for 3 hours. Then, the solvent was distilled off, to give an acid chloride. Then, a solution of the obtained acid chloride in tetrahydrofuran was added to a solution of 0.18 g (1.0 eq., 1.6 mmol) of 1,3-cyclohexanedione in tetrahydrofuran, and further, 0.2 ml (1.0 eq., 1.6 mmol) of triethylamine was dropwise added. The mixture was stirred at room temperature for 2 hours, and the solvent was distilled off. The resultant residue was dissolved in ethyl acetate and consecutively washed with a 0.2 N hydrochloric acid aqueous solution, with a saturated sodium hydrogencarbonate aqueous solution and with a saturated sodium chloride aqueous solution. Then, the washed product was dried over anhydrous sodium sulfate, and the solvent was distilled off. The residue was subjected to column chromatography (ethyl acetate:n-hexane=1:1) to give 0.21 g (yield 58%) of 5-chloro-8-fluoro-6-(3'-oxocyclohexenyl)oxycarbonyl-4-methoxyiminothiochroman-1,1-dioxide.

$^1$H-NMR (CDCl$_3$): δ 2.0–2.7 (m,6H), 3.4–3.5 (m,4H), 4.11 (s,3H), 6.06 (bs,1H), 7.54 (d,1H)

1-3) Synthesis of 5-chloro-8-fluoro-6-(1',3'-dioxocyclohexan-2-yl-carbonyl)-4-methoxyiminothiochroman-1,1-dioxide 0.22 Gram (0.53 mmol) of 5-chloro-8-fluoro-6-(3'-oxocyclohexenyl)oxycarbonyl-4-methoxyiminothiochroman-1,1-dioxide was dissolved in 4 ml of acetonitrile, 0.1 ml (1.0 eq., 0.53 mmol) of triethylamine and 3 drops of acetonecyanhydrin were added, and the mixture was stirred at room temperature for 1 day. After the completion of the reaction, the reaction mixture was extracted with a saturated sodium hydrogencarbonate aqueous solution, and an aqueous layer was washed with methylene chloride. The aqueous layer was neutralized with 2% hydrochloric acid and extracted with ethyl acetate. An organic layer was washed with a saturated sodium chloride aqueous solution and dried over anhydrous sodium sulfate, and the solvent was distilled off to give 0.22 g (yield 100%) of 5-chloro-8-fluoro-6-(1',3'-dioxocyclohexan-2-yl-carbonyl)-4-methoxyimino-thiochroman-1,1-dioxide.

$^1$H-NMR (CDCl$_3$): δ 2.0–2.8 (m,7H), 3.3–3.4 (m,2H), 3.6–3.7 (m,2H), 4.05 (s,3H), 7.32 (d,1H)

IR (KBr): 2950, 1710, 1680, 1250, 1150cm$^{-1}$

PREPARATION EXAMPLE 2

5-Chloro-8-fluoro-6-(1',3'-dioxocyclohexan-2-yl-carbonyl)-4-(2'-fluoroethoxy)thiochroman-1,1-dioxide (Compound No. 2)

2-1) Synthesis of 5-chloro-8-fluoro-6-carboxyl-4-(2'-fluoroethoxy)thiochroman-1,1-dioxide 5-Chloro-8-fluoro-6-carboxyl-4-(2'-fluoroethoxy)thiochroman-1,1-dioxide was synthesized according to the method described in WO96/31507.

$^1$H-NMR (acetone-d$_6$): δ 2.3–3.2 (m,2H), 3.3–4.5 (m,5H), 4.88 (t,1H), 5.07 (m,1H), 7.79 (d,1H)

m.p. 163–165° C.

2-2) Synthesis of 5-chloro-8-fluoro-6-(3'-oxocyclohexenyl)oxycarbonyl-4-(2'-fluoroethoxy)-thiochroman-1,1-dioxide 0.47 Gram (1.4 mmol) of 5-chloro-8-fluoro-6-carbonyl-4-(2'-fluoroethoxy)thiochroman-1,1-dioxide was dissolved in 3 ml of dichloroethane, 0.20 ml (2.0 eq., 2.8 mmol) of thionyl chloride was added, and the mixture was stirred at 40–50° C. for 3 hours. Then, the solvent was distilled off to give an acid chloride. Then, a solution of the obtained acid chloride in tetrahydrofuran was added to a solution of 0.17 g (1.0 eq., 1.4 mmol) of 1,3-cyclohexanedione in tetrahydrofuran, and further, 0.2 ml (1.0 eq., 1.6 mmol) of triethylamine was dropwise added. The mixture was stirred at room temperature for 2 hours, and the solvent was distilled off. The resultant residue was dissolved in ethyl acetate and consecutively washed with a 0.2 N hydrochloric acid aqueous solution, with a saturated sodium hydrogencarbonate aqueous solution and with a saturated sodium chloride aqueous solution. Then, the washed product was dried over anhydrous sodium sulfate, and the solvent was distilled off. Thereafter, the residue was subjected to column chromatography (ethyl acetate:n-hexane=1:1) to give 0.50 g (yield 81%) of 5-chloro-8-fluoro-6-(3'-oxocyclohexenyl)oxycarbonyl-4-(2'-fluoroethoxy)thiochroman-1,1-dioxide.

$^1$H-NMR (CDCl$_3$): δ 2.0–2.8 (m,8H), 3.0–4.3 (m,4H), 4.85 (t,1H), 4.96 (bs,1H), 6.06 (bs,1H), 7.54 (d,1H)

2-3) Synthesis of 5-chloro-8-fluoro-6-(1',3'-dioxocyclohexan-2-yl-carbonyl)-4-(2'-fluoroethoxy)-1,1-dioxide 0.50 Gram (1.1 mmol) of 5-chloro-8-fluoro-6-(3'-oxocyclohexenyl)oxycarbonyl-4-(2'-fluoroethoxy)-thiochroman-1,1-dioxide was dissolved in 3 ml of acetonitrile, 0.15 ml (1.0 eq., 1.1 mmol) of triethylamine and 3 drops of acetonecyanhydrin were added, and the mixture was stirred at room temperature for 1 day. After the completion of the reaction, the reaction mixture was extracted with a saturated sodium hydrogencarbonate aqueous solution, and an aqueous layer was washed with methylene chloride. The aqueous layer was neutralized with 2% hydrochloric acid and extracted with ethyl acetate. An organic layer was washed with a saturated sodium chloride aqueous solution and dried over anhydrous sodium sulfate, and the solvent was distilled off to give 0.50 g (yield 100%) of 5-chloro-8-fluoro-6-(1',3'-dioxocyclohexan-2-yl-carbonyl)-4-(2'-fluoroethoxy) thiochroman-1,1-dioxide.

$^1$H-NMR (CDCl$_3$): δ 1.8–3.4 (m,8H), 3.6–4.4 (m,5H), 4.85 (t,1H), 4.98 (bs,1H), 7.36 (d,1H)

IR (KBr): 2975, 1690, 1320, 1170cm$^{-1}$

PREPARATION EXAMPLE 3

5-Chloro-8-methyl-6-(1',3'-dioxocyclohexan-2-yl-carbonyl)-4-methoxythiochroman-1,1-dioxide (Compound No. 3)

3-1) Synthesis of 5-chloro-8-methyl-6-carboxyl-4-methoxythiochroman-1,1-dioxide

5-Chloro-8-methyl-6-carboxyl-4-methoxythiochroman-1,1-dioxide was synthesized according to the method described in WO93/18031.

$^1$H-NMR (acetone-d$_6$): δ 2.4–4.0 (m,4H), 2.73 (s,3H), 3.52 (s,3H), 4.85 (t,1H), 7.72 (d,1H)

3-2) Synthesis of 5-chloro-8-methyl-6-(3'-oxocyclohexenyl)oxycarbonyl-4-methoxythiochroman-1,1-dioxide 0.84 Gram (2.8 mmol) of 5-chloro-8-methyl-6-carboxyl-4-methoxythiochroman-1,1-dioxide was dissolved in 6.7 ml of t-amyl alcohol, 0.34 g (1.1 eq., 3.0 mmol) of 1,3-cyclohexanedione and 0.63 g (1.1. eq., 3.0 mmol) of N,N-dicyclohexylcarbodiimide were added, and the mixture was stirred at room temperature for 3 hours. Then, the solvent was distilled off, ethyl acetate and water were added, and an insoluble substance was removed by filtration. Then, an organic layer was washed with a saturated sodium hydrogencarbonate aqueous solution and with a saturated sodium chloride aqueous solution. Then, the washed product was dried over anhydrous sodium sulfate, and the solvent was distilled off. The residue was subjected to column chromatography (ethyl acetate:n-hexane=1:1) to give 0.40 g (yield 36%) of 5-chloro-8-methyl-6-(3'-oxocyclohexenyl) oxycarbonyl-4-methoxythiochroman-1,1-dioxide.

$^1$H-NMR (CDCl$_3$): δ 2.0–2.8 (m,9H), 2.78 (s,3H), 3.0–3.4 (m,1H), 3.49 (s,3H), 3.6–4.2 (m,1H), 4.81 (t,1H), 6.07 (bs,1H), 7.69 (s,1H)

3-3) Synthesis of 5-chloro-8-methyl-6-(1',3'-dioxocyclohexan-2-yl-carbonyl)-4-methoxythiochroman-1,1-dioxide 0.40 Gram (1.0 mmol) of 5-chloro-8-methyl-6-(3'-oxocyclohexenyl)oxycarbonyl-4-methoxythiochroman-1,1-dioxide was dissolved in 2.4 ml of acetonitrile, 0.14 ml (1.0 eq., 1.0 mmol) of triethylamine and 3 drops of acetonecyanhydrin were added, and the mixture was stirred at room temperature for 8 hours. After the completion of the reaction, the reaction mixture was extracted with a sodium carbonate aqueous solution, and an aqueous layer was washed with ethyl acetate. The aqueous layer was adjusted to a pH of 1 with 5% hydrochloric acid and then extracted with ethyl acetate. An organic layer was washed with a saturated sodium chloride aqueous solution and dried over anhydrous sodium sulfate, and the solvent was distilled off to give 0.26 g (yield 65%) of 5-chloro-8-methyl-6-(1',3'-dioxocyclohexan-2-yl-carbonyl)-4-methoxythiochroman-1,1-dioxide.

$^1$H-NMR (CDCl$_3$): δ 2.0–2.8 (m,9H), 2.80 (s,3H), 3.0–3.4 (m,1H), 3.46 (s,3H), 3.6–4.1 (m,1H), 4.72 (t,1H), 7.06 (s,1H)

IR (KBr): 2950, 1690, 1300, 1145cm$^{-1}$

PREPARATION EXAMPLE 4

5-Trifluoromethyl-3,3,8-trimethyl-6-(1',3'-dioxocyclohexan-2-yl-carbonyl)-thiochroman-4-one-1,1,-dioxide (Compound No. 4)

4-1) Synthesis of 5-trifluoromethyl-3,3,8-trimethyl-6-carboxyl-thiochroman-4-one-1,1-dioxide 5-Trifluoromethyl-3,3,8-trimethyl-6-carboxyl-thiochroman-4-one-1,1-dioxide was synthesized according to the method of synthesizing 3,3,5,8-tetramethyl-6-carboxyl-thiochroman-4-one-1,1-dioxide described in WO96/25413.

$^1$H-NMR (CDCl$_3$): δ 1.51 (s,6H), 2.82 (s,2H), 3.61 (s,2H), 7.75 (s,1H)

4-2) Synthesis of 5-trifluoromethyl-3,3,8-trimethyl-6-(3'-oxocyclohexenyl)oxycarbonylthiochroman-4-one-1,1-dioxide 0.40 Gram (1.1 mmol) of 5-trifluoromethyl-3,3,8-trimethyl-6-carboxyl-thiochroman-4-one-1,1-dioxide was dissolved in 3 ml of dichloroethane, 0.28 g (2.0 eq., 2.4 mmol) of thionyl chloride was added, and the mixture was refluxed under heat for 1.5 hours. Then, the solvent was distilled off to give an acid chloride. Then, a solution of the obtained acid chloride in tetrahydrofuran was added to a solution of 0.14 g (1.1 eq., 1.3 mmol) of 1,3-cyclohexanedione in tetrahydrofuran, and further, 0.13 g (1.1 eq., 1.3 mmol) of triethylamine was dropwise added. The mixture was stirred at room temperature for 2 hours, and then the solvent was distilled off. The resultant residue was dissolved in ethyl acetate and washed with a 0.2 N hydrochloric acid aqueous solution, with a saturated sodium hydrogencarbonate aqueous solution and with a saturated sodium chloride aqueous solution. Then, the washed product was dried over anhydrous sodium sulfate, and the solvent was distilled off to give 0.29 g (yield 58%) of 5-trifluoromethyl-3,3,8-trimethyl-6-(3'-oxocyclohexenyl) oxycarbonylthiocchroman-4-one-1,1-dioxide.

$^1$H-NMR (CDCl$_3$): δ 1.52 (s,6H), 2.0–2.8 (m,6H), 2.85 (s,3H), 3.61 (s,2H), 6.09 (bs,1H), 7.73 (s,1H)

4-3) Synthesis of 5-trifluoromethyl-3,3,8-trimethyl-6-(1',3'-dioxocyclohexan-2-yl-carbonyl)thiochroman-4-one-1,1-dioxide 0.29 Gram (0.65 mmol) of 5-trifluoromethyl-3,3,8-trimethyl-6-(3'-oxocyclohexenyl) oxycarbonylthiocchroman-4-one-1,1-dioxide was dissolved in 1.5 ml of acetonitrile, 0.07 g (1.1 eq., 0.69 mmol) of triethylamine and 3 drops of acetonecyanhydrin were added, and the mixture was stirred at room temperature for 1 day. After the completion of the reaction, the reaction mixture was extracted with a saturated sodium hydrogencarbonate aqueous solution, and an aqueous layer was washed with methylene chloride. The aqueous layer was neutralized with 2% hydrochloric acid and extracted with ethyl acetate. An organic layer was washed with a saturated sodium chloride aqueous solution and then dried over anhydrous sodium sulfate, and the solvent was distilled off to give 0.15 g (yield 30%) of 5-trifluoromethyl-3,3,8-trimethyl-6-(1',3'-dioxocyclohexan-2-yl-carbonyl) thiochroman-4-one-1,1-dioxide.

$^1$H-NMR (CDCl$_3$): δ 1.51 (s,6H), 2.0–2.8 (m,7H), 2.82 (s,3H), 2.70 (s,3H), 3.58 (s,2H), 7.16 (s,1H)

IR (KBr): 3000, 1730, 1690, 1300, 1195, 1150 cm$^{-1}$

PREPARATION EXAMPLE 5

3,3,5,8-Tetramethyl-6-(1',3'-dioxocyclohexan-2-yl-carbonyl)-thiochroman-4-one-1,1-dioxide (Compound No. 5)

5-1) Synthesis of 3,3,5,8-tetramethyl-6-carboxyl-thiochroman-4-one-1,1-dioxide 3,3,5,8-Tetramethyl-6-carboxyl-thiochroman-4-one-1,1-dioxide was synthesized according to the method described in WO96/25413.

$^1$H-NMR (CDCl$_3$): δ 1.47 (s,6H), 2.58 (s,3H), 2.76 (s,3H), 3.53 (s,2H), 7.93 (s,1H)

5-2) Synthesis of 3,3,5,8-tetramethyl-6-(3'-oxocyclohexenyl)oxycarbonylthiochroman-4-one-1,1-dioxide 0.70 Gram (2.4 mmol) of 3,3,5,8-tetramethyl-6-carboxyl-thiochroman-4-one-1,1-dioxide was dissolved in 4 ml of dichloroethane, 0.56 g (2.0 eq., 4.7 mmol) of thionyl chloride was added, and the mixture was stirred at 55° C. for 1.5 hours. Then, the solvent was distilled off to give an acid chloride. Then, a solution of the obtained acid chloride in tetrahydrofuran was added to a solution of 0.29 g (2.6 mmol) of 1,3-cyclohexanedione in tetrahydrofuran, and further, 0.27 g (1.1 eq., 2.7 mmol) of triethylamine was dropwise added. The mixture was stirred at room temperature for 2 hours, and then the solvent was distilled off. The resultant residue was dissolved in ethyl acetate and consecutively washed with a 0.2 N hydrochloric acid aqueous solution, with a saturated sodium hydrogencarbonate aqueous solution and with a saturated sodium chloride aqueous solution. Then, the washed product was dried over anhydrous sodium sulfate, and the solvent was distilled off to give 0.67 g (yield 68%) of 3,3,5,8-tetramethyl-6-(3'-oxocyclohexenyl) oxycarbonylthiochroman-4-one-1,1-dioxide.

$^1$H-NMR (CDCl$_3$): δ 1.46 (s,6H), 2.0–2.8 (m,6H), 2.54 (s,3H), 2.76 (s,3H), 3.52 (s,2H), 6.04 (bs,1H), 7.85 (s,1H)

5-3) Synthesis of 3,3,5,8-tetramethyl-6-(1',3'-dioxocyclohexan-2-yl-carbonyl)-thiochroman-4-one-1,1-dioxide 0.63 Gram (1.6 mmol) of 3,3,5,8-tetramethyl-6-(3'-oxocyclohexenyl)oxycarbonylthiochroman-4-one-1,1-dioxide was dissolved in 3 ml of acetonitrile, 0.17 g (1.1 eq., 1.7 mmol) of triethylamine and 3 drops of acetonecyanhydrin were added, and the mixture was stirred at room temperature for 1 day. After the completion of the reaction, the reaction mixture was extracted with a saturated sodium hydrogencarbonate aqueous solution, and an aqueous layer was washed with methylene chloride. The washed aqueous layer was neutralized with 2% hydrochloric acid, and extracted with ethyl acetate. An organic layer was washed with a saturated sodium chloride aqueous solution and dried over anhydrous sodium sulfate, and the solvent was distilled off to give 0.51 g (yield 81%) of 3,3,5,8-tetramethyl-6-(1',3'-dioxocyclohexan-2-yl-carbonyl)-thiochroman-4-one-1,1-dioxide.

$^1$H-NMR (CDCl$_3$): δ 1.45 (s,6H), 2.0–3.0 (m,7H), 2.05 (s,3H), 2.70 (s,3H), 3.51 (s,2H), 7.07 (s,1H)

IR (KBr): 2975, 1700, 1680, 1260, 1195, 1125cm$^{-1}$

Table 25 shows structures and NMR spectra of starting materials used in the above Preparation Examples 1 to 5, and Tables 37 and 49 show structures and physical property data of compounds obtained therein.

PREPARATION EXAMPLES 6–55

Compounds shown in Tables 38 to 48 were obtained from compounds shown in Table 26 to 36 as starting materials in the same manner as in Preparation Example 5. Tables 50 to 60 show physical property data of the obtained compounds.

PREPARATION EXAMPLE 56

Synthesis of 5-chloro-8-methyl-6-(1-acetoxy-3-oxocyclohexen-2-yl)-4-(2-porpoxy)thiochroman-1,1-dioxide 0.5 Gram of 5-chloro-8-methyl-6(1,3-dioxocyclohexan-2-ylcarbonyl)-4-(2-propoxy)thiochroman-1,1-dioxide (Compound No. 15 in Table 38) was dissolved in 5 ml of 1,2-dichloroethane, and 0.10 g of triethylamine was added. To the resultant solution was added 0.13 g of acetyl chloride, and the mixture was stirred at room temperature for 8 hours. The reaction mixture was diluted with ethyl acetate, washed with a 5% hydrochloric acid aqueous solution twice, washed with a saturated sodium bicarbonate solution twice, washed with a saturated sodium chloride aqueous solution and dried over anhydrous sodium sulfate. A drying agent was filtered off, and the remainder was concentrated. Then, the resultant oil was purified by column chromatography to give 0.30 g of Compound No. 250 shown in Table 38 (yield 54%). Table 60 shows the physical property date of the obtained compound.

PREPARATION EXAMPLE 57

Synthesis of 5-chloro-8-methyl-6-(3-oxocyclohexen-2-yl)-4-(2-propoxy)thiochroman-1,1-dioxide 0.5 Gram of 5-chloro-8-methyl-6(1,3-dioxocyclohexan-2-yl)-4-(2-propoxy)thiochroman-1,1-dioxide (Compound No. 15 in Table 38) prepared in Preparation Example 6 was dissolved in 5 ml of 1,2-dichloroethane, and 0.12 g of triethylamine was added. The mixture was stirred at room temperature for 1 hour. A formed crystal was recovered by filtration to give, as an end product, 0.3 g of Compound No. 251 shown in Table 48 (yield 65%). Table 60 shows the physical property date of the obtained compound.

TABLE 25

| Prep. Ex. No. | Starting material Comp'd of the formula (II) | NMR (ppm internal standard: TMS) |
|---|---|---|
| 1 | (structure) | 3.35–3.45(2H, m) 3.63–3.69(2H, m) 4.08(3H, s) 7.69(1H, d) CDCl$_3$ |
| 2 | (structure) | 2.3–3.2(2H, m) 3.3–4.5(5H, m) 4.88(1H, t) 5.07(1H, m) 7.79(1H, d) deuteroacetone |
| 3 | (structure) | 2.4–4.0(4H, m) 2.73(3H, s) 3.52(3H, s) 4.85(1H, t) 7.72(1H, s) deuteroacetone |
| 4 | (structure) | 1.51(6H, s) 2.82(3H, s) 3.61(2H, s) 7.75(1H, s) CDCl$_3$ |
| 5 | (structure) | 1.47(6H, s) 2.58(3H, s) 2.76(3H, s) 3.53(2H, s) 7.93(1H, s) CDCl$_3$ |

TABLE 26

| Prep. Ex. No. | Starting material Comp'd of the formula (II) | NMR (ppm internal standard: TMS) |
|---|---|---|
| 6 | (structure) | 1.27(6H, d) 2.4–2.8(2H, m) 2.78(3H, s) 3.1–3.4(1H, m) 3.7–4.2(2H, m) 5.15(1H, m) 6.2–6.7(1H, broad) 7.76(1H, s) CDCl$_3$ |

TABLE 26-continued

| Prep. Ex. No. | Starting material Comp'd of the formula (II) | NMR (ppm internal standard: TMS) |
|---|---|---|
| 7 | (structure) | 2.3–2.8(2H, m), 2.62(3H, s), 2.78(3H, s), 3.1–3.5(2H, m), 3.5–4.3(5H, m), 5.9–6.4(1H, broad), 7.81(1H, s), CDCl$_3$ |
| 8 | (structure) | 2.5–4.3(6H, m), 2.73(3H, s), 4.60(2H, dt), 5.06(1H, m), 7.74(1H, s), deuteroacetone |
| 9 | (structure) | 2.5–2.8(2H, m), 2.79(3H, s), 3.1–3.5(1H, m), 3.5–3.8(2H, m), 3.8–4.2(3H, m), 5.00(1H, m), 6.4–7.1(1H, broad), 7.80(1H, s), CDCl$_3$ |
| 10 | (structure) | 2.3–3.9(4H, m), 3.54(3H, s), 4.86(1H, m), 7.96(2H, ABq), CDCl$_3$ |

TABLE 27

| Prep. Ex. No. | Starting material Comp'd of the formula (II) | NMR (ppm internal standard: TMS) |
|---|---|---|
| 11 | (structure) | 1.26(3H, t), 2.4–4.3(6H, m), 2.78(3H, s), 4.93(1H, s), 7.3–7.8(1H, broad), 7.70(1H, s), CDCl$_3$ |
| 12 | (structure) | 3.1–3.6(4H, m), 3.89(3H, s), 7.78(2H, ABq), deuteroacetone |

TABLE 27-continued

| Prep. Ex. No. | Starting material Comp'd of the formula (II) | NMR (ppm internal standard: TMS) |
|---|---|---|
| 13 | (structure) | 1.50(6H, s), 2.68(3H, s), 3.49(2H, s), 7.90(1H, d), 8.22(1H, d), CDCl$_3$ |
| 14 | (structure) | 0.93(3H, t), 1.4–1.8(2H, m), 2.3–4.0(6H, m), 2.73(3H, s), 4.96(1H, m), 7.71(1H, s), deuteroacetone |

TABLE 28

| Prep. Ex. No. | Starting material Comp'd of the formula (II) | NMR (ppm internal standard: TMS) |
|---|---|---|
| 15 | (structure) | 1.31(3H, d), 2.43–2.90(2H, m), 2.57(3H, s), 2.77(3H, s), 3.10–3.40(1H, m), 3.70–4.30(2H, m), 4.77–4.97(1H, m), 5.10–5.45(2H, m), 5.66–6.15(1H, m), 7.78(1H, s), CDCl$_3$ |
| 16 | (structure) | 0.48–1.80(5H, m), 2.20–2.70(1H, m), 2.51(3H, s), 2.70(3H, s), 2.90–4.40(4H, m), 4.60–4.80(1H, m), 4.90–6.20(3H, m), 7.72(1H, s), CDCl$_3$ |
| 17 | (structure) | 1.67(3H, s), 2.20–2.90(1H, m), 2.49(3H, s), 2.67(3H, s), 3.00–3.36(1H, m), 3.37–4.02(4H, m), 4.52–4.72(1H, m), 4.82(1H, s), 4.90(1H, s), 7.66(1H, s), CDCl$_3$ |

TABLE 28-continued

| Prep. Ex. No. | Starting material Comp'd of the formula (II) | NMR (ppm internal standard: TMS) |
|---|---|---|
| 18 | [structure: 5,8-dimethyl-4-(2-chloroallyloxy)-thiochroman-6-carboxylic acid 1,1-dioxide] | 2.60–2.74(1H, m) 2.61(3H, s) 2.77(3H, s) 3.10–3.40(1H, m) 3.70–4.15(2H, m) 4.19(2H, s) 4.70–4.90(1H, m) 5.40(1H, s) 5.50(1H, s) 7.80(1H, s) CDCl$_3$ |
| 19 | [structure: 5,8-dimethyl-4-(propargyloxy)-thiochroman-6-carboxylic acid 1,1-dioxide] | 2.57(1H, t) 2.41–3.10(1H, m) 2.65(3H, s) 2.77(3H, s) 3.18–3.35(1H, m) 3.70–4.18(2H, m) 4.33(2H, d) 4.91–5.11(1H, m) 7.81(1H, s) CDCl$_3$ |

TABLE 29

| Prep. Ex. No. | Starting material Comp'd of the formula (II) | NMR (ppm internal standard: TMS) |
|---|---|---|
| 20 | [structure: 5,8-dimethyl-4-(1-methyl-2-propynyloxy)-thiochroman-6-carboxylic acid 1,1-dioxide] 7:3 diastereomer mixture | 1.49(3H, d) 2.30–2.95(2H, m) 2.55(1H, d) 2.59(0.9H, s) 2.68(2.1H, s) 2.76(3H, s) 3.05–3.40(1H, m) 3.55–4.55(2H, m) 4.80–4.95(0.3H, m) 5.15–5.25(0.7H, m) 7.78(1H, s) CDCl$_3$ |
| 21 | [structure: 5,8-dimethyl-4-(2-butynyloxy)-thiochroman-6-carboxylic acid 1,1-dioxide] | 1.87(3H, t) 2.25–3.48(2H, m) 2.60(3H, s) 2.70(3H, s) 3.60–4.20(2H, m) 4.38(2H, d) 4.96–5.16(1H, m) 7.69(1H, s) deuteroacetone |
| 22 | [structure: 5,8-dimethyl-4-(3-butynyloxy)-thiochroman-6-carboxylic acid 1,1-dioxide] | 1.90–3.10(4H, m) 2.59(3H, s) 2.71(3H, s) 3.17–3.32(1H, m) 3.67–4.23(4H, m) 4.77–4.97(1H, m) 7.70(1H, s) deuteroacetone |
| 23 | [structure: 5,8-dimethyl-4-(2-methoxyethoxy)-thiochroman-6-carboxylic acid 1,1-dioxide] | 2.03–4.14(4H, m) 2.61(3H, s) 2.76(3H, s) 3.38(3H, s) 3.43–3.78(4H, m) 4.61–4.81(1H, m) 7.76(1H, s) deuteroacetone |

TABLE 29-continued

| Prep. Ex. No. | Starting material Comp'd of the formula (II) | NMR (ppm internal standard: TMS) |
|---|---|---|
| 24 | 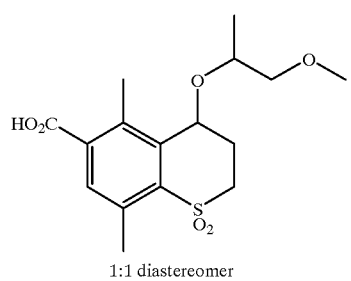<br>1:1 diastereomer mixture | 1.18(1.5H, d) 1.25(1.5H, d) 2.35–2.90(2H, m) 2.61(1.5H, s) 2.65(1.5H, s) 2.71(3H, s) 2.95–3.70(3H, m) 3.32(1.5H, s) 3.33(1.5H, s) 3.80–4.20(2H, m) 5.00–5.12(0.5H, m) 5.15–5.26(0.5H, m) 7.68(1H, s) deuteroacetone |

TABLE 30

| Prep. Ex. No. | Starting material Comp'd of the formula (II) | NMR (ppm internal standard: TMS) |
|---|---|---|
| 25 | 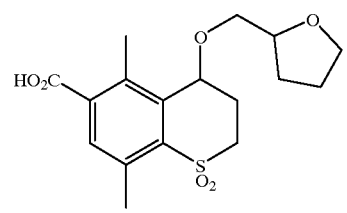 | 1.50–2.20(4H, m) 2.25–2.95(2H, m) 2.59(3H, s) 2.74(3H, s) 3.10–3.35(1H, m) 3.40–4.20(6H, m) 4.60–4.88(1H, m) 7.73(1H, s) $CDCl_3$ |
| 26 | 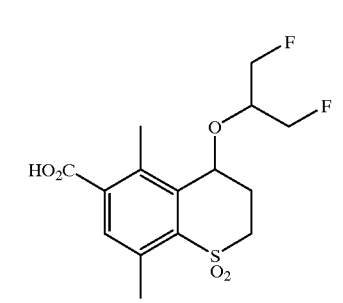 | 2.5–2.9(2H, m) 2.65(3H, s) 2.78(3H, s) 3.1–3.4(1H, m) 3.8–4.5(4H, m) 4.7–4.9(2H, m) 5.0–5.2(1H, m) 7.81(1H, s) $CDCl_3$ |
| 27 | 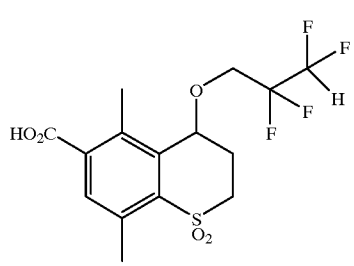 | 2.58(3H, s) 2.78(3H, S) 2.5–2.9(2H, m) 3.1–3.4(1H, m) 3.6–4.2(3H, m) 4.75–4.98(1H, m) 5.88(1H, tt) 7.85(1H, s) $CDCl_3$ |
| 28 | 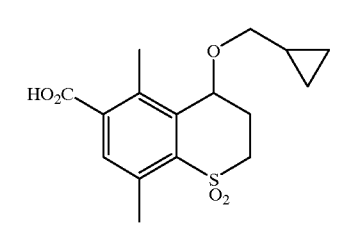 | 0.15–0.35(2H, m) 0.45–0.70(2H, m) 0.85–1.25(1H, m) 2.30–2.80(2H, m) 2.60(3H, s) 2.76(3H, s) 3.10–3.55(3H, m) 3.70–3.95(1H, m) 4.58–4.78(1H, m) 7.78(1H, s) $CDCl_3$ |

TABLE 30-continued

| Prep. Ex. No. | Starting material Comp'd of the formula (II) | NMR (ppm internal standard: TMS) |
|---|---|---|
| 29 | [structure: 5-methyl-4-(but-3-en-2-yloxy)-thiochroman-6-carboxylic acid S,S-dioxide; 1:1 diastereomer mixture] | 1.30(1.5H, d) 1.73(1.5H, d)<br>2.63(1.5H, s) 2.65(1.5H, s)<br>2.77–3.00(1H, m) 3.10–3.30(1H, m)<br>3.63–4.32(3H, m) 4.74–4.82(0.5H, m)<br>4.86–4.96(0.5H, m) 5.10–5.36(2H, m)<br>5.60–6.05(1H, m) 7.85(1H, d)<br>8.08(1H, d)<br>$CDCl_3$ |

TABLE 31

| Prep. Ex. No. | Starting material Comp'd of the formula (II) | NMR (ppm internal standard: TMS) |
|---|---|---|
| 30 | [structure: 5-methyl-4-(prop-2-ynyloxy)-thiochroman-6-carboxylic acid S,S-dioxide] | 2.53–3.10(2H, m) 2.74(3H, s)<br>3.15–3.50(1H, m) 3.60–4.30(2H, m)<br>4.36(2H, d) 4.94–5.12(1H, m)<br>7.94(1H, d) 8.05(1H, d)<br>$CDCl_3$ |
| 31 | [structure: 5-methyl-4-(but-3-yn-2-yloxy)-thiochroman-6-carboxylic acid S,S-dioxide] | 1.49(3H, d)<br>2.31–4.52(9H, m)<br>4.78–5.32(1H, m)<br>7.86(1H, d)<br>8.55(1H, d)<br>$CDCl_3$ |
| 32 | [structure: 5-methyl-4-(2-methoxyethoxy)-thiochroman-6-carboxylic acid S,S-dioxide] | 2.74(3H, s) 2.80–3.15(2H, m)<br>3.32(3H, s) 3.25–4.20(6H, m)<br>4.81–5.00(1H, m)<br>7.78(1H, d) 7.97(1H, d)<br>$CDCl_3$ |
| 33 | [structure: 5-methyl-4-(1-methoxy-prop-2-yloxy)-thiochroman-6-carboxylic acid S,S-dioxide; 1:1 diastereomer mixture] | 1.05(1.5H, d) 1.17(1.5H, d)<br>2.25–2.70(1H, m) 2.66(1.5H, s)<br>2.70(1.5H, s) 2.85–4.21(6H, m)<br>3.31(1.5H, s) 3.40(1.5H, s)<br>5.00–5.10(0.5H, m)<br>5.13–5.23(0.5H, m)<br>7.78(1H, d) 7.94(1H, d)<br>$CDCl_3$ |

TABLE 31-continued

| Prep. Ex. No. | Starting material Comp'd of the formula (II) | NMR (ppm internal standard: TMS) |
| --- | --- | --- |
| 34 | [structure: 5-methyl-4-(cyclopropylmethoxy)-thiochroman-6-carboxylic acid S,S-dioxide] | 0.15–0.32(3H, m) 0.44–0.68(2H, m) 1.10–1.34(1H, m) 1.90–2.75(3H, m) 2.32(3H, m) 3.10–4.30(3H, m) 4.60–4.80(1H, m) 7.20(1H, d) 7.82(1H, d) CDCl$_3$ |

TABLE 32

| Prep. Ex. No. | Starting material Comp'd of the formula (II) | NMR (ppm internal standard: TMS) |
| --- | --- | --- |
| 35 | [structure: 5-chloro-8-methyl-4-(but-3-en-2-yloxy)-thiochroman-6-carboxylic acid S,S-dioxide] 1:1 diastereomer mixture | 1.27(1.5H, d) 1.34(1.5H, d) 2.35–2.74(2H, m) 2.77(3H, s) 3.18–3.42(1H, m) 3.85–4.40(2H, m) 5.12–6.10(4H, m) 7.75(1H, s) CDCl$_3$ |
| 36 | [structure: 5-chloro-8-methyl-4-(propargyloxy)-thiochroman-6-carboxylic acid S,S-dioxide] | 2.32–2.96(1H, m) 3.08(1H, t) 3.26–4.24(3H, m) 4.48(2H, d) 5.16–5.36(1H, m) 7.74(1H, s) deuteroacetone |
| 37 | [structure: 5-methyl-4-(but-3-yn-2-yloxy)-thiochroman-6-carboxylic acid S,S-dioxide] | 1.49(3H, t) 2.31–4.52(9H, m) 4.78–5.32(1H, m) 8.86(1H, d) 8.55(1H, d) deuteroacetone |
| 38 | [structure: 5-chloro-8-methyl-4-(2-methoxyethoxy)-thiochroman-6-carboxylic acid S,S-dioxide] | 2.40–2.80(2H, m) 2.75(3H, s) 3.10–3.35(1H, m) 3.39(3H, s) 3.55–4.20(5H, m) 4.86–5.06(1H, m) 7.71(1H, s) CDCl$_3$ |

TABLE 32-continued

| Prep. Ex. No. | Starting material Comp'd of the formula (II) | NMR (ppm internal standard: TMS) |
|---|---|---|
| 39 | 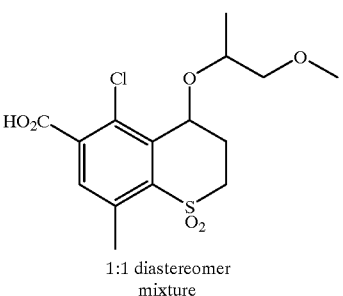<br>1:1 diastereomer mixture | 1.22(1.5H, d) 1.29(1.5H, d) 2.45–2.90(1H, m) 2.78(3H, s) 3.10–3.73(4H, m) 3.36(3H, s) 3.80–4.35(2H, m) 5.04–5.22(0.5H, m) 5.25–5.43(0.5H, m) 7.74(1H, s) $CDCl_3$ |

TABLE 33

| Prep. Ex. No. | Starting material Comp'd of the formula (II) | NMR (ppm internal standard: TMS) |
|---|---|---|
| 40 | 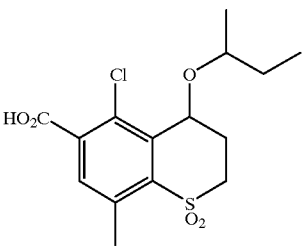 | 0.86(3H, t) 1.28(3H, d) 1.37–1.66(2H, m) 2.35–2.90(2H, m) 2.78(3H, s) 3.12–3.47(1H, m) 3.53–3.94(1H, m) 3.98–4.26(1H, m) 5.09–5.27(1H, m) 7.76(1H, s) $CDCl_3$ |
| 41 | 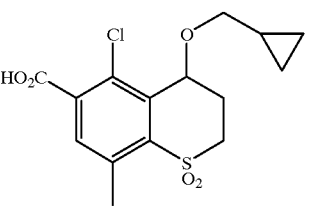 | 0.14–0.41(2H, m) 0.42–0.73(2H, m) 0.90–1.30(1H, m) 2.43–3.90(2H, m) 2.77(3H, s) 3.11–3.40(1H, m) 3.49(2H, d) 3.75–4.08(1H, m) 4.81–5.00(1H, m) 7.75(1H, s) $CDCl_3$ |
| 42 | 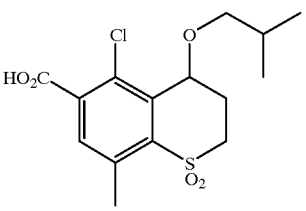 | 0.92(6H, d) 1.66–2.15(1H, m) 2.42–2.97(2H, m) 2.78(3H, s) 3.14–3.69(1H, m) 3.41(2H, d) 3.75–4.17(1H, m) 4.79–5.00(1H, m) 7.76(1H, s) $CDCl_3$ |
| 43 | 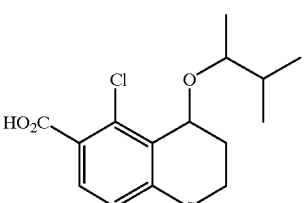<br>1:1 diastereomer mixture | 0.79(3H, d) 0.90(3H, d) 1.16(1.5H, d) 1.18(1.5H, d) 1.63–2.06(1H, m) 2.43–2.98(2H, m) 2.78(3H, s) 3.19–3.78(2H, m) 3.82–4.30(1H, m) 5.11–5.21(1H, m) 7.76(1H, s) $CDCl_3$ |

TABLE 33-continued

| Prep. Ex. No. | Starting material Comp'd of the formula (II) | NMR (ppm internal standard: TMS) |
|---|---|---|
| 44 | 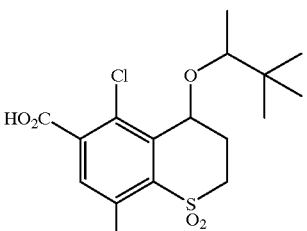<br>2:1 diastereomer mixture | 0.73(6H, s) 0.89(3H, s)<br>1.36(3H, d) 2.40–2.60(2H, m)<br>2.78(3H, s) 3.20–3.60(1H, m)<br>3.46(1H, d) 3.70–4.40(1H, m)<br>5.20–5.40(1H, m)<br>7.76(1H, s)<br>$CDCl_3$ |

TABLE 34

| Prep. Ex. No. | Starting material Comp'd of the formula (II) | NMR (ppm internal standard: TMS) |
|---|---|---|
| 45 | 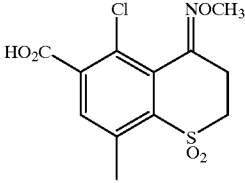 | 2.70(3H, s)<br>3.15–3.40(2H, m)<br>3.54–3.86(2H, m)<br>4.10(3H, s) 7.65(1H, s)<br>deuteroacetone |
| 46 | 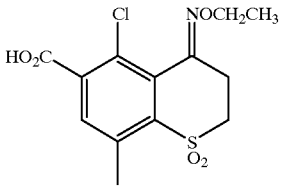 | 1.35(3H, t)<br>2.74(3H, s)<br>3.10–3.75(4H, m)<br>4.32(2H, q)<br>7.66(1H, s)<br>$CDCl_3$ |
| 47 | 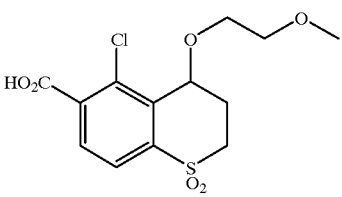 | 2.30–4.15(8H, m) 3.32(3H, s)<br>4.92–5.12(1H, m)<br>7.90(1H, d)<br>8.01(1H, d)<br>deuteroacetone |
| 48 | 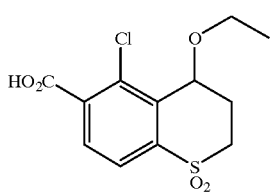 | 1.19(3H, t)<br>2.5–2.9(2H, m)<br>3.4–3.9(4H, m) 4.88–5.08(1H, m)<br>7.94(1H, d) 7.96(1H, d)<br>deuteroacetone |
| 49 | 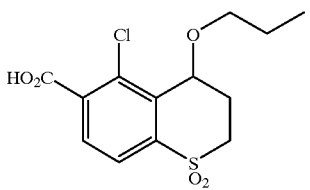 | 0.91(3H, t) 1.4–1.8(2H, m)<br>2.3–3.1(2H, m)<br>3.2–3.9(4H, m)<br>4.85–5.05(1H, m)<br>7.95(1H, d) 7.97(1H, d)<br>deuteroacetone |

TABLE 35
| Prep. Ex. No. | Starting material Comp'd of the formula (II) | NMR (ppm internal standard: TMS) |
|---|---|---|
| 50 | 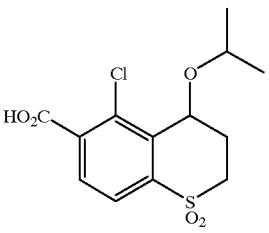<br>1:1 diastereomer mixture | 1.21(3H, d) 1.27(3H, d)<br>2.3–3.6(3H, m) 3.73(1H, dd)<br>4.06(1H, dq) 5.09–5.26(1H, m)<br>7.87(1H, d)<br>8.12(1H, d)<br>deuteroacetone |
| 51 | 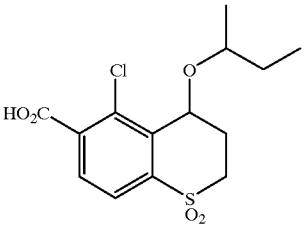 | 0.87(3H, t) 1.27(3H, d)<br>1.47–1.75(2H, m) 2.36–3.55(4H, m)<br>3.62–4.07(1H, m) 5.13–5.33(1H, m)<br>7.91(1H, d)<br>7.99(1H, d)<br>$CDCl_3$ |
| 52 | 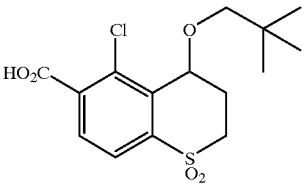 | 0.92(9H, s)<br>2.50–2.90(2H, m)<br>3.10–3.80(4H, m)<br>4.85–5.05(1H, m)<br>7.97(2H, s)<br>deuteroacetone |
| 53 | 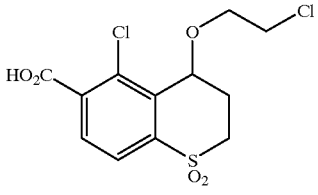 | 2.42–2.87(2H, m) 3.16–3.47(1H, m)<br>3.53–3.74(2H, m) 3.82–4.22(3H, m)<br>4.88–5.08(1H, m)<br>7.94(1H, d)<br>8.08(1H, d)<br>$CDCl_3$ |
| 54 | 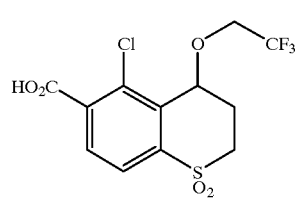 | 2.5–2.9(2H, m)<br>3.0–3.9(2H, m)<br>4.0–4.6(2H, m)<br>5.16–5.36(1H, m)<br>8.02(2H, s)<br>deuteroacetone |

TABLE 36

| Prep. Ex. No. | Starting material Comp'd of the formula (II) | NMR (ppm internal standard:TMS) |
|---|---|---|
| 55 | [structure: 5,8-dichloro-4-(1,3-difluoropropan-2-yloxy)thiochroman-6-carboxylic acid S,S-dioxide] | 2.4–3.1(2H,m)<br>3.1–4.0(2H,m)<br>4.0–4.7(3H,m)<br>4.8–5.2(2H,m)<br>5.26–5.46(1H,m)<br>7.26(1H,s)<br>deuteroacetone |
| 56 | [structure: 2-(5-chloro-4-isopropoxy-8-methyl-thiochroman-6-carbonyl)cyclohexane-1,3-dione S,S-dioxide] | 1.22(6H,d) 1.9–2.2(2H,m)<br>2.3–2.9(6H,m) 2.73(3H,s)<br>3.1–3.4(1H,m) 3.7–4.3(2H,m)<br>5.02(1H,m)<br>7.05(1H,s)<br>CDCl$_3$ |
| 57 | [structure: 2-(5-chloro-4-isopropoxy-8-methyl-thiochroman-6-carbonyl)cyclohexane-1,3-dione S,S-dioxide] | 1.22(6H,d) 1.9–2.2(2H,m)<br>2.3–2.9(6H,m) 2.73(3H,s)<br>3.1–3.4(1H,m) 3.7–4.3(2H,m)<br>5.02(1H,m)<br>7.05(1H,s)<br>CDCl$_3$ |

TABLE 37

| Prep. Ex. No. | Comp'd No. | Obtained compound | yield (%) |
|---|---|---|---|
| 1 | 1 | [structure: 2-(5-chloro-8-fluoro-4-methoxyimino-thiochroman-6-carbonyl)cyclohexane-1,3-dione S,S-dioxide] | 58 |
| 2 | 2 | [structure: 2-(5-chloro-8-fluoro-4-(2-fluoroethoxy)-thiochroman-6-carbonyl)cyclohexane-1,3-dione S,S-dioxide] | 81 |

TABLE 37-continued

| Prep. Ex. No. | Comp'd No. | Obtained compound | yield (%) |
|---|---|---|---|
| 3 | 3 | (structure) | 23 |
| 4 | 4 | (structure) | 17 |
| 5 | 5 | (structure) | 55 |

TABLE 38

| Prep. Ex. No. | Comp'd No. | Obtained compound | yield (%) |
|---|---|---|---|
| 6 | 15 | (structure) | 62 |
| 7 | 98 | (structure) | 86 |
| 8 | 104 | (structure) | 98 |

TABLE 38-continued

| Prep. Ex. No. | Comp'd No. | Obtained compound | yield (%) |
|---|---|---|---|
| 9 | 108 | (structure) | 60 |
| 10 | 6 | (structure) | 64 |

TABLE 39

| Prep. Ex. No. | Comp'd No. | Obtained compound | yield (%) |
|---|---|---|---|
| 11 | 13 | (structure) | 63 |
| 12 | 165 | (structure) | 42 |
| 13 | 202 | (structure) | 83 |
| 14 | 14 | (structure) | 62 |

TABLE 40
| Prep. Ex. No. | Comp'd No. | Obtained compound | yield (%) |
|---|---|---|---|
| 15 | 216 | 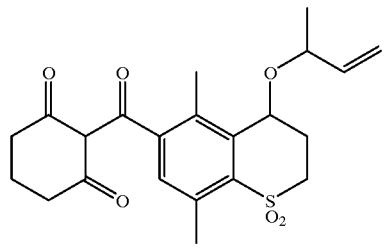 | 72 |
| 16 | 238 | 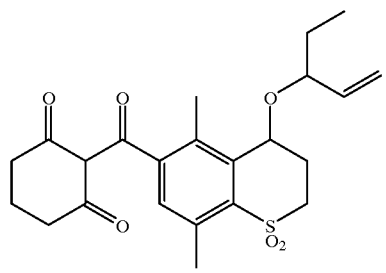 | 61 |
| 17 | 217 | 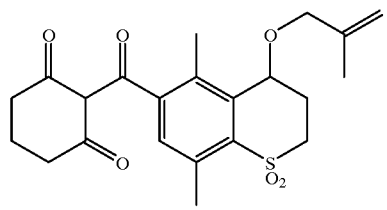 | 43 |
| 18 | 218 | 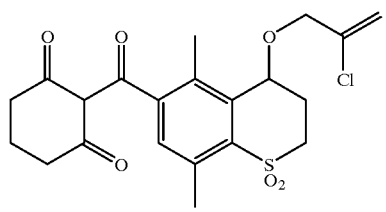 | 73 |
| 19 | 219 | 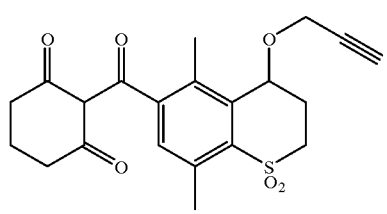 | 53 |

TABLE 41

| Prep. Ex. No. | Comp'd No. | Obtained compound | yield (%) |
|---|---|---|---|
| 20 | 220 | | 85 |
| 21 | 221 | | 52 |
| 22 | 222 | | 60 |
| 23 | 223 | | 25 |
| 24 | 224 | | 83 |

TABLE 42

| Prep. Ex. No. | Comp'd No. | Obtained compound | yield (%) |
|---|---|---|---|
| 25 | 239 | | 76 |
| 26 | 225 | | 78 |
| 27 | 226 | | 62 |
| 28 | 240 | | 82 |
| 29 | 227 | | 7 |

TABLE 43
| Prep. Ex. No. | Comp'd No. | Obtained compound | yield (%) |
|---|---|---|---|
| 30 | 228 | 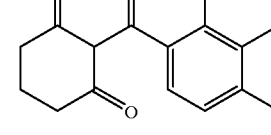 | 78 |
| 31 | 229 | 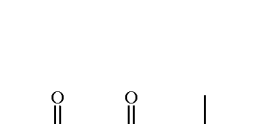 | 36 |
| 32 | 230 | 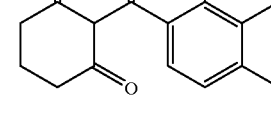 | 56 |
| 33 | 231 | 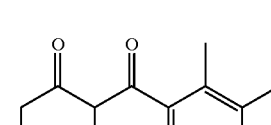 | 93 |
| 34 | 241 | 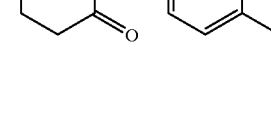 | 75 |
TABLE 44
| Prep. Ex. No. | Comp'd No. | Obtained compound | yield (%) |
|---|---|---|---|
| 35 | 232 |  | 91 |

TABLE 44-continued
| Prep. Ex. No. | Comp'd No. | Obtained compound | yield (%) |
|---|---|---|---|
| 36 | 233 | 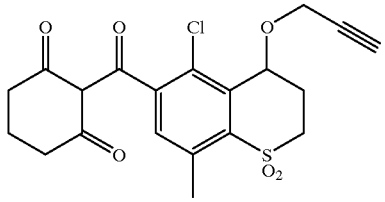 | 90 |
| 37 | 234 | 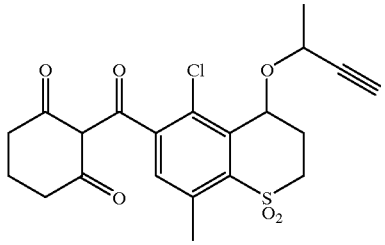 | 7 |
| 38 | 235 | 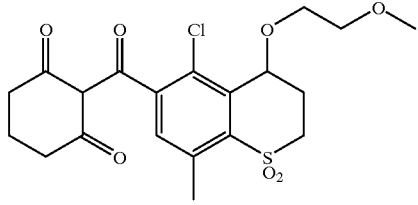 | 49 |
| 39 | 236 | 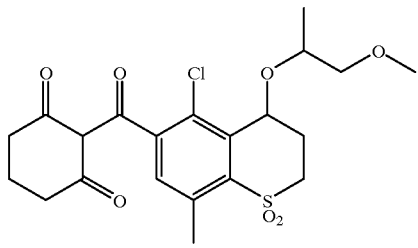 | 92 |
TABLE 45
| Prep. Ex. No. | Comp'd No. | Obtained compound | yield (%) |
|---|---|---|---|
| 40 | 16 | 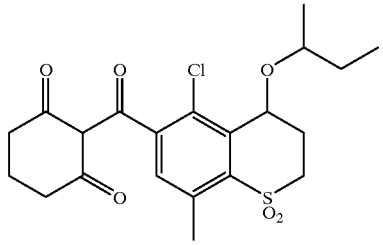 | 38 |

TABLE 45-continued
| Prep. Ex. No. | Comp'd No. | Obtained compound | yield (%) |
|---|---|---|---|
| 41 | 242 | 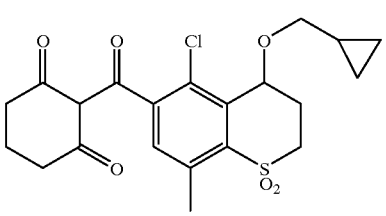 | 6 |
| 42 | 17 | 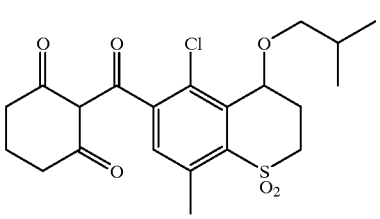 | 95 |
| 43 | 243 | 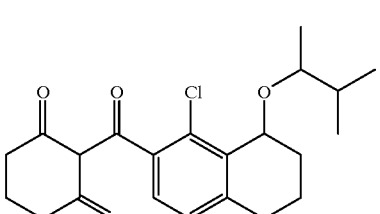 | 94 |
| 44 | 244 | 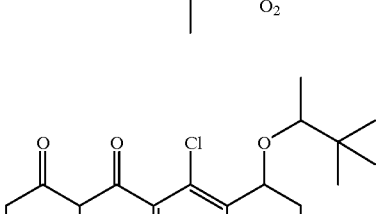 | 84 |
TABLE 46
| Prep. Ex. No. | Comp'd No. | Obtained compound | yield (%) |
|---|---|---|---|
| 45 | 168 | 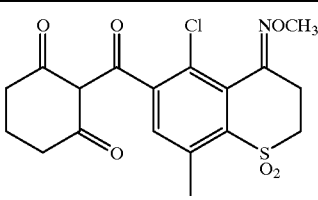 | 58 |
| 46 | 169 | 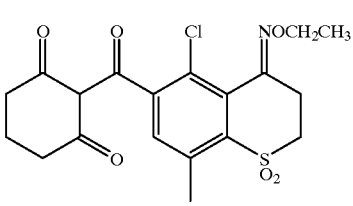 | 66 |

TABLE 46-continued

| Prep. Ex. No. | Comp'd No. | Obtained compound | yield (%) |
|---|---|---|---|
| 47 | 237 | | 9 |
| 48 | 7 | | 58 |
| 49 | 8 | | 64 |

TABLE 47

| Prep. Ex. No. | Comp'd No. | Obtained compound | yield (%) |
|---|---|---|---|
| 50 | 9 | | 70 |
| 51 | 10 | | 43 |
| 52 | 245 | | 39 |

TABLE 47-continued

| Prep. Ex. No. | Comp'd No. | Obtained compound | yield (%) |
|---|---|---|---|
| 53 | 154 | (structure: 2-[5-chloro-4-(2-chloroethoxy)-thiochroman-6-carbonyl]-cyclohexane-1,3-dione S,S-dioxide) | 20 |
| 54 | 152 | (structure: 2-[5-chloro-4-(2,2,2-trifluoroethoxy)-thiochroman-6-carbonyl]-cyclohexane-1,3-dione S,S-dioxide) | 30 |

TABLE 48

| Prep. Ex. No. | Comp'd No. | Obtained compound | yield (%) |
|---|---|---|---|
| 55 | 246 | (structure: 2-[5,8-dichloro-4-(1,3-difluoropropan-2-yloxy)-thiochroman-6-carbonyl]-cyclohexane-1,3-dione S,S-dioxide) | 30 |
| 56 | 250 | (structure: enol acetate of 2-[5-chloro-4-isopropoxy-8-methyl-thiochroman-6-carbonyl]-cyclohexane-1,3-dione S,S-dioxide) | 54 |
| 57 | 251 | (structure: triethylammonium enolate of 2-[5-chloro-4-isopropoxy-8-methyl-thiochroman-6-carbonyl]-cyclohexane-1,3-dione S,S-dioxide) | 65 |

TABLE 49

| Prep. Ex. No. | Comp'd No. | N.M.R (ppm internal standard: TMS) | IR (KBr) (cm$^{-1}$) |
|---|---|---|---|
| 1 | 1 | 2.0–2.7(6H, m) 3.4–3.5(4H, m) 4.11(3H, s) 6.06(1H, broad) 7.54(1H, d) CDCl$_3$ | 2950, 1710, 1680 1250, 1150 |
| 2 | 2 | 1.8–3.4(8H, m) 3.6–4.4(5H, m) 4.85(1H, t) 4.98(1H, broad) 7.36(1H, d) CDCl$_3$ | 2975, 1690, 1320 1170 |
| 3 | 3 | 2.0–2.8(9H, m) 2.80(3H, s) 3.0–3.4(1H, m) 3.46(3H, s) 3.6–4,1(1H, m) 4.72(1H, t) 7.06(1H, s) CDCl$_3$ | 2950, 1690, 1300 1145 |
| 4 | 4 | 1.51(6H, s) 2.0–2.8(7H, m) 2.82(3H, s) 2.70(3H, s) 3.58(2H, s) 7.16(1H, s) CDCl$_3$ | 3000, 1730, 1690 1300, 1195, 1150 |
| 5 | 5 | 1.45(6H, s) 2.0–3.0(7H, m) 2.05(3H, s) 2.70(3H, s) 3.51(2H, s) 7.07(1H, s) CDCl$_3$ | 2975, 1700, 1680 1260, 1195, 1125 |

TABLE 50

| Prep. Ex. No. | Comp'd No. | N.M.R (ppm internal standard: TMS) | IR (KBr) (cm$^{-1}$) |
|---|---|---|---|
| 6 | 15 | 1.22(6H, d) 1.9–2.2(2H, m) 2.3–2.9(6H, m) 2.73(3H, s) 3.1–3.4(1H, m) 3.7–4.3(2H, m) 5.02(1H, m) 7.05(1H, s) CDCl$_3$ | 1740, 1690, 1310, 1130 |
| 7 | 98 | 1.9–2.2(2H, m) 2.23(3H, s) 2.3–4.1(12H, m) 2.71(3H, s) 4.67(1H, m) 6.96(1H, s) CDCl$_3$ | 1750, 1690, 1300 1140 |
| 8 | 104 | 1.9–2.2(2H, m) 2.3–4.2(10H, m) 4.55(2H, m) 4.91(1H, m) 7.07(1H, s) CDCl$_3$ | 1680, 1330, 1290 1140 |
| 9 | 108 | 1.9–2.2(2H, m) 2.3–4.3(12H, m) 2.74(3H, s) 4.90(1H, m) 7.07(1H, s) CDCl$_3$ | 1680, 1290, 1120 |
| 10 | 6 | 1.9–2.2(2H, m) 2.3–3.9(8H, m) 3.49(3H, s) 4.79(1H, m) 7.48(1H, d) 7.87(1H, d) CDCl$_3$ | 16800, 1300, 1140 |

TABLE 51

| Prep. Ex. No. | Comp'd No. | N.M.R (ppm internal standard: TMS) | IR (KBr) (cm$^{-1}$) |
|---|---|---|---|
| 11 | 13 | 1.22(3H, t) 1.9–2.3(2H, m) 2.3–4.2(10H, m) 2.73(3H, s) 4.82(1H, m) 7.05(1H, s) CDCl$_3$ | 1680, 1310, 1130 |
| 12 | 165 | 1.9–2.2(2H, m) 2.3–2.6(2H, m) 2.7–3.1(2H, m) 3.3–3.7(4H, m) 4.05(3H, s) 7.46(1H, d) 7.93(1H, d) CDCl$_3$ | 1740, 1690, 1310 1160 |
| 13 | 202 | 1.48(6H, s) 1.9–2.2(2H, m) 2.35(3H, s) 2.3–2.5(2H, m) 2.7–2.9(2H, m) 3.48(2H, s) 7.32(1H, d) 7.85(1H, d) CDCl$_3$ | 1750, 1690, 1310, 1140 |
| 14 | 14 | 0.91(3H, t) 1.4–1.8(2H, m) 1.9–4.2(12H, m) 2.72(3H, s) 4.80(1H, s) 7.05(1H, s) CDCl$_3$ | 1690, 1300, 1140 |

TABLE 52

| Prep. Ex. No. | Comp'd No. | N.M.R (ppm internal standard: TMS) | IR (KBr) (cm$^{-1}$) |
|---|---|---|---|
| 15 | 216 | 1.27(3H, d) 1.90–2.90(8H, m) 2.20(3H, s) 2.75(3H, s) 3.10–3.35(1H, m) 3.70–4.20(2H, m) 4.68–4.88(1H, m) 5.10–5.36(2H, m) 5.60–6.10(1H, m) 6.93(1H, s) CDCl$_3$ | 3450, 2980, 1680 1550, 1440, 1300 1280, 1120, 1060 920, 750, 590 |
| 16 | 238 | 0.89(3H, t) 1.40–1.80(2H, m) 1.90–3.08(8H, m) 2.21(3H, s) 2.65(3H, s) 3.10–3.40(1H, m) 3.58–4.18(2H, m) 4.80–5.00(1H, m) 5.10–6.10(3H, m) 7.05(1H, s) CDCl$_3$ | 3550, 3100, 2950 1680, 1600, 1400 1300, 1130 |
| 17 | 217 | 1.75(3H, s) 2.20(3H, s) 2.61(3H, s) 2.80–3.48(8H, m) 3.51–4.33(4H, m) 4.70–4.95(2H, m) 4.89–5.15(1H, m) 6.94(1H, s) CDCl$_3$ | 3500, 3190, 2950 1580, 1400, 1280, 1120 |
| 18 | 218 | 2.11–2.87(7H, m) 2.22(3H, s) 2.77(3H, s) 3.10–3.40(1H, m) 3.70–4.10(2H, m) 4.14(2H, s) 4.62–4.82(1H, m) 5.37(1H, s) 5.51(1H, s) 6.97(1H, s) CDCl$_3$ | 2950, 1680, 1550 1410, 1310, 1280 1190, 1120, 920 750, 590, 550 |
| 19 | 219 | 1.90–2.90(8H, m) 2.27(3H, s) 2.71(3H, s) 3.05–3.45(1H, m) 3.65–4.34(2H, m) 4.29(2H, d) 4.86–5.05(1H, m) 6.96(1H, s) CDCl$_3$ | 3450, 3290, 2950 1680, 1550, 1440 1310, 1120, 1060 920, 790, 750, 590 |

TABLE 53

| Prep. Ex. No. | Comp'd No. | N.M.R (ppm internal standard: TMS) | IR (KBr) (cm$^{-1}$) |
|---|---|---|---|
| 20 | 220 | 1.48(3H, d) 1.90–2.95(6H, m) 2.04(2H, t) 2.22(0.9H, s) 2.31(2.1H, s) 2.53(1H, d) 2.71(3H, s) 3.10–3.35(1H, m) 3.55–4.50(2H, m) 4.75–4.95(0.3H, m) 5.05–5.20(0.7H, m) 6.95(1H, s) 7:3 diastereomer mixture CDCl$_3$ | 3300, 3275, 3000 2945, 2900, 1680 1590, 1440, 1410 1300, 1280, 1190 1120, 1090, 1050 |
| 21 | 221 | 1.87(3H, t) 1.90–2.90(7H, m) 2.26(3H, s) 2.70(3H, s) 3.05–3.35(1H, m) 3.65–4.35(2H, m) 4.35(2H, d) 4.82–5.00(1H, m) 6.93(1H, s) CDCl$_3$ | 3460, 2960, 1740 1690, 1595, 1450 1390, 1310, 1290 1250, 1195, 1130 1060, 920, 760 |

TABLE 53-continued

| Prep. Ex. No. | Comp'd No. | N.M.R (ppm internal standard: TMS) | IR (KBr) (cm$^{-1}$) |
|---|---|---|---|
| 22 | 222 | 1.90–2.95(10H, m) 2.23(3H, s) 2.71(3H, s) 3.05–3.35(1H, m) 3.40–4.25(4H, m) 4.54–4.74(1H, m) 6.95(1H, s) CDCl$_3$ | 3390, 2950, 1730 1680, 1565, 1440 1310, 1290, 1120 1080, 920, 750 |
| 23 | 223 | 1.53(8H, m) 2.24(3H, s) 2.71(3H, s) 3.10–3.30(1H, m) 3.36(3H, s) 3.51–3.93(5H, m) 4.54–4.74(1H, m) 6.94(1H, s) CDCl$_3$ | 2940, 1670, 1540 1440, 1410, 1300 1280, 1180, 1120 1070, 910, 740 |
| 24 | 224 | 1.18(1.5H, d) 1.21(1.5H, d) 1.70–2.20(3H, m) 2.25–2.55(2H, m) 2.26(1.5H, s) 2.31(1.5H, s) 2.60–2.90(3H, m) 2.72(3H, s) 3.00–3.60(3H, m) 3.31(1.5H, s) 3.34(1.5H, s) 3.70–4.30(2H, m) 4.70–4.90(0.5H, m) 5.00–5.15(0.5H, m) 6.93(1H, s) 1:1 diastereomer mixture CDCl$_3$ | 2950, 1680, 1570 1560, 1300, 1280 1120, 1045, 920 750 |

TABLE 54

| Prep. Ex. No. | Comp'd No. | N.M.R (ppm internal standard: TMS) | IR (KBr) (cm$^{-1}$) |
|---|---|---|---|
| 25 | 239 | 1.50–2.90(12H, m) 2.23(3H, s) 2.71(3H, s) 3.05–3.30(1H, m) 3.40–4.20(6H, m) 4.50–4.70(1H, m) 6.94(1H, s) CDCl$_3$ | 2950, 2880, 1785 1560, 1310, 1290 1190, 1125, 1075 920, 760, 600, 550 |
| 26 | 225 | 1.9–2.9(8H, m) 2.28(3H, s) 3.1–3.4(1H, m) 3.8–4.4(4H, m) 3.5–4.2(3H, m) 4.7–4.9(1H, m) 5.93(1H, t) 6.99(1H, s) CDCl$_3$ | 2980, 1740, 4680 1560, 1420, 1310 1290, 1190, 1130 1050, 920, 790 760 |
| 27 | 226 | 1.9–2.9(8H, m) 2.19(3H, s) 2.72(3H, s) 3.1–3.4(1H, m) 3.5–4.2(3H, m) 4.7–4.9(1H, m) 5.93(1H, t) 6.99(1H, s) CDCl$_3$ | 2950, 1730, 1680 1560, 1410, 1310 1290, 1240, 1190 1120, 1100, 920 840, 790, 760 |
| 28 | 240 | 0.10–0.30(2H, m) 0.45–0.65(2H, m) 0.90–1.25(1H, m) 1.90–2.90(8H, m) 2.23(3H, s) 2.70(3H, s) 3.05–3.60(3H, m) 3.65–4.05(1H, m) 4.50–4.67(1H, m) 6.93(1H, s) CDCl$_3$ | 2980, 1690, 1560 1420, 1320, 1300 1200, 1140, 1080 935, 765, 600 560 |
| 29 | 227 | 1.2–1.4(3H, d) 1.8–2.9(10H, m) 3.1–3.4(1H, m) 3.6–4.2(3H, m) 4.6–4.9(1H, m) 5.0–5.9(3H, m) 7.16(1H, d) 7.80(1H, d) CDCl$_3$ | 2970, 1590, 1400, 1315, 4295, 1200, 1130 |

TABLE 55

| Prep. Ex. No. | Comp'd No. | N.M.R (ppm internal standard: TMS) | IR (KBr) (cm$^{-1}$) |
|---|---|---|---|
| 30 | 228 | 1.90–2.90(8H, m) 2.32(3H, s) 3.10–3.40(1H, m) 3.60–4.20(2H, m) 4.31(2H, d) 4.88–5.08(1H, m) 7.21(1H, d) 7.81(1H, d) CDCl$_3$ | 3370, 2950, 1680 1550, 1410, 1310 1280, 1180, 1120 1060, 750 |
| 31 | 229 | 1.47(3H, d) 1.85–2.90(8H, m) 2.25(3H, s) 3.05–4.40(4H, m) 4.80–5.00(0.5H, m) 5.10–5.30(0.5H, m) 7.21(1H, d) 7.83(1H, d) CDCl$_3$ | 3280, 2950, 1680 1550, 1420, 1300 1290, 1190, 1120 1090, 1050, 910 750, 590 |

TABLE 55-continued

| Prep. Ex. No. | Comp'd No. | N.M.R (ppm internal standard: TMS) | IR (KBr) (cm$^{-1}$) |
|---|---|---|---|
| 32 | 230 | 2.00–3.10(8H, m) 2.30(3H, s) 3.10–3.30(1H, m) 3.30(3H, s) 3.42–3.95(5H, m) 4.73–4.93(1H, m) 7.31(1H, d) 7.70(1H, d) CDCl$_3$ | 3450, 2900, 1680 1550, 1430, 1280 1130, 1080 |
| 33 | 231 | 1.14–1.26(3H, m) 1.90–3.65(14H, m) 3.32(3H, s) 3.72–4.10(2H, m) 4.75–4.95(0.5H, m) 5.00–5.20(0.5H, m) 7.19(1H, d) 7.80(1H, d) 1:1 diastereomer mixture CDCl$_3$ | 3480, 2950, 1730 1670, 1410, 1300 1190, 1120, 1040 970, 910, 750 600, 550 |
| 34 | 241 | 0.15–0.32(2H, m) 0.44–0.68(2H, m) 1.10–1.34(1H, m) 1.90–2.80(9H, m) 2.30(3H, s) 3.10–4.30(3H, m) 4.55–4.75(1H, m) 7.20(1H, d) 7.82(1H, d) CDCl$_3$ | 2960, 1730, 1610 1410, 1290, 1190 1120, 1050, 910 800, 750 |

TABLE 56

| Prep. Ex. No. | Comp'd No. | N.M.R (ppm internal standard: TMS) | IR (KBr) (cm$^{-1}$) |
|---|---|---|---|
| 35 | 232 | 1.24(1.5H, d) 1.28(1.5H, d) 1.90–2.90(8H, m) 2.79(3H, s) 3.10–3.40(1H, m) 3.70–4.35(2H, m) 4.95–5.40(3H, m) 5.60–6.15(1H, m) 7.05(1H, s) 1:1 diastereomer Mixture CDCl$_3$ | 3020, 2980, 1690 1580, 1320, 1300 1150, 1080, 930 760 |
| 36 | 233 | 2.00–2.95(8H, m) 2.73(3H, s) 3.15–3.35(1H, m) 3.83–4.40(2H, m) 4.34(2H, d) 5.00–5.20(1H, m) 7.07(1H, s) CDCl$_3$ | 3380, 2960, 1740 1680, 1570, 1420 1310, 1290, 1130 1060, 910, 740 590 |
| 37 | 234 | 1.43(1.5H, d) 1.48(1.5H, d) 1.8–2.2(4H, m) 2.3–2.8(6H, m) 2.71(3H, s) 3.0–3.4(1H, m) 3.6–4.1(1H, m) 5.02–5.15(0.5H, m) 5.35–5.45(0.5H, m) 7.07(1H, s) CDCl$_3$ | 2980, 1600, 1400 1320, 1300, 1145 1110, 1070, 920 750 |
| 38 | 235 | 1.95–2.70(8H, m) 2.73(3H, s) 3.00–4.20(6H, m) 3.35(3H, s) 4.77–4.97(1H, m) 7.05(1H, s) CDCl$_3$ | 3460, 2940, 1680 1410, 1290, 1130 1070, 910, 740 590, 550 |
| 39 | 236 | 1.20(1.5H, d) 1.23(1.5H, d) 1.80–2.86(7H, m) 2.73(3H, s) 2.90–3.68(4H, m) 3.34(3H, s) 3.76–4.42(2H, m) 5.00–5.15(0.5H, m) 5.15–5.35(0.5H, m) 7.05(1H, s) 1:1 diastereomer mixture CDCl$_3$ | 3540, 2940, 1680 1560, 1410, 1310 1290, 1130, 1050 980, 910, 740 590 |

TABLE 57

| Prep. Ex. No. | Comp'd No. | N.M.R (ppm internal standard: TMS) | IR (KBr) (cm$^{-1}$) |
|---|---|---|---|
| 40 | 16 | 0.84(3H, t) 1.19(3H, d) 1.34–1.68(2H, m) 1.96–2.10(2H, m) 2.27–2.93(6H, m) 2.73(3H, s) 3.85–4.26(1H, m) 3.06–3.40(1H, m) 3.45–3.78(1H, m) 3.85–4.26(1H, m) 5.00–5.10(1H, m) 7.04(1H, s) 1:1 diastereomer mixture | 3000, 2970, 2900 1740, 1690, 1570 1420, 1390, 1310 1290, 1160, 1140 1060, 1000, 920 |

TABLE 57-continued

| Prep. Ex. No. | Comp'd No. | N.M.R (ppm internal standard: TMS) | IR (KBr) (cm$^{-1}$) |
|---|---|---|---|
| 41 | 242 | CDCl$_3$<br>0.2–0.4(2H, m) 0.5–0.7(2H, m)<br>1.2–1.6(1H, m) 1.8–2.2(2H, m)<br>2.3–2.8(6H, m) 2.71(3H, s)<br>2.92(2H, d) 3.0–3.6(2H, m)<br>4.7–4.9(1H, m) 7.03(1H, s)<br>CDCl$_3$ | 2980, 1625, 1400<br>1320, 1300, 1190<br>11401080, 760 |
| 42 | 17 | 0.90(6H, d) 1.70–1.93(1H, m)<br>1.97–2.19(2H, m) 2.37–2.87(6H, m)<br>2.73(3H, s) 3.06–3.26(1H, m)<br>3.35(2H, d) 3.75–4.08(1H, m)<br>4.68–4.88(1H, m) 7.05(1H, s)<br>CDCl$_3$ | 2980, 2900, 1680<br>1580, 1420, 1310<br>1140, 1080, 920<br>750, 590 |
| 43 | 243 | 0.79(3H, d) 0.89(3H, d) 1.13(3H, d)<br>1.65–2.19(3H, m) 2.28–2.94(6H, m)<br>2.74(3H, s) 3.16–3.65(2H, m)<br>3.82–4.29(1H, m) 5.00–5.15(1H, m)<br>7.05(1H, s)<br>CDCl$_3$ | 2980, 2900, 1680<br>1580, 1420, 1310<br>1140, 1080, 920<br>750, 590 |
| 44 | 244 | 0.73(6H, s) 0.88(3H, s) 1.15(3H, d)<br>1.90–2.90(8H, m) 2.78(3H, s)<br>3.10–3.55(2H, m) 3.75–4.45(1H, m)<br>5.13(1H, broad) 7.05(1H, s)<br>CDCl$_3$ | 3000, 2900, 1690<br>1580, 1430, 1390<br>1320, 1300, 1140<br>1100, 1060, 920<br>850 |

TABLE 58

| Prep. Ex. No. | Comp'd No. | N.M.R (ppm internal standard: TMS) | IR (KBr) (cm$^{-1}$) |
|---|---|---|---|
| 45 | 168 | 2.20–3.15(6H, m) 2.64(3H, s)<br>3.20–3.39(2H, m) 3.51–3.70(2H, m)<br>4.01(3H, s)<br>7.19(1H, s)<br>deuteroacetone | 2950, 1665, 1550<br>1410, 1315, 1280<br>1160, 1040, 935<br>740, 590, 550 |
| 46 | 169 | 1.32(3H, t) 1.90–2.95(6H, m)<br>2.70(3H, s) 3.20–3.51(4H, m)<br>4.29(2H, q)<br>7.00(1H, s)<br>CDCl$_3$ | 3550, 2980, 2950<br>1730, 1680, 1560<br>1410, 1320, 1150<br>1040 |
| 47 | 237 | 1.90–4.15(14H, m)<br>3.29(3H, s)<br>4.82–5.00(1H, m)<br>7.50(1H, d) 7.85(1H, d)<br>CDCl$_3$ | 3450, 2950, 1680<br>1560, 1400, 1310<br>1130 |
| 48 | 7 | 1.8–2.3(2H, m) 2.4–3.0(4H, m)<br>3.2–4.1(6H, m) 4.8–5.0(1H, m)<br>7.31(1H, d)<br>7.90(1H, d)<br>CDCl$_3$ | 2920, 1660, 1590<br>1470, 1395, 1140<br>880, 750 |
| 49 | 8 | 0.91(3H, t) 1.8–2.2(2H, m)<br>2.3–2.9(6H, m) 3.1–4.0(6H, m)<br>4.70–4.92(1H, m) 7.31(1H, d)<br>7.89(1H, d)<br>CDCl$_3$ | 3000, 1660, 1600<br>1350, 1330, 1150<br>1100, 920, 880 |

TABLE 59

| Prep. Ex. No. | Comp'd No. | N.M.R (ppm internal standard: TMS) | IR (KBr) (cm$^{-1}$) |
|---|---|---|---|
| 50 | 9 | 1.22(6H, d) 1.86–2.25(2H, m)<br>2.30–2.90(6H, m) 3.10–3.40(1H, m)<br>3.70–4.20(2H, m) 4.99(1H, m)<br>7.30(1H, d) 7.89(1H, d)<br>CDCl$_3$ | 3500, 3000, 1680<br>1600, 1420, 1320,<br>1150, 1060 |
| 51 | 10 | 0.85(3H, t) 1.21(3H, d)<br>1.42–1.72(2H, m) 1.94–2.22(2H, m)<br>2.37–2.98(6H, m) 3.07–3.42(1H, m)<br>3.54–4.06(2H, m) 4.92–5.12(1H, m)<br>7.30(1H, d) 7.91(1H, d)<br>CDCl$_3$ | 3470, 3000, 2960<br>2900, 1690, 1570<br>1420, 1320, 1300<br>1160, 1140, 1060<br>1000, 950, 750 |
| 52 | 245 | 0.90(9H, s) 2.2–2.9(8H, m)<br>3.1–3.9(4H, m) 4.70–4.90(1H, m)<br>7.33(1H, d)<br>7.89(1H, d)<br>CDCl$_3$ | 3400, 2995, 2990<br>1695, 1580, 1330<br>1150, 1095, 1020 |
| 53 | 154 | 1.92–2.22(2H, m) 2.30–3.04(6H, m)<br>3.13–3.42(1H, m) 3.56–3.73(2H, m)<br>3.77–4.18(3H, m) 4.78–4.95(1H, m)<br>7.32(1H, d) 7.92(1H, d)<br>CDCl$_3$ | 3460, 2960, 1740<br>1680, 1590, 1570<br>1420, 1340, 1320<br>1300, 1160, 1140,<br>1110, 760 |
| 54 | 152 | 2.2–3.0(8H, m) 3.2–3.4(1H, m)<br>3.7–4.1(3H, m) 4.93–5.08(1H, m)<br>7.93(1H, d)<br>7.36(1H, d)<br>CDCl$_3$ | 3360, 2975, 1690<br>1420, 1300, 1150<br>1020, 980, 920<br>840, 750 |

TABLE 60

| Prep. Ex. No. | Comp'd No. | N.M.R (ppm internal standard: TMS) | IR (KBr) (cm$^{-1}$) |
|---|---|---|---|
| 55 | 246 | 2.2–3.0(8H, m) 3.2–3.5(1H, m)<br>3.8–4.5(4H, m) 4.6–5.0(2H, m)<br>5.1–5.3(1H, m)<br>7.31(1H, s)<br>CDCl$_3$ | 3400, 2975, 2900<br>1690, 1580, 1345<br>1320, 1300, 1200<br>1140, 1100, 1080<br>920, 750 |
| 56 | 250 | 1.98–2.20(2H, m) 2.29–2.95(6H, m)<br>2.74(3H, s) 3.06–3.42(1H, m)<br>3.51–3.77(2H, m) 3.80–4.26(3H, m)<br>4.80–5.00(1H, m) 7.07(1H, s)<br>CDCl$_3$ | 2950, 1740, 1680<br>1570, 1310, 1290<br>1150, 1130, 1070<br>910, 750, 590,<br>550 |
| 57 | 251 | 0.91(3H, t) 1.48–1.81(2H, m)<br>1.97–2.18(8H, m) 2.26–2.87(6H, m)<br>2.72(3H, s) 3.09–3.35(1H, m)<br>3.46–3.61(2H, m) 3.77–4.17(1H, m)<br>4.70–4.90(1H, m) 7.05(1H, s)<br>CDCl$_3$ | 2970, 2950, 2880<br>1680, 1580, 1560<br>1410, 1310, 1290<br>1150, 1130, 1070<br>910, 740, 590,<br>540 |

Herbicide Examples (1) Preparation of herbicides

97 Parts by weight of talc (trade name: Zeaklite, supplied by Zeaklite Industry) as a carrier, 1.5 parts by weight of alkylarylsulfonic acid salt(trade name: Neoplex, supplied by Kao-Atlas K.K.) as a surfactant and 1.5 parts by weight of a nonionic and anionic surfactant (trade name: Sorpol 800A, supplied by Toho Chemical Co., Ltd.) were uniformly pulverized and mixed to prepare a carrier for a wettable powder.

90 Parts by weight of the above carrier for a wettable powder and 10 parts by weight of one of the compounds of the of the present invention were uniformly pulverized and mixed to obtain herbicides. Further, in Comparative Herbicide Examples, comparative herbicides were also prepared from the following compounds (A) to (G) in the same manner.

(A) 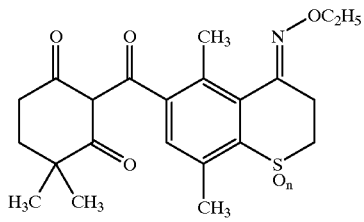

(B) 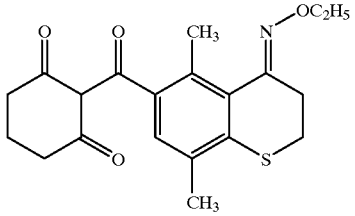

(C) 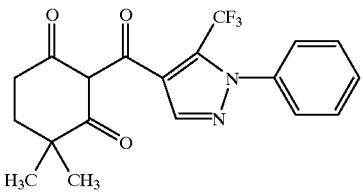

(D) 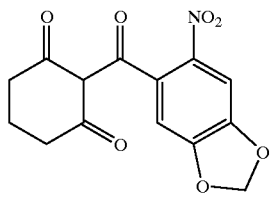

(E) 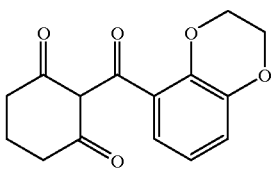

(F) 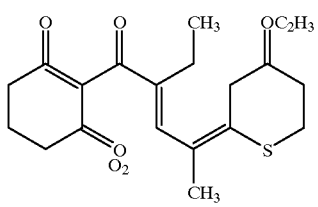

(G) 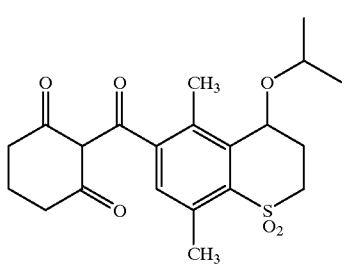

The compounds (A) and (B) are disclosed in WO94/08988, the compounds (C), (D) and (E) are disclosed in European Patent 94/283261, and the compounds (F) and (G) are disclosed in WO94/04524.

(2) Ratings of evaluation of herbicidal efficacy and phytotoxicity to crops

The ratio of remaining plant weight to plant weight in non-treated plot was determined on the basis of the ratio of remaining plant weight to plant weight in non-treated plot= (remaining plant weight in treated plot/plant weight in non-treated plot)×100. The ratings were applied to the following biological tests.

| Ratings | Ratio of remaining plant weight to plant weight in non-treated plot (%) |
|---|---|
| Herbicidal efficacy | |
| 0 | 81–100 |
| 1 | 61–80 |
| 2 | 41–60 |
| 3 | 21–40 |
| 4 | 1–20 |
| 5 | 0 |
| Phytotoxicity to crops | |
| – | 100 |
| ± | 95–99 |
| + | 90–94 |
| ++ | 80–89 |
| +++ | 0–79 |

(3) Biological tests (a) Upland pre-emergence treatment test 1

An upland pre-emergence treatment test was carried out in the following manner with regard to Compounds Nos. 1 to 5 (Examples) and Compounds (A) to (E) (Comparative Examples).

Seeds of weeds such as velvetleaf, Jimsonweed, black nightshade, barnyardgrass and large crabgrass and seeds of corn, sorgo and cotton were sown in 1/5,000-are Wagner pots filled with upland soil, and covered with upland soil. Then, a predetermined amount of the herbicide prepared in the above (1) was suspended in water and uniformly sprayed onto the soil surface. Then, the seeds were grown in a greenhouse, and on the 20th day after the treatment, the herbicide was evaluated for herbicidal efficacy and phytotoxicity to the crops on the basis of the ratings shown in (2). Table 61 shows the results.

TABLE 61

| Com'd No. | Dosage (g/ha) | Herbicidal efficacy | | | | | Phytotoxicity | | |
|---|---|---|---|---|---|---|---|---|---|
| | | AA | BB | CC | DD | EE | FF | GG | HH |
| 1 | 300 | 5 | 5 | 5 | 3 | 0 | – | – | – |
| 2 | 300 | 5 | 5 | 5 | 4 | 3 | – | – | – |
| 3 | 300 | 5 | 5 | 5 | 5 | 5 | – | – | – |
| 4 | 100 | 5 | 5 | 5 | 0 | 0 | – | – | – |
| 5 | 300 | 5 | 5 | 5 | 0 | 3 | – | – | – |
| A | 300 | 5 | 5 | 5 | 3 | 1 | – | ++ | ++ |
| B | 300 | 1 | 0 | 0 | 0 | 0 | – | – | – |
| C | 300 | 0 | 1 | 1 | 0 | 0 | – | – | – |

TABLE 61-continued

| Com'd | Dosage | Herbicidal efficacy | | | | | Phytotoxicity | | |
|---|---|---|---|---|---|---|---|---|---|
| No. | (g/ha) | AA | BB | CC | DD | EE | FF | GG | HH |
| D | 300 | 1 | 0 | 1 | 0 | 0 | – | – | – |
| E | 300 | 0 | 0 | 0 | 0 | 0 | – | – | – |

AA = Velvetleaf, BB = Jimsonweed, CC = Black nightshade, DD = Barnyardgrass, EE = Large crabgrass, FF = Corn, GG = Sorgo, HH = Cotton Table 61 shows that the herbicides of the present invention can selectively control a broad range of upland soil weeds at a low dosage without causing phytotoxicity on corn, sorgo and cotton. In contrast, it is also shown that Compound A is poor in safety to sorgo and cotton, and that Compounds B to E are all poor in the efficacy on all the test weeds.

(b) Upland post-emergence treatment test 1

An upland post-emergence treatment test was carried out in the following manner with regard to Compounds Nos. 1 to 5 (Examples) and Compounds (A), (C), (D) and (E) (Comparative Examples).

Seeds of weeds such as cocklebur, velvetleaf, Jimsonweed, barnyardgrass and large crabgrass and seeds of corn, sorgo and beet were sown in 1/5,000-are Wagner pots filled with upland soil, and covered with upland soil. The seeds were grown in a greenhouse, and at the stage of 3~4 leaves of these plants, a predetermined amount of the herbicide prepared in the above (1) was suspended in water and uniformly sprayed onto leaf and stalk portions at a rate of 2,000 l/ha. Then, the plants were grown in the greenhouse, and on the 30th day after the treatment, the herbicide was evaluated for herbicidal efficacy and phytotoxicity to the crops on the basis of the ratings shown in (2) Table 62 shows the results.

TABLE 62

| Com'd | Dosage | Herbicidal efficacy | | | | | Phytotoxicity | | |
|---|---|---|---|---|---|---|---|---|---|
| No. | (g/ha) | AA | BB | CC | DD | EE | FF | GG | HH |
| 1 | 300 | 5 | 5 | 4 | 0 | 0 | – | – | – |
| 2 | 300 | 5 | 5 | 5 | 4 | 4 | – | – | ± |
| 3 | 300 | 5 | 5 | 3 | 3 | 3 | – | – | ± |
| 4 | 100 | 4 | 5 | 5 | 4 | 3 | – | – | ± |
| 5 | 300 | 5 | 4 | 2 | 4 | 3 | – | – | – |
| A | 300 | 5 | 5 | 5 | 4 | 0 | – | ++ | +++ |
| C | 300 | 5 | 0 | 5 | 0 | 1 | – | ++ | +++ |
| D | 300 | 5 | 4 | 5 | 0 | 1 | – | ++ | +++ |
| E | 300 | 0 | 0 | 0 | 0 | 0 | – | – | – |

AA = Cocklebur, BB = Velvetleaf, CC = Jimsonweed, DD = Barnyardgrass, EE = Large crabgrass, FF = Corn, GG = Sorgo, HH = Beet Table 62 shows that the herbicides of the present invention show no phytotoxicity on corn and sorgo, has selectivity for beet and further can selectively control a broad range of upland soil weeds at a low dosage. In contrast, it is also shown that Compounds A, C and D are poor in safety to sorgo and beet and that Compound E is poor in efficacy on all the test weeds.

(c) Upland pre-emergence treatment-test 2

An upland pre-emergence treatment test was carried out in the following manner with regard to Compounds Nos. 6, 15, 104 and 165 (Examples) and Compound (F) (Comparative Example).

Seeds of weeds such as velvetleaf, black nightshade, barnyardgrass, large crabgrass and giant foxtail and seeds of corn and cotton were sown in 1/5,000-are Wagner pots filled with upland soil, and covered with upland soil. Then, a predetermined amount of the herbicide prepared in the above (1) was suspended in water and uniformly sprayed onto the soil surface. Then, the seeds were grown in a greenhouse, and on the 20th day after the treatment, the herbicide was evaluated for herbicidal efficacy and phytotoxicity to the crops on the basis of the ratings shown in (2). Table 63 shows the results.

TABLE 63

| Com'd | Dosage | Herbicidal efficacy | | | | | Phytotoxicity | |
|---|---|---|---|---|---|---|---|---|
| No. | (g/ha) | AA | BB | CC | DD | EE | FF | GG |
| 6 | 100 | 5 | 5 | 3 | 5 | 3 | – | – |
| 15 | 100 | 5 | 5 | 5 | 4 | 4 | – | – |
| 104 | 100 | 5 | 5 | 4 | 5 | 4 | – | – |
| 165 | 100 | 5 | 5 | 5 | 5 | 3 | – | – |
| F | 100 | 5 | 5 | 0 | 1 | 0 | – | – |

AA = Velvetleaf, BB = Black nightshade, CC = Barnyardgrass, DD = Large crabgrass, EE = Giant foxtail, FF = Corn, GG = Cotton Table 62 shows that the herbicides of the present invention cause no phytotoxicity on corn and cotton and can selectively control a broad range of upland soil weeds at a low dosage. In contrast, it is shown that Compound F is poor in efficacy on grass weeds.

(d) Upland post-emergence treatment test 2

An upland post-emergence treatment test was carried out in the following manner with regard to Compounds Nos. 15, 104, 165 and 202 (Examples) and Compound (F) (Comparative Example).

Seeds of weeds such as cocklebur, velvetleaf, black nightshade, barnyardgrass, large crabgrass and giant foxtail and seeds of corn and sorgo were sown in 1/5,000-are Wagner pots filled with upland soil, and covered with upland soil. The seeds were grown in a greenhouse, and at the stage of 3~4 leaves of these plants, a predetermined amount of the herbicide prepared in the above (1) was suspended in water and uniformly sprayed onto leaf and stalk portions at a rate of 2,000 l/ha. Then, the plants were grown in the greenhouse, and on the 30th day after the treatment, the herbicide was evaluated for herbicidal efficacy and phytotoxicity to the crops on the basis of the ratings shown in (2). Table 64 shows the results.

TABLE 64

| Com'd | Dosage | Herbicidal efficacy | | | | | Phytotoxicity | | |
|---|---|---|---|---|---|---|---|---|---|
| No. | (g/ha) | AA | BB | CC | DD | EE | FF | GG | HH |
| 15 | 100 | 5 | 5 | 5 | 5 | 4 | 5 | – | – |
| 104 | 100 | 5 | 5 | 5 | 4 | 4 | 3 | – | – |
| 165 | 100 | 5 | 5 | 5 | 5 | 4 | 4 | – | – |
| 202 | 100 | 5 | 5 | 5 | 4 | 4 | 3 | – | – |
| F | 100 | 5 | 5 | 5 | 0 | 0 | 0 | – | – |

AA = Cocklebur, BB = Velvetleaf, CC = Black nightshade, DD = Barnyardgrass, EE = Large crabgrass, FF = Giant foxtail, GG = Corn, HH = Cotton Table 64 shows that the herbicides of the present invention do not cause phytotoxicity on corn and sorgo and can selectively control a broad range of upland soil weeds at a low dosage. In contrast, it is shown that Compound F is poor in efficacy on grass weeds.

(e) Upland post-emergence treatment test 3

An upland post-emergence treatment test was carried out in the following manner with regard to Compound No. 15 (Example) and Compound (G) (Comparative Example).

Seeds of weeds such as velvetleaf, common ragweed, barnyardgrass and giant foxtail and seeds of corn and sorgo were sown in 1/5,000-are Wagner pots filled with upland soil, and covered with upland soil. The seeds were grown in a greenhouse, and at the stage of 3~4 leaves of these plants, a predetermined amount of the herbicide prepared in the above (1) was suspended in water and uniformly sprayed onto leaf and stalk portions at a rate of 2,000 l/ha. Then, the plants were grown in the greenhouse, and on the 30th day after the treatment, the herbicide was evaluated for herbicidal efficacy and phytotoxicity to the crops on the basis of the ratings shown in (2). Table 65 shows the results.

TABLE 65

| Com'd No. | Dosage (g/ha) | Herbicidal efficacy | | | | Phytotoxicity | |
|---|---|---|---|---|---|---|---|
| | | AA | BB | CC | DD | EE | FF |
| 15 | 50 | 5 | 5 | 5 | 5 | – | – |
| G | 50 | 5 | 2 | 1 | 0 | – | – |

AA = Velvetleaf, BB = Common ragweed, CC = Barnyardgrass, DD = Giant foxtail, EE = Corn, GG = Sorgo Table 65 shows that the herbicide of the present invention causes no phytotoxicity on corn and sorgo and further that it can selectively control main upland soil weeds at a low dosage. In contrast, it is shown that Compound G is poor in efficacy on common ragweed, barnyardgrass and giant foxtail which are mainly to be controlled in upland fields.

(f) Upland post-emergence treatment test 4

An upland post-emergence treatment test was carried out in the following manner with regard to Compounds Nos. 7 to 9, 16, 17, 154, 168, 169, 216 to 244, 250 and 251 (Examples) and Compound (F) (Comparative Example).

Seeds of weeds such as cocklebur, velvetleaf, common lambsquaters, common ragweed, large crabgrass and green foxtail and seeds of corn were sown in 1/5,000-are Wagner pots filled with upland soil, and covered with upland soil. The seeds were grown in a greenhouse, and at the stage of 3~4 leaves of these plants, a predetermined amount of the herbicide prepared in the above (1) was suspended in water and uniformly sprayed onto leaf and stalk portions at a rate of 2,000 l/ha. Then, the plants were grown in the greenhouse, and on the 30th day after the treatment, the herbicide was evaluated for herbicidal efficacy and phytotoxicity to the crop on the basis of the ratings shown in (2). Table 66 shows the results.

TABLE 66

| Com'd No. | Dosage (g/ha) | Herbicidal efficacy | | | | | | Phytotoxicity |
|---|---|---|---|---|---|---|---|---|
| | | AA | BB | CC | DD | EE | FF | Corn |
| 7 | 300 | 5 | 5 | 5 | 5 | 5 | 4 | – |
| 8 | 300 | 5 | 5 | 5 | 5 | 4 | 4 | – |
| 9 | 300 | 5 | 5 | 5 | 5 | 4 | 4 | – |
| 16 | 300 | 5 | 5 | 5 | 5 | 5 | 5 | – |
| 17 | 300 | 5 | 5 | 5 | 5 | 5 | 5 | – |
| 154 | 300 | 4 | 5 | 5 | 5 | 5 | 4 | – |
| 168 | 300 | 5 | 5 | 5 | 5 | 5 | 5 | ± |
| 169 | 300 | 5 | 5 | 5 | 5 | 5 | 5 | ± |
| 216 | 300 | 5 | 5 | 5 | 5 | 5 | 5 | – |
| 217 | 300 | 5 | 5 | 5 | 5 | 4 | 4 | – |
| 218 | 300 | 5 | 5 | 5 | 5 | 5 | 5 | – |
| 219 | 300 | 5 | 5 | 5 | 5 | 5 | 5 | – |
| 220 | 300 | 5 | 5 | 5 | 5 | 5 | 5 | – |
| 221 | 300 | 5 | 5 | 4 | 5 | 5 | 4 | – |
| 222 | 300 | 5 | 5 | 5 | 4 | 4 | 5 | – |

TABLE 66-continued

| Com'd No. | Dosage (g/ha) | Herbicidal efficacy | | | | | | Phytotoxicity |
|---|---|---|---|---|---|---|---|---|
| | | AA | BB | CC | DD | EE | FF | Corn |
| 223 | 300 | 5 | 5 | 5 | 5 | 5 | 5 | – |
| 224 | 300 | 5 | 5 | 5 | 5 | 5 | 5 | – |
| 225 | 300 | 4 | 5 | 5 | 5 | 5 | 5 | – |
| 226 | 300 | 4 | 5 | 5 | 5 | 5 | 5 | – |
| 227 | 300 | 5 | 5 | 4 | 4 | 5 | 5 | – |
| 228 | 300 | 5 | 5 | 5 | 5 | 5 | 5 | – |
| 229 | 300 | 5 | 5 | 5 | 5 | 5 | 5 | – |
| 230 | 300 | 5 | 5 | 5 | 5 | 5 | 5 | – |
| 231 | 300 | 5 | 5 | 5 | 5 | 4 | 4 | – |
| 232 | 300 | 5 | 5 | 5 | 5 | 5 | 5 | – |
| 233 | 300 | 5 | 5 | 5 | 5 | 5 | 5 | – |
| 234 | 300 | 5 | 5 | 5 | 5 | 5 | 5 | – |
| 235 | 300 | 5 | 5 | 5 | 5 | 5 | 5 | – |
| 236 | 300 | 5 | 5 | 5 | 5 | 5 | 5 | – |
| 237 | 300 | 5 | 5 | 5 | 5 | 5 | 5 | – |
| 238 | 300 | 5 | 5 | 5 | 5 | 5 | 5 | – |
| 239 | 300 | 5 | 5 | 5 | 5 | 5 | 5 | – |
| 240 | 300 | 5 | 5 | 5 | 5 | 5 | 5 | – |
| 241 | 300 | 5 | 5 | 5 | 5 | 5 | 5 | – |
| 242 | 300 | 5 | 5 | 5 | 5 | 5 | 4 | – |
| 243 | 300 | 5 | 5 | 5 | 5 | 4 | 4 | – |
| 244 | 300 | 5 | 5 | 5 | 5 | 4 | 4 | – |
| 250 | 300 | 5 | 5 | 5 | 5 | 4 | 4 | – |
| 251 | 300 | 5 | 5 | 5 | 5 | 5 | 5 | ± |
| F | 300 | 5 | 5 | 5 | 5 | 2 | 1 | ++ |

AA = Cocklebur, BB = Velvetleaf, CC = Common lambsquaters, DD = Common ragweed, EE = Large crabgrass, FF = Green foxtail Table 66 shows that the herbicides of the present invention cause almost no phytotoxicity on corn and further that they can selectively control upland soil weeds at a low dosage. In contrast, it is shown that Compound F is poor in safety for corn and efficacy on upland soil weeds.

Industrial Applicability

The cyclohexanedione derivative of the present invention can selectively control a broad range of upland soil weeds at a low dosage both in pre-emergence treatment and in post-emergence treatment without causing phytotoxicity on crops cultivated in upland fields such as corn.

What is claimed is:

1. A cyclohexanedione compound of the formula (I) or a salt thereof,

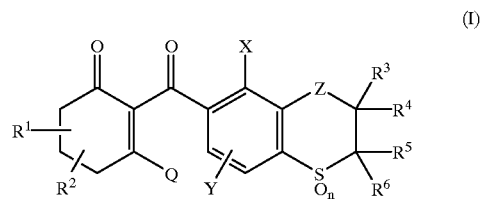

(I)

wherein each of $R^1$ and $R^2$ is independently a hydrogen atom or a $C_1$–$C_6$ alkyl group, each of $R^3$, $R^4$, $R^5$ and $R^6$ is independently a hydrogen atom, a $C_1$–$C_6$ alkyl group, a $C_1$–$C_6$ haloalkyl group or a halogen atom, n is 0, 1 or 2, X is a $C_1$–$C_6$ alkyl group, a $C_1$–$C_6$ haloalkyl group, a halogen atom, a $C_1$–$C_6$ alkoxy group, a $C_1$–$C_6$ haloalkoxy group, a $C_2$–$C_6$ alkoxyalkyl group, a $C_1$–$C_6$ alkylthio group, a $C_1$–$C_6$ haloalkylthio group, a $C_1$–$C_6$ alkylsulfinyl group or a $C_1$–$C_6$ alkylsulfonyl group, Y is a hydrogen atom, a $C_1$–$C_6$ alkyl group, a $C_1$–$C_6$ haloalkyl group, a halogen atom, a $C_1$–$C_6$ alkoxy group, a $C_1$–$C_6$ haloalkoxy group or a $C_2$–$C_6$ alkoxyalkyl group, Z is a group of (a)

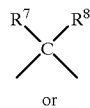

or (b)

in which each of $R^7$ and $R^8$ is independently a hydrogen atom, a halogen atom, a $C_1$–$C_6$ alkyl group, a $C_1$–$C_6$ alkoxy group, a $C_1$–$C_6$ alkylthio group or a group of -$NR^{10}R^{11}$, provided that when $R^7$ or $R^8$ is or both $R^7$ and $R^8$ are $C_1$–$C_6$ alkyl, $C_1$–$C_6$ alkoxy or $C_1$–$C_6$ alkylthio group or groups, hydrogen atoms thereof optionally are replaced with 1 to 13 halogen atoms or $C_1$–$C_6$ alkoxy groups, when the number of carbon atoms thereof is $C_2$–$C_6$, the group or groups optionally contain an unsaturated bond, and when the number of carbon atoms thereof is $C_3$–$C_6$, the group or groups optionally have a cyclic structure, each of $R^{10}$ and $R^{11}$ is a hydrogen atom, a $C_1$–$C_6$ alkyl group or a $C_1$–$C_6$ alkylcarbonyl group, when both $R^7$ and $R^8$ are $C_1$–$C_6$ alkyl groups, $C_1$–$C_6$ alkoxy groups or $C_1$–$C_6$ alkylthio groups, carbon atoms of $R^7$ and $R^8$ optionally bond to each other to form a 3- to 7-membered ring, provided that when both $R^7$ and $R^8$ are alkyl groups, compounds of the formula (I) in which X is a $C_1$–$C_6$ alkyl group, a halogen atom or a haloalkyl group and all of $R^3$, $R^4$, $R^5$ and $R^6$ are hydrogen atoms are excluded, when one of $R^7$ and $R^8$ is an alkoxy group and when the other is a hydrogen atom, compounds of the formula (I) in which X is a $C_1$–$C_6$ alkyl group and all of $R^3$, $R^4$, $R^5$ and $R^6$ are hydrogen atoms are excluded when no hydrogen atom of the alkoxy group is replaced with a halogen or an alkoxy group or when the alkoxy group does not contain an unsaturated bond or a cyclic structure, and $R^9$ is an oxygen atom, a sulfur atom or a $C_1$–$C_6$ alkoxyimino group, when $R^9$ is a $C_1$–$C_6$ alkoxyimino group, hydrogen atoms thereof optionally are replaced with 1 to 13 halogen atoms, when the number of carbon atoms thereof is 2 to 6, the alkoxyimino group having 2 to 6 carbon atoms optionally contains an unsaturated bond, and when $R^9$ is an alkoxyimino group and when no hydrogen atom thereof is replaced with a halogen or when the alkoxyimino group does not contain an unsaturated bond, compounds of the formula (I) in which X is a $C_1$–$C_6$ alkyl group and all of $R^3$, $R^4$, $R^5$ and $R^6$ are hydrogen atoms are excluded, and Q is a hydroxyl group or a group of (c)

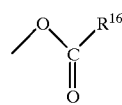

or (d)

in which each of $R^{16}$ and $R^{17}$ is a $C_1$–$C_6$ alkyl group, a $C_1$–$C_6$ haloalkyl group or a phenyl group on which a $C_1$–$C_6$ alkyl group, a $C_1$–$C_6$ haloalkyl group, a halogen atom, a cyano group or a nitro group optionally is substituted, and m is 0, 1 or 2.

2. A cyclohexanedione compound of the formula (I-a1), or a salt thereof, (I-a1)

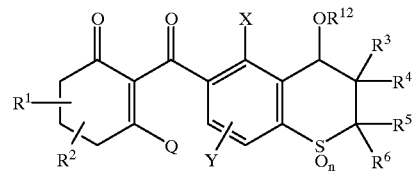

wherein each of $R^1$ and $R^2$ is independently a hydrogen atom or a $C_1$–$C_6$ alkyl group, each of $R^3$, $R^4$, $R^5$ and $R^6$ is independently a hydrogen atom, a $C_1$–$C_6$ alkyl group, a $C_1$–$C_6$ haloalkyl group or a halogen atom, n is 0, 1 or 2, X is a $C_1$–$C_6$ alkyl group, a $C_1$–$C_6$ haloalkyl group, a halogen atom, a $C_1$–$C_6$ alkoxy group, a $C_1$–$C_6$ haloalkoxy group, a $C_1$–$C_6$ alkoxyalkyl group, a $C_1$–$C_6$ alkylthio group, a $C_1$–$C_6$ haloalkylthio group, a $C_1$–$C_6$ alkylsulfinyl group or a $C_1$–$C_6$ alkylsulfonyl group, Y is a hydrogen atom, a $C_1$–$C_6$ alkyl group, $C_1$–$C_6$ haloalkyl group, a halogen atom, a $C_1$–$C_6$ alkoxy group, a $C_1$–$C_6$ haloalkoxy group or a $C_2$–$C_6$ alkoxyalkyl group, $R^{12}$ is a $C_1$–$C_6$ alkyl group or a $C_1$–$C_6$ haloalkyl group, $R^{12}$ is optionally substituted with a $C_1$–$C_6$ alkoxy group; when the number of carbon atoms of $R^{12}$ is 2 to 6, $R^{12}$ optionally contains an unsaturated bond; when the number of carbon atoms of $R^{12}$ is 3 to 6, $R^{12}$ optionally has a cyclic structure; when $R^{12}$ is a $C_1$–$C_6$ alkyl, compounds of the formula (I-a1) in which X is a $C_1$–$C_6$ alkyl and all of $R^3$, $R^4$, $R^5$ and $R^6$ are hydrogen atoms are excluded, and Q is a hydroxyl group or a group of (c)

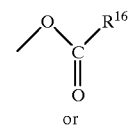

or (d)

in which each of $R^{16}$ and $R^{17}$ is a $C_1$–$C_6$ alkyl group, a $C_1$–$C_6$ haloalkyl group or a phenyl group on which a $C_1$–$C_6$ alkyl group, a $C_1$–$C_6$ haloalkyl group, a halogen atom, a cyano group or a nitro group is optionally substituted, and m is 0, 1 or 2.

3. A cyclohexanedione compound of the formula (I-a2), or a salt thereof,

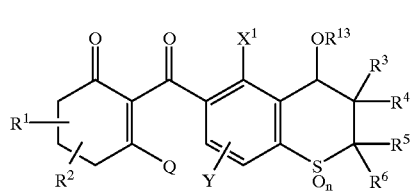

(I-a2)

wherein each of $R^1$ and $R^2$ is independently a hydrogen atom or a $C_1$–$C_6$ alkyl group, each of $R^3$, $R^4$, $R^5$ and $R^6$ is independently a hydrogen atom, a $C_1$–$C_6$ alkyl group, a $C_1$–$C_6$ haloalkyl group or a halogen atom, $R^{13}$ is a $C_1$–$C_6$ alkyl group, n is 0, 1 or 2, $X^1$ is a $C_1$–$C_6$ haloalkyl group, a halogen atom, a $C_1$–$C_6$ alkoxy group, a $C_1$–$C_6$ haloalkoxy group, a $C_1$–$C_6$ alkoxyalkyl group, a $C_1$–$C_6$ alkylthio group, a $C_1$–$C_6$ haloalkylthio group, a $C_1$–$C_6$ alkylsulfinyl group or a $C_1$–$C_6$ alkylsulfonyl group, Y is a hydrogen atom, a $C_1$–$C_6$ alkyl group, $C_1$–$C_6$ haloalkyl group, a halogen atom, a $C_1$–$C_6$ alkoxy group, a $C_1$–$C_6$ haloalkoxy group or a $C_2$–$C_6$ alkoxyalkyl group, and Q is a hydroxyl group or a group of

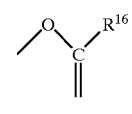

(c)

or

(d)

in which each of $R^{16}$ and $R^{17}$ is a $C_1$–$C_6$ alkyl group, a $C_1$–$C_6$ haloalkyl group or a phenyl group on which a $C_1$–$C_6$ alkyl group, a $C_1$–$C_6$ haloalkyl group, a halogen atom, a cyano group or a nitro group is optionally substituted, and m is 0, 1 or 2.

4. A cyclohexanedione compound of the formula (I-a3), or a salt thereof,

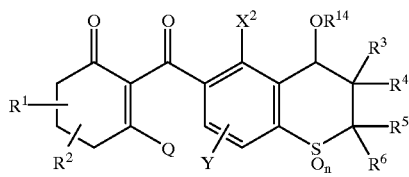

(I-a3)

wherein each of $R^1$ and $R^2$ is independently a hydrogen atom or a $C_1$–$C_6$ alkyl group, each of $R^3$, $R^4$, $R^5$ and $R^6$ is independently a hydrogen atom, a $C_1$–$C_6$ alkyl group, a $C_1$–$C_6$ haloalkyl, or a halogen atom;

$R^{14}$ is a $C_1$–$C_6$ haloalkyl group, an alkoxyalkyl group, an alkenyl group, a haloalkenylalkyl group or an alkynylalkyl group, n is 0, 1 or 2, $X^2$ is a $C_1$–$C_6$ alkyl group, a $C_1$–$C_6$ haloalkyl group, a halogen atom, a $C_1$–$C_6$ alkoxy group, a $C_1$–$C_6$ haloalkoxy group, a $C_2$–$C_6$ alkoxyalkyl group, a $C_1$–$C_6$ alkylthio group, a $C_1$–$C_6$ haloalkylthio group, a $C_1$–$C_6$ alkylsulfinyl group or a $C_1$–$C_6$ alkylsulfonyl group, Y is a hydrogen atom, a $C_1$–$C_6$ alkyl group, a $C_1$–$C_6$ haloalkyl group, a halogen atom, a $C_1$–$C_6$ alkoxy group, a $C_1$–$C_6$ haloalkoxy group or a $C_2$–$C_6$ alkoxyalkyl group, and Q is a hydroxyl group or a group of (c)

or (d)

in which each of $R^{16}$ and $R^{17}$ is a $C_1$–$C_6$ alkyl group, a $C_1$–$C_6$ haloalkyl group or a phenyl group on which a $C_1$–$C_6$ alkyl group, a $C_1$–$C_6$ haloalkyl group, a halogen atom, a cyano group or a nitro group is optionally substituted, and m is 0, 1 or 2.

5. A cyclohexanedione compound of the formula (I-b1),

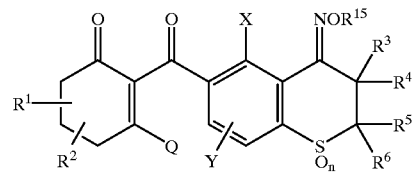

(I-b1)

wherein each of $R^1$ and $R^2$ is independently a hydrogen atom or a $C_1$–$C_6$ alkyl group, each of $R^3$, $R^4$, $R^5$ and $R^6$ is independently a hydrogen atom, a $C_1$–$C_6$ alkyl group, a $C_1$–$C_6$ haloalkyl group or a halogen atom, n is 0, 1 or 2, X is a $C_1$–$C_6$ alkyl group, $C_1$–$C_6$ haloalkyl group, a halogen atom, a $C_1$–$C_6$ alkoxy group, a $C_1$–$C_6$ haloalkoxy group, a $C_2$–$C_6$ alkoxyalkyl group, a $C_1$–$C_6$ alkylthio group, a $C_1$–$C_6$ haloalkylthio group, a $C_1$–$C_6$ alkylsulfinyl group or a $C_1$–$C_6$ alkylsulfonyl group, Y is a hydrogen atom, a $C_1$–$C_6$ alkyl group, $C_1$–$C_6$ haloalkyl group, a halogen atom, a $C_1$–$C_6$ alkoxy group, a $C_1$–$C_6$ haloalkoxy group or a $C_2$–$C_6$ alkoxyalkyl group, $R^{15}$ is a $C_1$–$C_6$ alkyl group or a $C_2$–$C_6$ alkenyl group, when $R^{15}$ is a $C_1$–$C_6$ alkyl group, compounds of the formula (I-b1) in which X is a $C_1$–$C_6$ alkyl group and all of $R^3$, $R^4$, $R^5$ and $R^6$ are hydrogen atoms are excluded, and Q is a hydroxyl group or a group of

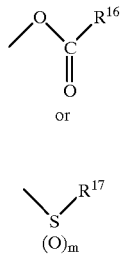

in which each of $R^{16}$ and $R^{17}$ is a $C_1$–$C_6$ alkyl group, a $C_1$–$C_6$ haloalkyl group or a phenyl group on which a $C_1$–$C_6$ alkyl group, a $C_1$–$C_6$ haloalkyl group, a halogen atom, a cyano group or a nitro group is optionally substituted, and m is 0, 1 or 2.

6. A cyclohexanedione compound of the formula (I-b2), or a salt thereof,

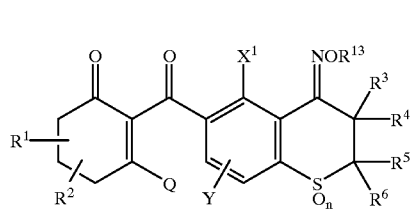

(I-b2)

wherein each of $R^1$ and $R^2$ is independently a hydrogen atom or a $C_1$–$C_6$ alkyl group, each of $R^3$, $R^4$, $R^5$ and $R^6$ is independently a hydrogen atom, a $C_1$–$C_6$ alkyl group, a $C_1$–$C_6$ haloalkyl group or a halogen atom, $R^{13}$ is a $C_1$–$C_6$ alkyl group, n is 0, 1 or 2, $X^1$ is a $C_1$–$C_6$ haloalkyl group, a halogen atom, a $C_1$–$C_6$ alkoxy group, a $C_1$–$C_6$ haloalkoxy group, a $C_2$–$C_6$ alkoxyalkyl group, a $C_1$–$C_6$ alkylthio group, a $C_1$–$C_6$ haloalkylthio group, a $C_1$–$C_6$ alkylsulfinyl group or a $C_1$–$C_6$ alkylsulfonyl group, Y is a hydrogen atom, a $C_1$–$C_6$ alkyl group, $C_1$–$C_6$ haloalkyl group, a halogen atom, a $C_1$–$C_6$ alkoxy group, a $C_1$–$C_6$ haloalkoxy group or a $C_2$–$C_6$ alkoxyalkyl group, and Q is a hydroxyl group or a group of

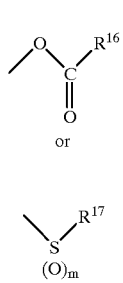

in which each of $R^{16}$ and $R^{17}$ is a $C_1$–$C_6$ alkyl group, a $C_1$–$C_6$ haloalkyl group or a phenyl group on which a $C_1$–$C_6$ alkyl group, a $C_1$–$C_6$ haloalkyl group, a halogen atom, a cyano group or a nitro group is optionally substituted, and m is 0, 1 or 2.

7. A cyclohexanedione compound of the formula (I-c), or a salt thereof,

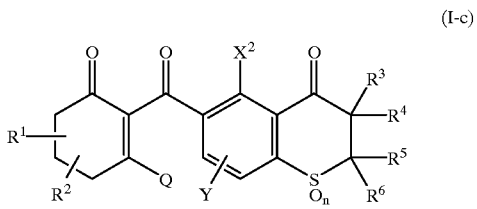

(I-c)

wherein each of $R^1$ and $R^2$ is independently a hydrogen atom or a $C_1$–$C_6$ alkyl group, each of $R^3$, $R^4$, $R^5$ and $R^6$ is independently a hydrogen atom, a $C_1$–$C_6$ alkyl group, a $C_1$–$C_6$ haloalkyl group or a halogen atom, n is 0, 1 or 2, $X^2$ is a $C_1$–$C_6$ alkyl group, a $C_1$–$C_6$ haloalkyl group, a halogen atom, a $C_1$–$C_6$ alkoxy group, a $C_1$–$C_6$ haloalkoxy group, a $C_2$–$C_6$ alkoxyalkyl group, a $C_1$–$C_6$ alkylthio group, a $C_1$–$C_6$ haloalkylthio group, a $C_1$–$C_6$ alkylsulfinyl group or a $C_1$–$C_6$ alkylsulfonyl group, Y is a hydrogen atom, a $C_1$–$C_6$ alkyl group, $C_1$–$C_6$ haloalkyl group, a halogen atom, a $C_1$–$C_6$ alkoxy group, a $C_1$–$C_6$ haloalkoxy group or a $C_2$–$C_6$ alkoxyalkyl group, and Q is a hydroxyl group or a group of

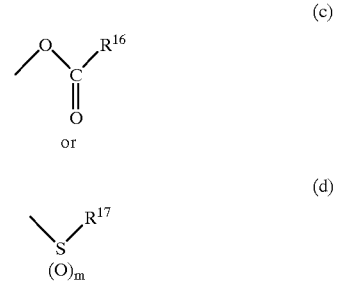

in which each of $R^{16}$ and $R^{17}$ is a $C_1$–$C_6$ alkyl group, a $C_1$–$C_6$ haloalkyl group or a phenyl group on which a $C_1$–$C_6$ alkyl group, a $C_1$–$C_6$ haloalkyl group, a halogen atom, a cyano group or a nitro group is optionally substituted, and m is 0, 1 or 2.

8. The cyclohexanedione compound or salt thereof, according to claim 1, wherein each of $R^3$, $R^4$, $R^5$ and $R^6$ is independently a hydrogen atom or methyl.

9. The cyclohexanedione compound or salt thereof, according to claim 1, wherein Y is substituted on the 8-position of the thiochroman ring.

10. The cyclohexanedione compound or salt thereof, according to claim 1, wherein n is 0 or 2.

11. A herbicide composition containing, as an active ingredient, a herbicidally effective amount of at least one cyclohexanedione compound or salt thereof recited in claim 1, in combination with a carrier.

12. The cyclohexanedione compound or salt thereof, according to claim 2, wherein each of $R^3$, $R^4$, $R^5$ and $R^6$ is independently a hydrogen atom or methyl.

13. The cyclohexanedione compound or salt thereof, according to claim 2, wherein Y is substituted on the 8-position of the thiochroman ring.

14. The cyclohexanedione compound or salt thereof, according to claim 2, wherein n is 0 or 2.

15. A herbicide composition containing, as an active ingredient, a herbicidally effective amount of at least one cyclohexanedione compound or salt thereof, recited in claim 2, in combination with a carrier.

16. The cyclohexanedione compound or salt thereof, according to claim 3, wherein each of $R^3$, $R^4$, $R^5$ and $R^6$ is independently a hydrogen atom or methyl.

17. The cyclohexanedione compound or salt thereof, according to claim 3, wherein Y is substituted on the 8-position of the thiochroman ring.

18. The cyclohexanedione compound or salt thereof, according to claim 3, wherein n is 0 or 2.

19. A herbicide composition containing, as an active ingredient, a herbicidally effective amount of at least one cyclohexanedione compound or salt thereof, recited in claim 3, in combination with a carrier.

20. The cyclohexanedione compound or salt thereof, according to claim 4, wherein each of $R^3$, $R^4$, $R^5$ and $R^6$ is independently a hydrogen atom or methyl.

21. The cyclohexanedione compound or salt thereof, according to claim 4, wherein Y is substituted on the 8-position of the thiochroman ring.

22. The cyclohexanedione compound or salt thereof, according to claim 4, wherein n is 0 or 2.

23. A herbicide composition containing, as an active ingredient, a herbicidally effective amount of at least one cyclohexanedione compound or the salt thereof, recited in claim 4, in combination with a carrier.

24. The cyclohexanedione compound or salt thereof, according to claim 4, wherein $R^3$, $R^4$, $R^5$ and $R^6$ is independently a hydrogen atom or methyl.

25. The cyclohexanedione compound or salt thereof, according to claim 4, wherein Y is substituted on the on the 8-position of the thiochroman ring.

26. The cyclohexanedione compound or salt thereof, according to claim 4, wherein n is 0 or 2.

27. A herbicide composition containing, as an active ingredient, a herbicidally effective amount of at least one cyclohexanedione compound or salt thereof, recited in claim 4, in combination with a carrier.

28. The cyclohexanedione compound or salt thereof, according to claim 6, wherein each of $R^3$, $R^4$, $R^5$ and $R^6$ is independently a hydrogen atom or methyl.

29. The cyclohexanedione compound or salt thereof, according to claim 6, wherein Y is substituted on the 8-position of the thiochroman ring.

30. The cyclohexanedione compound or salt thereof, according to claim 6, wherein n is 0 or 2.

31. A herbicide composition containing, as an active ingredient, a herbicidally effective amount of at least one cyclohexanedione compound or salt thereof, recited in claim 6, in combination with a carrier.

32. The cyclohexanedione compound or salt thereof, according to claim 7, wherein each of $R^3$, $R^4$, $R^5$ and $R^6$ is independently a hydrogen atom or methyl.

33. The cyclohexanedione compound or salt thereof, according to claim 7, wherein Y is substituted on the 8-position of the thiochroman ring.

34. The cyclohexanedione compound or salt thereof, according to claim 7, wherein n is 0 or 2.

35. A herbicide composition containing, as an active ingredient, a herbicidally effective amount of at least one cyclohexanedione compound or salt thereof, recited in claim 7, in combination with a carrier.

36. A method of combatting weeds comprising applying to weeds or to soil an effective herbicidal amount of a compound of claim 1.

37. A method of combatting weeds comprising applying to weeds or to soil an effective herbicidal amount of a compound of claim 2.

38. A method of combatting weeds comprising applying to weeds or to soil an effective herbicidal amount of a compound of claim 3.

39. A method of combatting weeds comprising applying to weeds or to soil an effective herbicidal amount of a compound of claim 4.

40. A method of combatting weeds comprising applying to weeds or to soil an effective herbicidal amount of a compound of claim 5.

41. A method of combatting weeds comprising applying to weeds or to soil an effective herbicidal amount of a compound of claim 6.

42. A method of combatting weeds comprising applying to weeds or to soil an effective herbicidal amount of a compound of claim 7.

\* \* \* \* \*